(12) United States Patent
Ebright et al.

(10) Patent No.: US 9,415,112 B2
(45) Date of Patent: Aug. 16, 2016

(54) BIPARTITE INHIBITORS OF BACTERIAL RNA POLYMERASE

(75) Inventors: Richard H. Ebright, New Brunswick, NJ (US); David Degen, New Brunswick, NJ (US); Yu Zhang, New Brunswick, NJ (US); Yon Ebright, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/128,391

(22) PCT Filed: Jun. 20, 2012

(86) PCT No.: PCT/US2012/043360
§ 371 (c)(1),
(2), (4) Date: Dec. 20, 2013

(87) PCT Pub. No.: WO2012/177770
PCT Pub. Date: Dec. 27, 2012

(65) Prior Publication Data
US 2014/0206602 A1    Jul. 24, 2014

Related U.S. Application Data

(60) Provisional application No. 61/498,970, filed on Jun. 20, 2011.

(51) Int. Cl.
| | | |
|---|---|---|
| A61K 38/00 | (2006.01) | |
| A61K 47/48 | (2006.01) | |
| C07D 498/04 | (2006.01) | |
| C07K 7/56 | (2006.01) | |
| C12N 9/12 | (2006.01) | |
| C07K 5/072 | (2006.01) | |

(52) U.S. Cl.
CPC ........ *A61K 47/48115* (2013.01); *C07D 498/04* (2013.01); *C07K 5/06104* (2013.01); *C07K 7/56* (2013.01); *C12N 9/1247* (2013.01)

(58) Field of Classification Search
None
See application file for complete search history.

(56) References Cited

U.S. PATENT DOCUMENTS

| | | | |
|---|---|---|---|
| 7,122,525 B2 | 10/2006 | Michaelis et al. | |
| 7,238,694 B2 | 7/2007 | Ding et al. | |
| 7,247,634 B2 | 7/2007 | Ma et al. | |
| 8,372,839 B2 | 2/2013 | Ebright et al. | |
| 2005/0261262 A1* | 11/2005 | Ma et al. | 514/183 |

FOREIGN PATENT DOCUMENTS

| | | | |
|---|---|---|---|
| EP | 1213298 A1 | 6/2002 | |
| WO | WO 2007/089310 | * | 8/2007 |

OTHER PUBLICATIONS

Sarubbi et al, Mode of action of the microbial metabolite GE23077, a novel potent and selective inhibitor of bacterial RNA polymerase, Eur. J. Biochem. 271, 3146-3154 (2004).*
Campbell et al., "Structural mechanism for rifampicin inhibition of bacterial RNA polymerase", *Cell 104*, 901-912 (2001).
Campbell et al., "Structural, functional, and genetic analysis of sorangicin inhibition of bacterial RNA polymerase", *EMBO J. 24*, 674-682 (2005).
Ho et al., "Structures of RNA polymerase-antibiotic complexes", *Curr. Opin. Structl. Biol. 19*, 715-723 (2009).
Zhang et al., "GE23077 binds to the RNA polymerase 'i' and 'i+1' sites and prevents the binding of initiating nucleotides", eLife 3, e02450 (2014).
Mariani et al., Antibiotics GE23077, novel inhibitors of bacterial RNA polymerase. Part 3: Chemical derivatization, Bioorganic & Medicinal Chemistry Letters, vol. 15 (16), 3748-3752 (2005).
Patent Cooperation Treaty, International Searching Authority, Search Report and Written Opinion for PCT/US2012/043360, 15 pages, dated Oct. 2, 2012.
Villain-Guillot et al., "Progress in targeting bacterial transcription", Drug Discovery Today, vol. 12 (5-6), 200-208 (2007).

* cited by examiner

*Primary Examiner* — Marcela M Cordero Garcia
*Assistant Examiner* — Sergio Coffa
(74) *Attorney, Agent, or Firm* — Viksnins Harris & Padys PLLP

(57) ABSTRACT

The invention provides bipartite inhibitors of bacterial RNA polymerase having the general structural formula (I): X-α-Y (I) wherein X is an moiety that binds to the rifamycin binding site of a bacterial RNA polymerase, Y is a moiety that binds to the GE23077 binding site of a bacterial RNA polymerase, and is a linker. The invention also provides compositions comprising such compounds, methods of making such compounds, and methods of using said compounds. The invention has applications in control of bacterial gene expression, control of bacterial growth, antibacterial chemistry, and antibacterial therapy.

7 Claims, 11 Drawing Sheets

| | | | |
|---|---|---|---|
|RPOB_ECOLI (560)|PIET  PNI|(681) MG  QR| |
|RPOB_HAEIN (560)|PIET  PNI|(682) MG  QR| |
|RPOB_VIBCH (594)|PIET  PNI|(715) MG  QR| |
|RPOB_PSEAE (565)|PIET  PNI|(686) MG  QR| |
|RPOB_TREPA (531)|PIET  PNI|(652) MG  QR| |
|RPOB_BORBU (512)|PIET  PNI|(633) MG  QR| |
|RPOB_XYLFA (592)|PIET  PNI|(713) MG  QR| |
|RPOB_CAMJE (575)|PIET  QNI|(696) MG  QR| |
|RPOB_NEIMA (587)|PIET  PNI|(708) MG  QR| |
|RPOB_RICPR (577)|PIET  QNI|(699) MG  QR|Bacterial RNAP|
|RPOB_CHLTR (505)|PIET  PNI|(626) MG  QR| |
|RPOB_MYCPN (658)|PIET  NI|(781) MG  QR| |
|RPOB_BACSU (516)|PIET  PNI|(639) MG  QR| |
|RPOB_STAAU (515)|PIET  PNI|(638) MG  QR| |
|RPOB_MYCTU (485)|PIET  PNI|(607) MG  QR| |
|RPOB_SYNY3 (414)|PIET  RNA|(537) MG  QR| |
|RPOB_AQUAE (642)|PIET  QNI|(762) MG  QR| |
|RPOB_DEIRA (489)|PIET  ANI|(610) MG  QS| |
|RPOB_TTHER (440)|PIET  PNI|(560) MG  QT| |
|RPOB_THEAQ (440)|PIET  PNI|(560) MG  QT| |
|RPA2_HUMAN (443)|PIET  EPC|(631) YQ| |
|RPB2_HUMAN (511)|PAET  HA|(774) YQ|Human RNAPI, RNAPII, RNAPIII|
|RPC2_HUMAN (481)|PIET  FAC|(685) YQ| |

BIPARTITE INHIBITORS OF BACTERIAL RNA POLYMERASE

CROSS-REFERENCE TO RELATED APPLICATIONS

This application claims priority to U.S. Provisional Application Ser. No. 61/498,970 filed Jun. 20, 2011, the contents of which are incorporated herein by reference.

GOVERNMENT SUPPORT

The invention described herein was made with United States Government support under Grant Numbers AI072766 and GM41376 awarded by the National Institutes of Health. The United States Government has certain rights in the invention.

BACKGROUND ART

Bacterial infections remain among the most common and deadly causes of human disease. Infectious diseases are the third leading cause of death in the United States and the leading cause of death worldwide (Binder et al. (1999) Science 284, 1311-1313). Multi-drug-resistant bacteria now cause infections that pose a grave and growing threat to public health. It has been shown that bacterial pathogens can acquire resistance to first-line and even second-line antibiotics (Stuart B. Levy, The Challenge of Antibiotic Resistance, in Scientific American, 46-53 (March, 1998); Walsh, C. (2000) Nature 406, 775-781; Schluger, N. (2000) Int. J. Tuberculosis Lung Disease 4, S71-S75; Raviglione et al., (2001) Ann. NY Acad. Sci. 953, 88-97). New approaches to drug development are necessary to combat the ever-increasing number of antibiotic-resistant pathogens.

RNA polymerase (RNAP) is the molecular machine responsible for transcription and is the target, directly or indirectly, of most regulation of gene expression (Ebright, R. (2000) J. Mol. Biol. 304, 687-698; Darst, S. (2001) Curr. Opin. Structl. Biol. 11, 155-162; Murakami, K. and Darst, S. (2003) Curr. Opin. Structl. Biol. 13, 31-39; Borukhov, S, and Nudler, E. (2003) Curr. Opin. Microbiol. 6, 93-100; Werner, F. (2007) Mol. Microbiol. 65, 1395-1404; Hirata, A. and Murakami, K. (2009) Curr. Opin. Structl. Biol. 19, 724-731; June, S., Reichlen, M., Tajiri, M. and Murakami, K. (2011) Crit. Rev. Biochem. Mol. Biol. 46, 27-40; Cramer, P. (2002) Curr. Opin. Struct. Biol. 12, 89-97; Cramer, P. (2004) Curr. Opin. Genet. Dev. 14, 218-226; Hahn, S. (2004) Nature Struct. Mol. Biol. 11, 394-403; Kornberg, R. (2007) Proc. Natl. Acad. Sci. USA 104, 12955-12961; Cramer, P., Armache, K., Baumli, S., Benkert, S., Brueckner, F., Buchen, C., Damsma, G., Dengl, S., Geiger, S., Jasiak, A., Jawhari, A., Jennebach, S., Kamenski, T., Kettenberger, Kuhn, C., Lehmann, E., Leike, K., Sydow, J. and Vannini, A. (2008) Annu. Rev. Biophys. 37, 337-352; Lane, W. and Darst, S. (2010) J. Mol. Biol. 395, 671-685; Lane, W. and Darst, S. (2010) J. Mol. Biol. 395, 686-704; Werner, F. and Grohmann, D. (2011) Nature Rev. Microbiol. 9, 85-98; Vannini, A. and Cramer, P. (2012) Mol. Cell 45, 439-446). Bacterial RNAP core enzyme has a molecular mass of ~380,000 Da and consists of one β' subunit, one β subunit, two α subunits, and one ω subunit; bacterial RNAP holoenzyme has a molecular mass of ~450,000 Da and consists of bacterial RNAP core enzyme in complex with the transcription initiation factor σ (Ebright, R. (2000) J. Mol. Biol. 304, 687-698; Darst, S. (2001) Curr. Opin. Structl. Biol. 11, 155-162; Cramer, P. (2002) Curr. Opin. Structl. Biol. 12, 89-97; Murakami and Darst (2003) Curr. Opin. Structl. Biol. 13, 31-39; Borukhov and Nudler (2003) Curr. Opin. Microbiol. 6, 93-100). Bacterial RNAP core subunit sequences are conserved across Gram-positive and Gram-negative bacterial species (Ebright, R. (2000) J. Mol. Biol. 304, 687-698; Darst, S. (2001) Curr. Opin. Structl. Biol. 11, 155-162; Lane, W. and Darst, S. (2010) J. Mol. Biol. 395, 671-685; Lane, W. and Darst, S. (2010) J. Mol. Biol. 395, 686-704;). Eukaryotic RNAP I, RNAP II, and RNAP III contain counterparts of all bacterial RNAP core subunits, but eukaryotic-subunit sequences and bacterial-subunit sequences exhibit only limited conservation (Ebright, R. (2000) J. Mol. Biol. 304, 687-698; Darst, S. (2001) Curr. Opin. Structl. Biol. 11, 155-162; Cramer, P. (2002) Curr. Opin. Structl. Biol. 12, 89-97; Cramer, P. (2004) Curr. Opin. Genet. Dev. 14, 218-226; Lane, W. and Darst, S. (2010) J. Mol. Biol. 395, 671-685; Lane, W. and Darst, S. (2010) J. Mol. Biol. 395, 686-704).

Crystal structures have been determined for bacterial RNAP and eukaryotic RNAP II (Zhang et al., (1999) Cell 98, 811-824; Cramer et al., (2000) Science 288, 640-649; Cramer et al., (2001) Science 292, 1863-1876).

Structures also have been determined for RNAP complexes with nucleic acids, nucleotides and inhibitors (Campbell, et al. (2001) Cell 104, 901-912; Artsimovitch, et al. (2005) Cell 122, 351-363; Campbell, et al. (2005) EMBO J. 24, 674-682; Tuske, et al. (2005) Cell 122, 541-522; Temiaov, et al. (2005) Mol. Cell 19, 655-666; Mukhopadhyay, J., Das, K., Ismail, S., Koppstein, D., Jang, M., Hudson, B., Sarafianos, S., Tuske, S., Patel, J., Jansen, R., Irschik, H., Arnold, E., and Ebright, R. (2008) Cell 135, 295-307; Belogurov, G., Vassylyeva, M., Sevostyanova, A., Appleman, J., Xiang, A., Lira, R., Webber, S., Klyuyev, S., Nudler, E., Artsimovitch, I., and Vassylyev, D. (2009) Nature. 45, 332-335; Vassylyev, D., Vassylyeva, M., Perederina, A., Tahirov, T. and Artsimovitch, I. (2007) Nature 448, 157-162; Vassylyev, D., Vassylyeva, M., Zhang, J., Palangat, M., Artsimovitch, I. and Landick, R. (2007) Nature 448, 163-168; Gnatt, et al. (2001) Science 292, 1876-1882; Westover, et al. (2004a) Science 303, 1014-1016; Westover, et al. (2004b) Cell 119, 481-489; Ketenberger, et al. (2004) Mol. Cell 16, 955-965; Bushnell, et al. (2002) Proc. Natl. Acad. Sci. U.S.A. 99, 1218-1222; Kettenberger, et al. (2005) Natl. Structl. Mol. Biol. 13, 44-48; Ho, M., Hudson, B., Das, K., Arnold, E. and Ebright, R. (2009) Curr. Opin. Structl. Biol. 19, 715-723).

Bacterial RNAP is a proven target for antibacterial therapy (Darst, S. (2004) Trends Biochem. Sci. 29, 159-162; Chopra, I. (2007) Curr. Opin. Investig. Drugs 8, 600-607; Villain-Guillot, P., Bastide, L., Gualtieri, M. and Leonetti, J. (2007) Drug Discov. Today 12, 200-208; Mariani, R. and Maffioli, S. (2009) Curr. Med. Chem. 16, 430-454; Ho, M., Hudson, B., Das, K., Arnold, E. and Ebright, R. (2009) Curr. Opin. Structl. Biol. 19, 715-723; Srivastava, A., Talaue, M., Liu, S., Degen, D., Ebright, R. Y., Sineva, E., Chakraborty, A., Druzhinin, S., Chatterjee, S., Mukhopadhyay, J., Ebright, Y., Zozula, A., Shen, J., Sengupta, S., Niedfeldt, R., Xin, C., Kaneko, T., Irschik, H., Jansen, R., Donadio, S., Connell, N. and Ebright, R. H. (2011) Curr. Opin. Microbiol. 14, 532-543). The suitability of bacterial RNAP as a target for antibacterial therapy follows from the fact that bacterial RNAP is an essential enzyme (permitting efficacy), the fact that bacterial RNAP subunit sequences are conserved (providing a basis for broad-spectrum activity), and the fact that bacterial RNAP subunit sequences are only weakly conserved in eukaryotic RNAP I, RNAP II, and RNAP III (providing a basis for therapeutic selectivity).

The rifamycin antibacterial agents—notably rifampin, rifapentine, and rifabutin—function by binding to and inhibiting bacterial RNAP (Darst, S. (2004) *Trends Biochem. Sci.* 29, 159-162; Ho, M., Hudson, B., Das, K., Arnold, E. and Ebright, R. (2009) *Curr. Opin. Structl. Biol.* 19, 715-723; Floss and Yu (2005) *Chem. Rev.* 105, 621-632; Campbell, et al. (2001) *Cell* 104, 901-912; Artsimovitch, et al. (2005) *Cell* 122, 351-363; Feklistov, A., Mekler, V., Jiang, Q., Westblade, L., Irschik, H., Jansen, R., Mustaev, A., Darst, S., and Ebright, R. (2008) *Proc. Natl. Acad. Sci. USA* 105, 14820-14825). The rifamycins bind to a site on bacterial RNAP adjacent to the RNAP active center and prevent the extension of RNA chains beyond a length of 2-3 nt.

The rifamycins are in current clinical use in treatment of Gram-positive and Gram-negative bacterial infections (Darst, S. (2004) *Trends Biochem. Sci.* 29, 159-162; Ho, M., Hudson, B., Das, K., Arnold, E. and Ebright, R. (2009) *Curr. Opin. Structl. Biol.* 19, 715-723; Floss and Yu (2005) *Chem. Rev.* 105, 621-632; Campbell, et al. (2001) *Cell* 104, 901-912). The rifamycins are first-line treatments for tuberculosis and are the only current first-line treatments for tuberculosis able to kill non-replicating tuberculosis bacteria, to clear infection, and to prevent relapse (Mitchison, D. (2000) *Int. J. Tuberc. Lung Dis.* 4, 796-806). The rifamycins also are first-line treatments for biofilm-associated infections of catheters and implanted medical devices and are among the very few current antibacterial drugs able to kill non-replicating biofilm-associated bacteria (Obst, G., Gagnon, R. F., Prentis, J. and Richards, G. K. (1988) *ASAIO Trans.* 34, 782-784; Obst, G., Gagnon, R. F., Harris, A., Prentis, J. and Richards, G. K. (1989) *Am. J. Nephroi.* 9, 414-420; Villain-Guillot, P., Gualtieri, M., Bastide, L. and Leonetti, J. P. (2007) *Antimicrob. Agents Chemother.* 51, 3117-3121.

The clinical utility of the rifamycin antibacterial agents is threatened by the emergence and spread of bacterial strains resistant to known rifamycins (Darst, S. (2004) *Trends Biochem. Sci.* 29, 159-162; Ho, M., Hudson, B., Das, K., Arnold, E. and Ebright, R. (2009) *Curr. Opin. Structl. Biol.* 19, 715-723; Floss and Yu (2005) *Chem. Rev.* 105, 621-632; Campbell, et al. (2001) *Cell* 104, 901-912). Resistance to rifamycins typically involves substitution of residues in or immediately adjacent to the rifamycin binding site on bacterial RNAP—i.e., substitutions that directly decrease binding of rifamycins. A significant and increasing percentage of cases of tuberculosis are resistant to rifampicin (1.4% of new cases, 8.7% of previously treated cases, and 100% of cases designated multidrug-resistant, in 1999-2002; Schluger, N. (2000) *Int. J. Tuberc. Lung Dis.* 4, S71-S75; Raviglione, et al. (2001) *Ann. N.Y. Acad. Sci.* 953, 88-97; Zumia, et al. (2001) *Lancet Infect. Dis.* 1, 199-202; Dye, et al. (2002) *J. Infect. Dis.* 185, 1197-1202; WHO/IUATLD (2003) *Anti-tuberculosis drug resistance in the world: third global report* (WHO, Geneva)). Strains of bacterial bioweapons agents resistant to rifampicin can be, and have been, constructed (Lebedeva, et al. (1991) *Antibiot. Khimioter.* 36, 19-22; Pomerantsev, et al. (1993) *Antibiot. Khimioter.* 38, 34-38; Volger, et al. (2002) *Antimicrob. Agents Chemother.* 46, 511-513; Marianelli, et al. (204) *J. Clin. Microbiol.* 42, 5439-5443).

In view of the public-health threat posed by rifamycin-resistant bacterial infections, there is an urgent need for new antibacterial agents that target bacterial RNAP and an especially urgent need for new antibacterial agents that target bacterial RNAP derivatives resistant to known rifamycins. (See Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. and Leonetti, J. (2007) *Drug Discov. Today* 12, 200-208; Mariani, R. and Maffioli, S. (2009) *Curr. Med. Chem.* 16, 430-454; Ho, M., Hudson, B., Das, K., Arnold, E. and Ebright, R. (2009) *Curr. Opin. Structl. Biol.* 19, 715-723; Srivastava, A., Talaue, M., Liu, S., Degen, D., Ebright, R.Y., Sineva, E., Chakraborty, A., Druzhinin, S., Chatterjee, S., Mukhopadhyay, J., Ebright, Y., Zozula, A., Shen, J., Sengupta, S., Niedfeldt, R., Xin, C., Kaneko, T., Irschik, H., Jansen, R., Donadio, S., Connell, N. and Ebright, R. H. (2011) *Curr. Opin. Microbiol.* 14, 532-543.)

SUMMARY OF THE INVENTION

Applicant has identified compounds that inhibit bacterial RNA polymerase (RNAP) and inhibit bacterial growth. Accordingly, one embodiment the invention provides a compound of formula I:

wherein:

X is an moiety that binds to the rifamycin target of a bacterial RNA polymerase;

Y is a moiety that binds to the GE23077 target of a bacterial RNA polymerase; and α is a linker.

The invention also provides a method for making a compound of formula I, wherein the compound is prepared from precursors X-α' and 'α-Y, where α' and 'α are moieties that can react to form α.

The invention also provides a use of a compound of the invention to bind to a bacterial RNA polymerase.

The invention also provides a use of a compound of the invention to inhibit a bacterial RNA polymerase.

The invention also provides a use of a compound of the invention to inhibit bacterial gene expression.

The invention also provides a use of a compound of the invention to inhibit bacterial growth.

The invention also provides a use of a compound of the invention to inhibit a bacterial infection.

The invention also provides a composition comprising a compound of the invention or a pharmaceutically acceptable salt thereof and a pharmaceutically acceptable vehicle.

The invention also provides a method for inhibiting the growth of bacteria comprising contacting the bacteria with a compound of the invention or a salt thereof.

The invention also provides a method for inhibiting a bacterial RNA polymerase comprising contacting the bacterial RNA polymerase with a compound of the invention or a salt thereof.

The invention also provides a method for treating a bacterial infection in a mammal, e.g., a human, comprising administering to the mammal an effective amount of a compound of the invention or a pharmaceutically acceptable salt thereof.

The invention also provides a compound of the invention or a pharmaceutically acceptable salt thereof for use in the prophylactic or therapeutic treatment of a bacterial infection.

The invention also provides the use of a compound of the invention or a pharmaceutically acceptable salt thereof for the preparation of a medicament for treating a bacterial infection in a mammal, e.g., a human.

The invention also provides a compound of the invention or a pharmaceutically acceptable salt thereof for use in medical treatment.

The invention provides a new class of inhibitors of bacterial RNAP. Importantly, the invention provides inhibitors that can exhibit potencies higher than those of known inhibitors. Especially importantly, the invention provides inhibitors that can inhibit bacterial RNAP derivatives resistant to known inhibitors.

The invention provides bipartite inhibitors of bacterial RNAP that contain: (i) a first moiety, X, that binds to the rifamycin binding site on RNAP ("Rif target"; also known as Rif/Sor target") of bacterial RNAP; (ii) a second moiety, Y, that binds to the GE23077 binding site on RNAP ("GE23077 target"); and (iii) a linker, α, connecting said first and second moieties.

The invention provides bipartite inhibitors that interact with bacterial RNAP through simultaneous interactions of X with the Rif target and Y with the GE23077 target. The ability of the bipartite inhibitors to interact with RNAP simultaneously through two moieties, X and Y, can confer an affinity for interaction with bacterial RNAP that is higher than the individual affinities of X and Y. The ability of the bipartite inhibitors to interact with bacterial RNAP through two moieties, X and Y also can confer an ability to interact with a bacterial RNAP derivative resistant to at least one of X and Y.

The bipartite inhibitors have applications in control of bacterial gene expression, control of bacterial growth, antibacterial chemistry, and antibacterial therapy.

The invention also provides intermediates and processes useful for preparing compounds of the invention.

The invention provides a method for preparing a compound that contains: (1) a first moiety, X, that binds to the rifamycin binding site on RNAP ("Rif target"; also known as "Rif/Sor target") of bacterial RNAP; (2) a second moiety, Y, that binds to the GE23077 binding site on RNAP ("GE23077 target"); and (3) a linker, α, connecting said first and second moieties.

The method includes providing precursors X-α' and 'α-Y, and reacting moieties α' and 'α to form α.

For example, one precursor may contain an activated ester, an imidazolide, or an anhydride and the other precursor contain an amine. One precursor may contain a halogen and the other precursor contain an amine. One precursor may contain a halogen and the other precursor contain a sulfhydryl. One precursor may contain a ketone or an aldehyde and the other precursor contain an amine. One precursor may contain an azide and the other precursor contain an alkyne. One precursor may contain an azide and the other precursor contain a phosphine. One precursor may contain a boronic acid and the other precursor contain a substituted phenol. One precursor may contain a phenylboronic acid and the other precursor contain salicylhydroxamic acid.

These and other aspects of the present invention will be better appreciated by reference to the following drawings and Detailed Description.

BRIEF DESCRIPTION OF THE DRAWINGS

FIG. 3 shows a sequence alignment defining the GE23077 target of bacterial RNAP. The sequence alignment shows amino acid residues 565, 566, and 684 of the β subunit of RNAP from *Escherichia coli*; and corresponding residues of the β subunits of *Haemophilus influenzae, Vibrio cholerae, Pseudomonas aeruginosa, Treponema pallidum, Borrelia burgdorferi, Xylella fastidiosa, Campylobacter jejuni, Neisseria meningitides, Rickettsia prowazekii, Thermotoga maritime, Chlamydia trachomatis, Mycoplasma pneumoniae, Bacillus subtilis, Staphylococcus aureus, Mycobacterium tuberculosis, Synechocystis* sp., *Aquifex aeolicus, Deinococcus radiodurans, Thermus thermophilus*, and *Thermus aquaticus* (collectively, the "GE23077 target"); and corresponding residues of the second-largest subunits of human RNAP I, RNAP II and RNAP III.

FIG. 10 shows a structural model of a complex containing RNAP and a representative bipartite inhibitor of this invention comprising rifamycin SV linked to GE23077 ("rifaGE"). In the bipartite inhibitor illustrated, the linker is —NH— and connects C3 of the rifamycin SV fused ring system to the GE23077 acyl-Apa sidechain (compound 3). GE23077 and rifamycin SV are in stick representations (black and white, respectively). Sites of amino acid substitutions that confer GE23077-resistance and rifamycin-resistance are shown in van der Waals representations (dark gray and light gray, respectively). RNAP backbone atoms in and near the GE23077 and rifamycin binding sites are shown in a ribbon representation. The RNAP active-center $Mg^{2+}$ is shown as a sphere and is labelled.

DETAILED DESCRIPTION OF THE INVENTION

Figure 1:
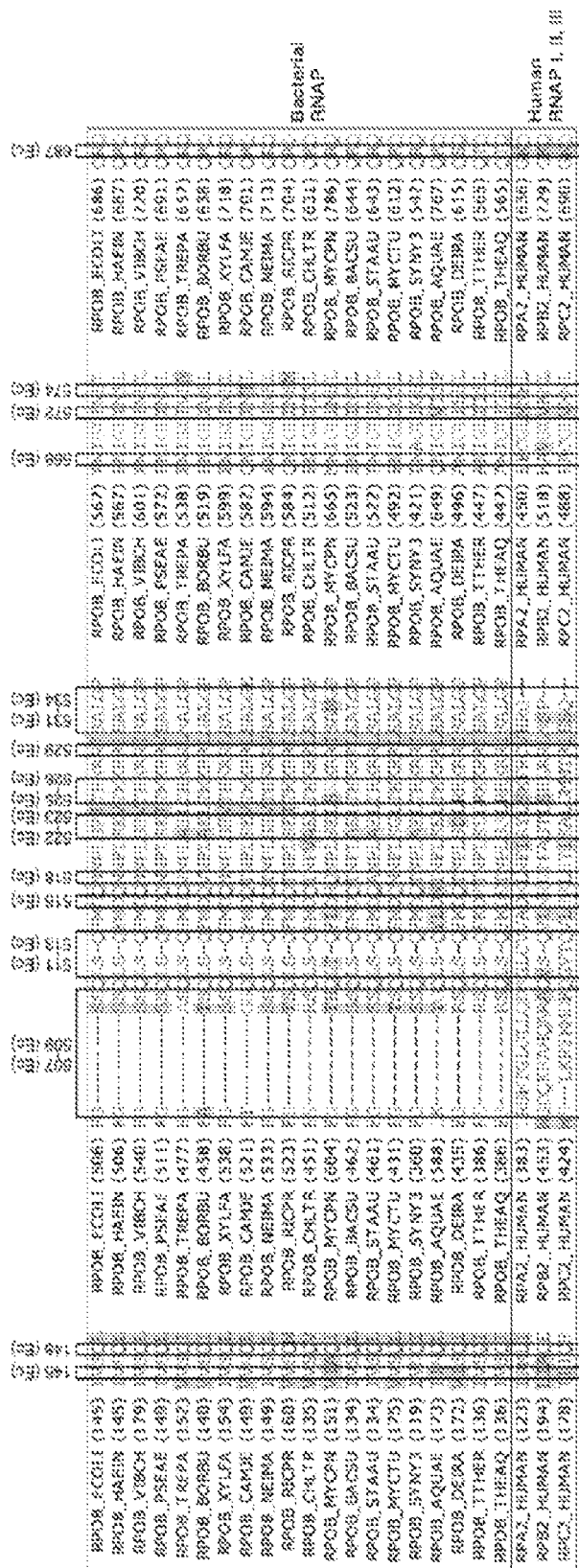
FIG. 1 shows a sequence alignment defining the Rif target of bacterial RNAP. The sequence alignment shows amino acid residues 146, 148, 507-509, 511-513, 516, 518, 522-523, 525-526, 529, 531-534, 568, 572, 574, and 687 of the β subunit of RNAP from *Escherichia coli*; and corresponding residues of the β subunits of *Haemophilus influenzae, Vibrio cholerae, Pseudomonas aeruginosa, Treponema pallidum, Borrelia burgdorferi, Xylella fastidiosa, Campylobacter jejuni, Neisseria meningitides, Rickettsia prowazekii, Thermotoga maritime, Chlamydia trachomatis, Mycoplasma pneumoniae, Bacillus subtilis, Staphylococcus aureus, Mycobacterium tuberculosis, Synechocystis* sp., *Aquifex aeolicus, Deinococcus radiodurans, Thermus thermophilus*, and *Thermus aquaticus* (collectively, the "Rif target"); and corresponding residues of the second-largest subunits of human RNAP I, RNAP II and RNAP III.

The following definitions are used, unless otherwise indicated.

Unless otherwise specified, the term "binds" used herein refers to high-affinity specific binding (i.e., an interaction for which the equilibrium dissociation constant, Kd, is less than about 100 μM and preferably is less than about 10 μM).

Unless otherwise specified, the term "GE23077" used herein encompasses the GE23077 natural-product complex isolated from the microbial producer strain, *Actinomadura* sp. and the individual components of the GE23077 natural-product complex, including GE23077 A, GE23077 A1, GE23077 A2, GE23077 B, GE23077 B1, and GE23077 B2 (see Ciciliato, I., Corti, E., Sarubbi, E., Stefanelli, S., Gastaldo, L., Montanini, N., Kurz, M., Losi, D., Marinelli, F., and Selva, E. (2004) *J. Antibiot.* 57, 210-217; Sarubbi, E., Monti, F., Corti, E., Miele, A., and Selva, E. (2004) *Eur. I Biochem.* 271, 3146-3154; Marazzi, A., Kurz, M., Stefanelli, S., and Colombo, L. (2005) *J. Antibiot.* 58, 260-267; Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752; U.S. Pat. No. 6,586,39).

Unless otherwise specified, the term "GE23077" used herein encompasses the Ama and descarboxy-Ama forms of GE23077 (see Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752).

Unless otherwise specified, the term "rifamycin" used herein encompasses both the napthol (reduced) and napthoquinone (oxidized) forms of a rifamycin, and both the 25-O-acetyl and 25-OH forms of a rifamycin (see Sensi, P., Maggi, N., Furesz, S, and Maffii, G. (1966) *Antimicrobial Agents Chemother* 6, 699-714; Rinehart, K. (1972) *Accts. Chem. Res.* 5, 57-64; Wehrli (1977) *Topics Curr. Chem.* 72, 21-49; Floss, et al. (2005) *Chem. Rev.* 105, 621-632; Aristoff, P., Garcia, G. A., Kirchoff, P. and Showalter, H. D. H. (2010) *Tuberculosis* 90, 94-118).

Unless otherwise specified, structures depicted herein are intended to include all stereochemical forms of the structure; i.e., the R and S configurations for each asymmetric center. Therefore, single stereochemical isomers, as well as enantiomeric and diastereomeric mixtures, of the present compounds are within the scope of the invention.

Unless otherwise specified, structures depicted herein are intended to include compounds which differ only in the presence of one or more isotopically enriched atoms. For example, compounds having the present structures, except for the replacement of a hydrogen atom by a deuterium atom or a tritium atom, or except for the replacement of a carbon by a $^{13}C$-or $^{14}C$-enriched carbon atom, are within the scope of this invention.

Compounds of this invention may exist in tautomeric forms, such as keto-enol tautomers. The depiction of a single tautomer is understood to represent the compound in all of its tautomeric forms.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, (3-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Bipartite Inhibitors of RNAP:

Certain embodiments of the invention provide a new class of inhibitors of RNAP. Certain embodiments of the invention provide novel inhibitors of RNAP that kill bacterial pathogens more potently than current inhibitors. For example, certain embodiments exhibit affinities and inhibition activities higher than known inhibitors. Another aspect of the invention is the provision of novel inhibitors of RNAP that kill bacterial pathogens resistant to current inhibitors.

As described herein, the crystal structure of the RNAP inhibitor GE23077 in complex with RNAP shows (1) the binding site on RNAP for GE23077 is immediately adjacent to the binding site on RNAP for rifamycins; (2) simultaneous binding to RNAP of GE23077 and a rifamycin would be possible; and (3) simultaneous binding to RNAP of GE23077 and a rifamycin would place a defined set of atoms of GE23077 immediately adjacent a defined set of atoms of the rifamycin. Accordingly, certain embodiments of the invention provide bipartite inhibitors of RNAP that contain: (i) a first moiety that binds to the rifamycin binding site of RNAP ("Rif target"; residues alignable to residues 146, 148, 507-509, 511-513, 516, 518, 522-523, 525-526, 529, 531-534, 568, 572, 574, and 687 of *Escherichia coli* RNAP β subunit); (ii) a second moiety that binds to the GE23077 binding site of RNAP ("GE23077 target"; residues alignable to residues 565, 566, and 684 of *Escherichia coli* RNAP beta subunit); and (iii) a linker connecting said first and second moieties.

As a consequence of their higher affinities, RNAP-inhibitory potencies, and antibacterial potencies, certain embodiments of the invention are (1) able to bind to RNAP derivatives resistant to the component first moiety and second moieties; (2) able to inhibit RNAP derivatives resistant to the component first moiety and second moieties; (3) are able to inhibit growth of bacterial strains resistant to the component first moiety and second moieties; and/or (4) less susceptible to emergence of spontaneous resistance than the component first moiety and second moieties. These compounds will have applications in analysis of RNAP structure and function, control of bacterial gene expression, control of bacterial growth, antibacterial chemistry, antibacterial therapy, and drug discovery.

Certain embodiments of the invention provide a compound of formula (I):

X-α-Y     (I)

wherein:

X comprises a moiety that binds to the Rif target of a bacterial RNA polymerase;

Y comprises a moiety that binds to the GE23077 target of a bacterial RNA polymerase;

and

α is a linker.

Certain embodiments of the invention provide a compound of formula (I):

X-α-Y     (I)

wherein:

X is a moiety that binds to the Rif target of a bacterial RNA polymerase;

Y is a moiety that binds to the GE23077 target of a bacterial RNA polymerase; and α is a linker.

Ligands that bind to the Rif target of, and inhibit RNA synthesis by, a bacterial RNAP are known in the art. Such ligands include, for example, rifamycins, streptovaricins, tolypomycins, and sorangicins (Sensi, P., Maggi, N., Furesz, S, and Maffii, G. (1966) *Antimicrobial Agents Chemother* 6, 699-714; Rinehart (1972) *Accts. Chem. Res.* 5, 57-64; Wehrli (1977) *Topics Curr. Chem.* 72, 21-49; Campbell, et al. (2001) *Cell* 104, 901-912; Artsimovitch, et al. (2005) *Cell* 122, 351-363; Floss, et al. (2005) *Chem. Rev.* 105, 621-632; Aristoff, P., Garcia, G. A., Kirchoff, P. and Showalter, H. D. H. (2010) *Tuberculosis* 90, 94-118; Nitta, et al. (1968) *J Antibiotics* 21, 521-522; Monow, et al. (1979) *J Bacteriol.* 137, 374-383; Kondo, et al. (1972) *J Antibiotics* 25, 16-24; Rommelle, et al. (1990) *J Antibiotics* 43, 88-91; O'Niell, et al. (2000) *Antimicrobial Agents Chemother.* 44, 3163-3166; Campbell, et al. (2005) *EMBO J* 24, 1-9).

Rifamycins are a class of antibiotics known in the art (for example, see WO 07/089,310, pages 3-5 and 9). For example, this class includes rifamycin A, rifamycin B, rifamycin C, rifamycin D, rifamycin E, rifamycin S, and rifamycin SV. Additionally, derivatives of rifamycins are known in the art and include, for example, rifampicin (rifampin), rifapentine, rifaximin, rifalazil, and rifabutin.

In certain embodiments, X is selected from a rifamycin, a streptovaricin, a tolypomycin, a sorangicin and derivatives thereof.

In certain embodiments, X is a rifamycin or a rifamycin derivative.

In certain embodiments, X is bonded to α through one of C3 of the rifamycin fused ring system, a moiety pendant from C3 of the rifamycin fused ring system, C4 of the rifamycin fused ring system, a moiety pendant from C4 of the rifamycin fused ring system C11 of the rifamycin fused ring system, and a moiety pendant from C11 of the rifamycin fused ring system.

In certain embodiments, X is rifamycin S, and e.g., X is bonded to α through C3 of the rifamycin S fused ring system or a moiety pendant from C3 of the rifamycin S fused ring system.

In certain embodiments, X is rifamycin SV, and e.g., X is bonded to α through C3 of the rifamycin SV fused ring system or a moiety pendant from C3 of the rifamycin SV fused ring system.

In certain embodiments, X is rifamycin S, and e.g., X is bonded to α through C4 of the rifamycin SV fused ring system or a moiety pendant from C4 of the rifamycin S fused ring system.

In certain embodiments, X is rifamycin SV, and e.g., X is bonded to α through C4 of the rifamycin SV fused ring system or a moiety pendant from C4 of the rifamycin SV fused ring system.

In certain embodiments, X is rifamycin SV, and e.g., X is bonded to α through the oxygen atom pendant from C4 of the rifamycin SV fused ring system.

In certain embodiments, X is a sorangicin or a sorangicin derivative.

In certain embodiments, X is bonded to α through the sorangicin sidechain.

In certain embodiments, X is bonded to α through the carboxyl carbon of the sorangicin sidechain.

In certain embodiments, X is sorangicin A, and e.g., X is bonded to α through the carboxyl carbon of the sorangicin A sidechain.

GE23077 is an inhibitor of bacterial RNAP and is known in the art. For example, see Sarubbi et al., (2004) *Eur. J. Biochem.*, 271(15), 3146-54.

In certain embodiments, Y is GE23077 or a GE23077 derivative.

In certain embodiments, X is rifampin and Y is GE23077.

In certain embodiments, Y is bonded to X through the residue corresponding in position to one of the acyl-Apa residue of GE23077 and the Ama residue of GE23077.

In certain embodiments, Y is bonded to X through the residue corresponding in position to the acyl-Apa residue of GE23077.

In certain embodiments, X is rifamycin S and Y is GE23077.

In certain embodiments, X is rifamycin SV and Y is GE23077.

In certain embodiments, X is sorangicin A and Y is GE23077.

In certain embodiments, α comprises a chain of 0 to about 15 consecutively bonded atoms.

In certain embodiments, α comprises a chain of 0 to about 10 consecutively bonded atoms.

In certain embodiments, α comprises a chain of 0 to about 6 consecutively bonded atoms.

In certain embodiments, α is a bond, and e.g., said bond connects C3 of the rifamycin fused ring system or the carboxyl carbon of the sorangicin sidechain to an atom of the acyl-Apa residue of GE23077.

In certain embodiments, α is —NH— or —S—, and e.g., said —NH— or —S— connects C3 of the rifamycin fused ring system or the carboxyl of the sorangicin sidechain to an atom of the acyl-Apa residue of GE23077.

In certain embodiments, α is —{CH$_2$C(O)Z}—, and e.g., said —{CH$_2$C(O)Z}— connects the oxygen atom pendant from C4 of the rifamycin fused ring system to an atom of the acyl-Apa residue of GE23077; and wherein Z contains from about 0 to about 4 consecutively bonded atoms.

In certain embodiments, α is —{CH$_2$C(O)NHZ'}—; and e.g., said —{CH$_2$C(O)NHZ'}-connects the oxygen atom pendant from C4 of the rifamycin fused ring system to an atom of the acyl-Apa residue of GE23077; and wherein Z' contains from about 0 to about 4 consecutively bonded atoms.

In certain embodiments, α is —(NH—Z")—, and e.g., said —(NH—Z")— connects the carboxyl carbon of the sorangicin sidechain to an atom of the acyl-Apa residue of GE23077; and wherein Z" contains from about 0 to about 4 consecutively bonded atoms.

In certain embodiments, α has a length of from about 0 Å to about 15 Å.

In certain embodiments, α contains covalent bonds.

In certain embodiments, α contains a coordinate-covalent bond.

Certain embodiments of the invention provide a compound, or salt thereof, selected from:

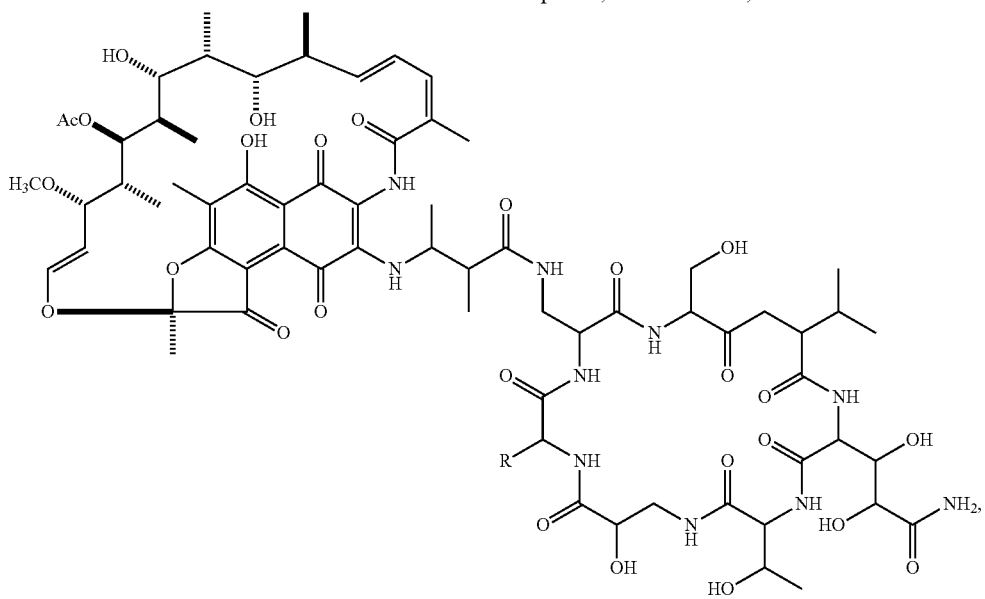

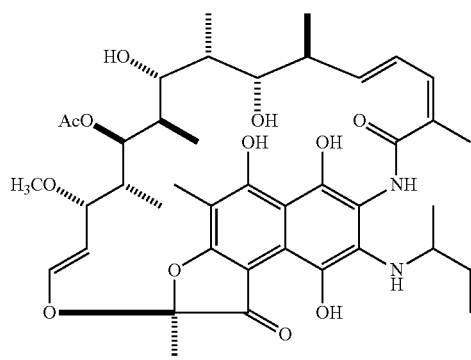
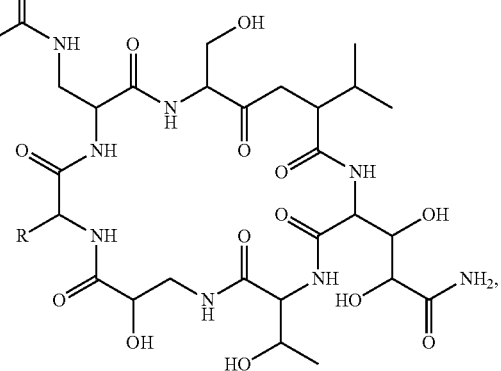
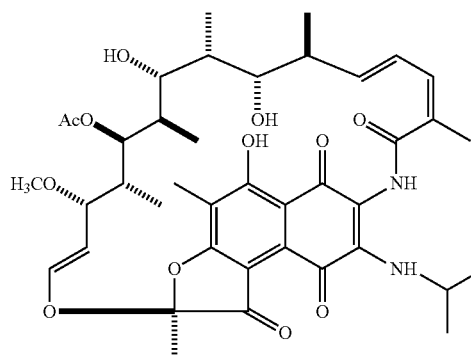
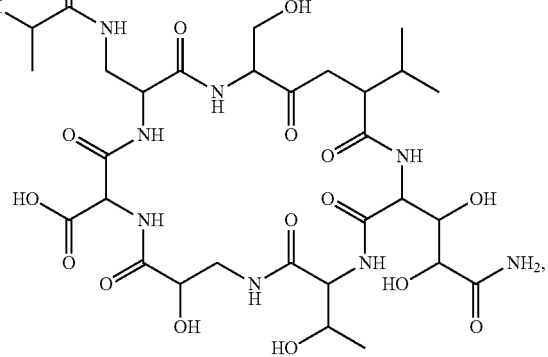

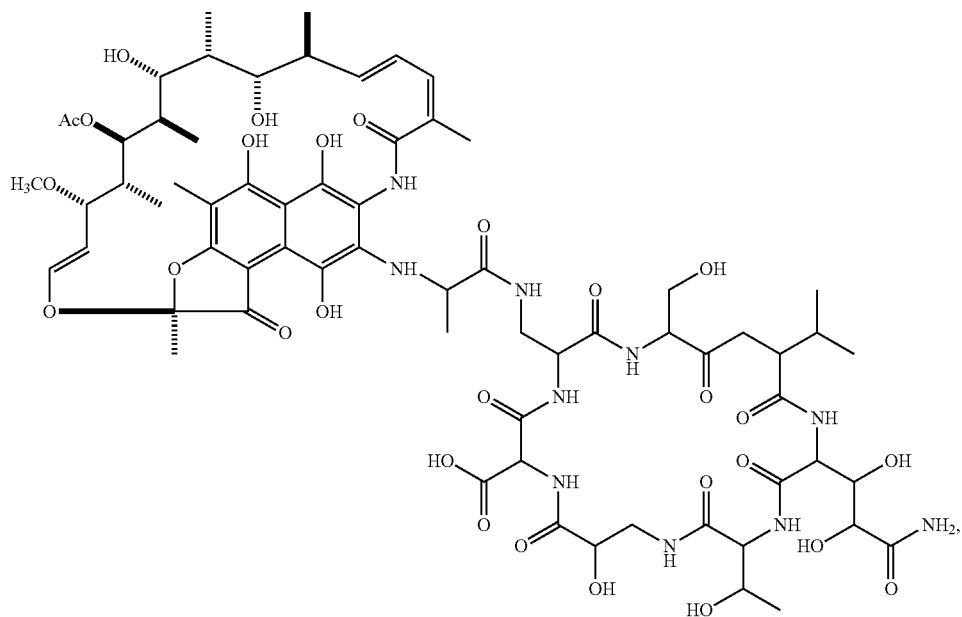
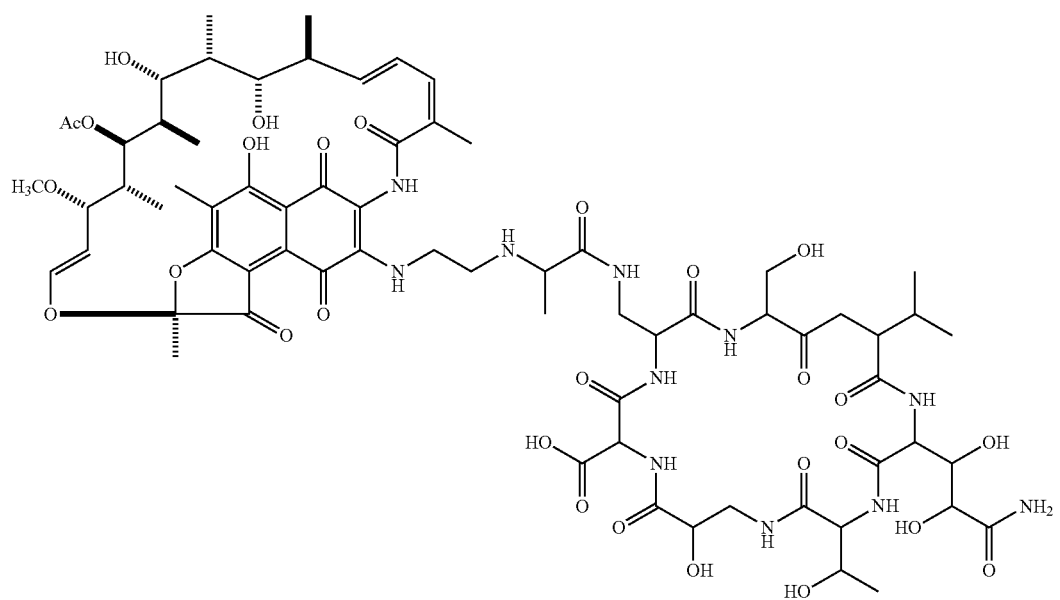

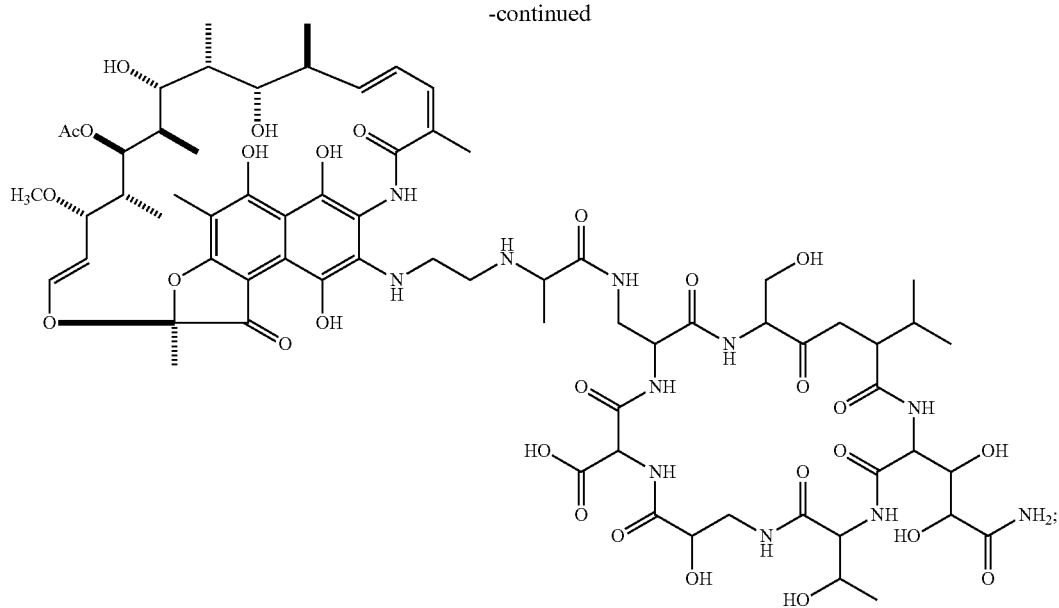
wherein R is H or COOH.
Certain embodiments of the invention provide a compound, or a salt thereof, selected from:
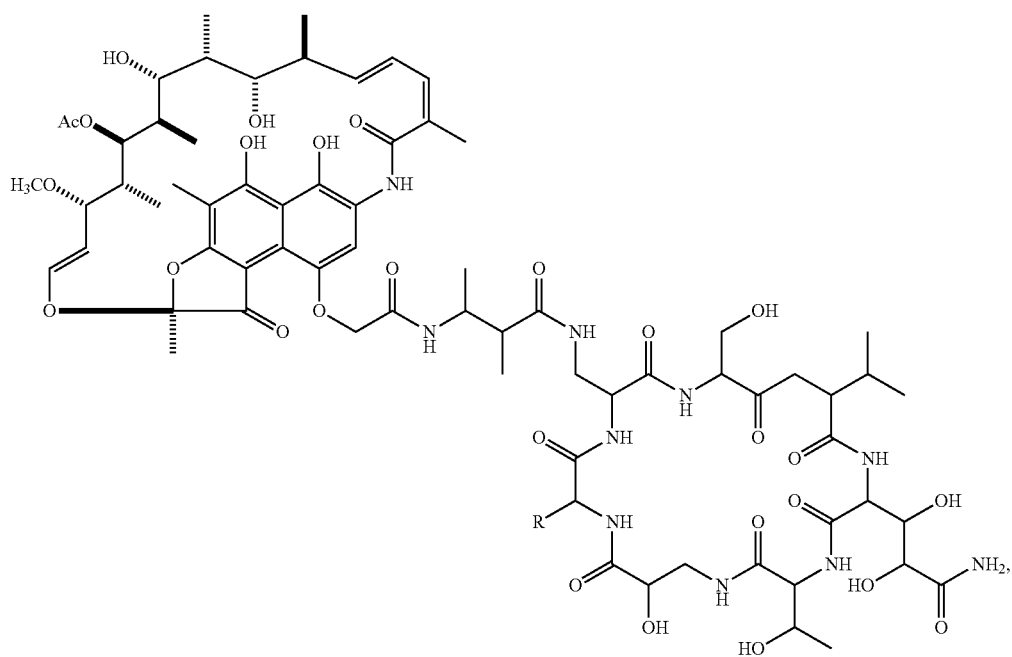

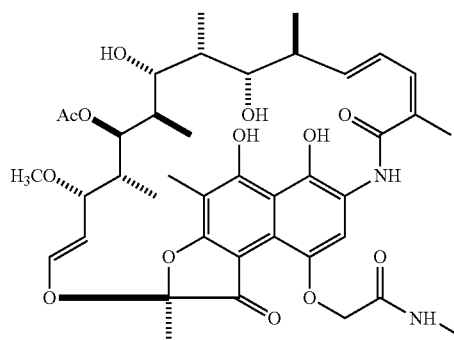
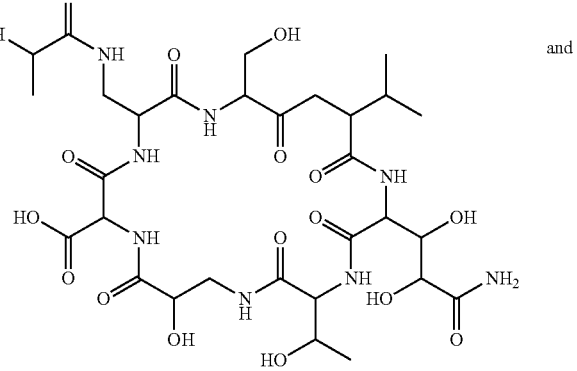
and
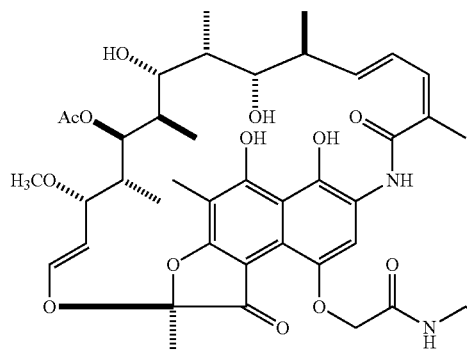
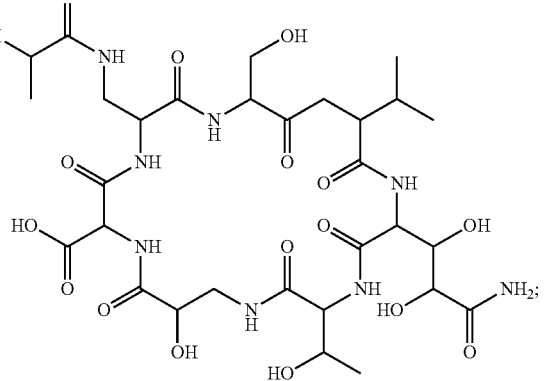
wherein R is H or COOH.

Certain embodiments of the invention provide a compound, or a salt thereof, selected from:
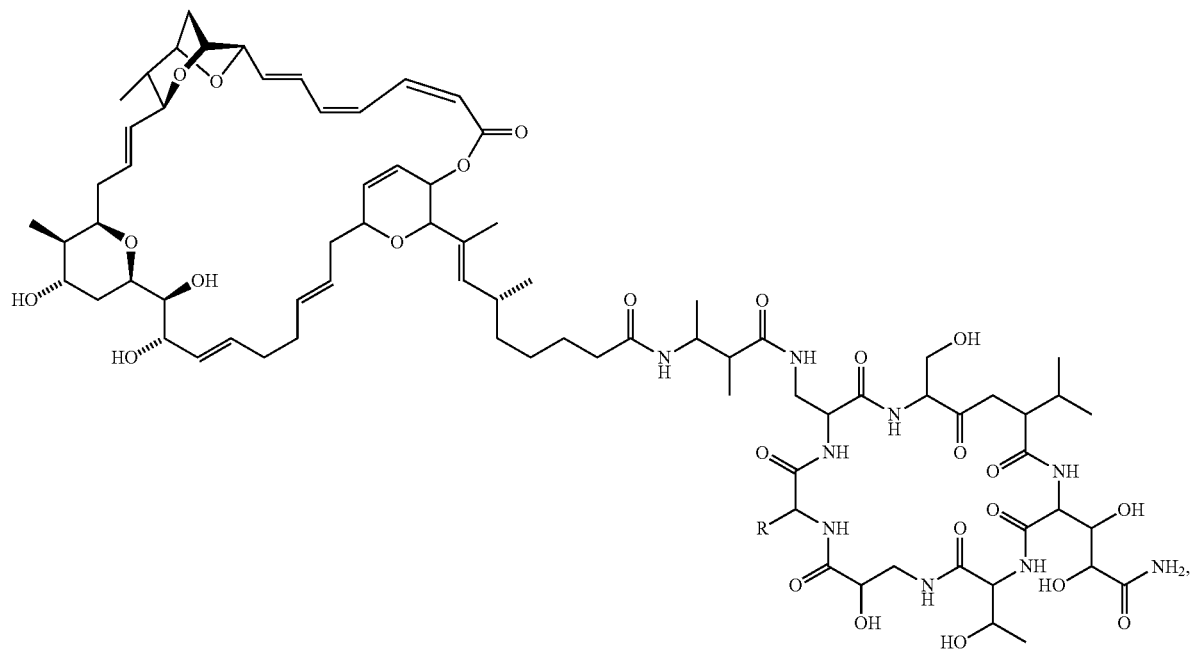
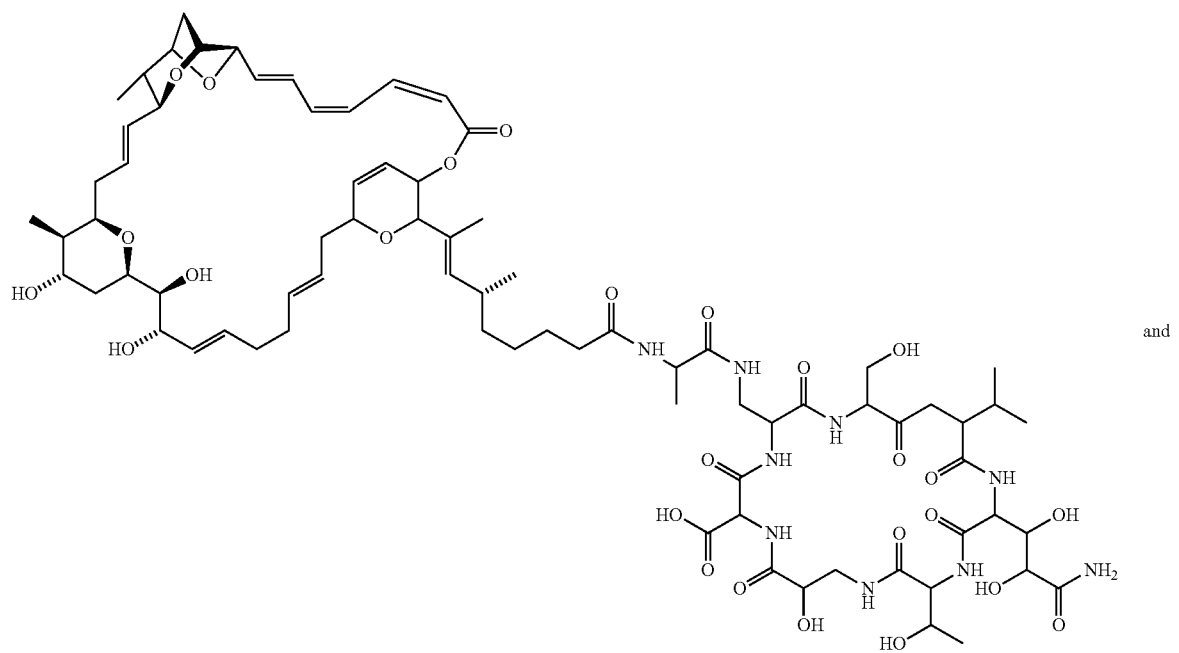
and -continued

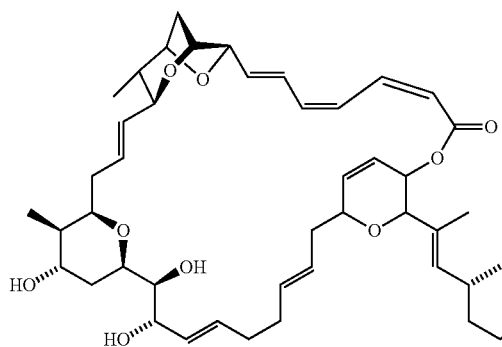 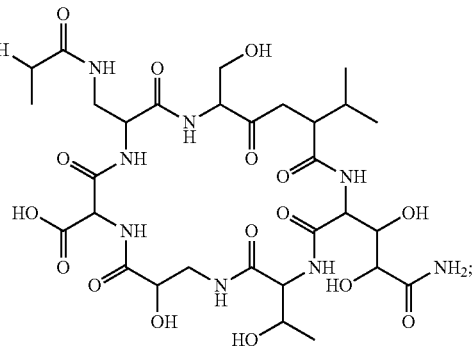

wherein R is H or COOH.

In certain embodiments, a compound of the invention binds to a bacterial RNA polymerase.

In certain embodiments, a compound of the invention binds to a bacterial RNA polymerase with an affinity higher than the affinity of X and the affinity of Y. In certain embodiments, compounds of the invention may exhibit equilibrium dissociation constants, Kds, equal to the product of the equilibrium dissociation constants of X and Y. In certain embodiments, a compound of the invention may have a Kd. of $\sim 10^{-17}$ to $10^{-18}$ M when X is rifampin and Y is GE23077.

In certain embodiments, a compound of the invention binds to a bacterial RNA polymerase resistant to at least one of X and Y.

In certain embodiments, a compound of the invention inhibits a bacterial RNA polymerase.

In certain embodiments, a compound of the invention inhibits a bacterial RNA polymerase with a potency higher than the potency of X and the potency of Y. In certain embodiments, compounds of the invention may exhibit half-maximal inhibitory concentrations, IC50s, equal to the product of the IC50s of X and Y. In certain embodiments, a compound of the invention may have an IC50 of $\sim 10^{-17}$ to $10^{-18}$ M when X is rifampin and Y is GE23077.

In certain embodiments of the invention, a compound of the invention inhibits a bacterial RNA polymerase resistant to at least one of X and Y.

In certain embodiments of the invention, a compound of the invention inhibits bacterial growth. In certain embodiments, a compound of the invention inhibits bacterial growth with potencies higher than the potency of X and the potency of Y. In certain embodiments, compounds of the invention may exhibit minimum inhibitory concentrations, MICs, equal to the product of the IC50s of the first moiety and the second moiety. In certain embodiments, a compound of the invention may have a MIC of $\sim 10^{-13}$ to $10^{-14}$ M when X is rifampin and Y is GE23077.

In certain embodiments of the invention, a compound of the invention is prepared from precursors X-α' and 'α-Y, wherein α' and 'α are moieties that can react to form α.

In certain embodiments of the invention a compound of the invention is prepared from precursors X-α' and 'α-Y in the presence of a bacterial RNA polymerase.

In certain embodiments, the bacterial RNA polymerase serves as a template for reaction of X-α' and 'α-Y.

Certain embodiments of the invention provide a method of making a compound of the invention, wherein the compound is prepared from precursors X-α' and 'α-Y, wherein α' and 'α are moieties that can react to form α.

In certain embodiments, one precursor contains an activated ester, an imidazolide, or an anhydride and the other precursor contains an amine.

In certain embodiments, one precursor contains a haloacetyl moiety and the other precursor contains an amine.

In certain embodiments, one precursor contains a halogen and the other precursor contains an amine.

In certain embodiments, one precursor contains a haloacetyl moiety and the other precursor contains a sulfhydryl.

In certain embodiments, one precursor contains a halogen and the other precursor contains a sulfhydryl.

In certain embodiments, one precursor contains a ketone or aldehyde and the other precursor contains an amine.

In certain embodiments, one precursor contains an azide and the other precursor contains an alkyne.

In certain embodiments, one precursor contains an azide and the other precursor contains a phosphine.

In certain embodiments, one precursor contains a boronic acid and the other precursor contains a substituted phenol.

In certain embodiments, one precursor contains phenylboronic acid and the other precursor contains salicylhydroxamic acid.

In certain embodiments, precursors X-α' and 'α-Y are allowed to react in the presence of a bacterial RNA polymerase.

In certain embodiments, the bacterial RNA polymerase serves as a template for reaction of X-α' and 'α-Y.

Certain embodiments provide a method of making a compound as described herein.

Certain embodiments provide the use a compound of the invention to bind to a bacterial RNA polymerase.

Certain embodiments provide the use of a compound of the invention to inhibit a bacterial RNA polymerase.

Certain embodiments provide the use of a compound of the invention to inhibit bacterial gene expression.

Certain embodiments provide the use of a compound of the invention to inhibit bacterial growth.

Certain embodiments provide the use of a compound of the invention to treat a bacterial infection.

Certain embodiments provide a composition comprising a compound of the invention or a pharmaceutically acceptable salt thereof, and a pharmaceutically acceptable vehicle.

Certain embodiments provide a method for inhibiting the growth of bacteria comprising contacting the bacteria with a compound of the invention, or a salt thereof.

Certain embodiments provide a method for inhibiting a bacterial RNA polymerase comprising contacting the bacterial RNA polymerase with a compound of the invention, or a salt thereof.

Certain embodiments provide a method for treating a bacterial infection in a mammal, e.g., a human, comprising administering to the mammal an effective amount of a compound of the invention, or a pharmaceutically acceptable salt thereof.

Certain embodiments provide a compound of the invention, or a pharmaceutically acceptable salt thereof, for use in the prophylactic or therapeutic treatment of a bacterial infection.

Certain embodiments provide the use of a compound of the invention, or a pharmaceutically acceptable salt thereof, for the preparation of a medicament for treating a bacterial infection in a mammal, e.g., a human.

In certain embodiments, the bacteria is selected from *Staphylococcus aureus* MSSA and MRSA, *Enterococcus faecalis*, *Enterococcus faecium*, *Acinetobacter baumannii*, and *Escherichia coli* D21f2tolC.

Certain embodiments provide a compound of the invention, or a pharmaceutically acceptable salt thereof, for use in medical treatment.

Figure 9:
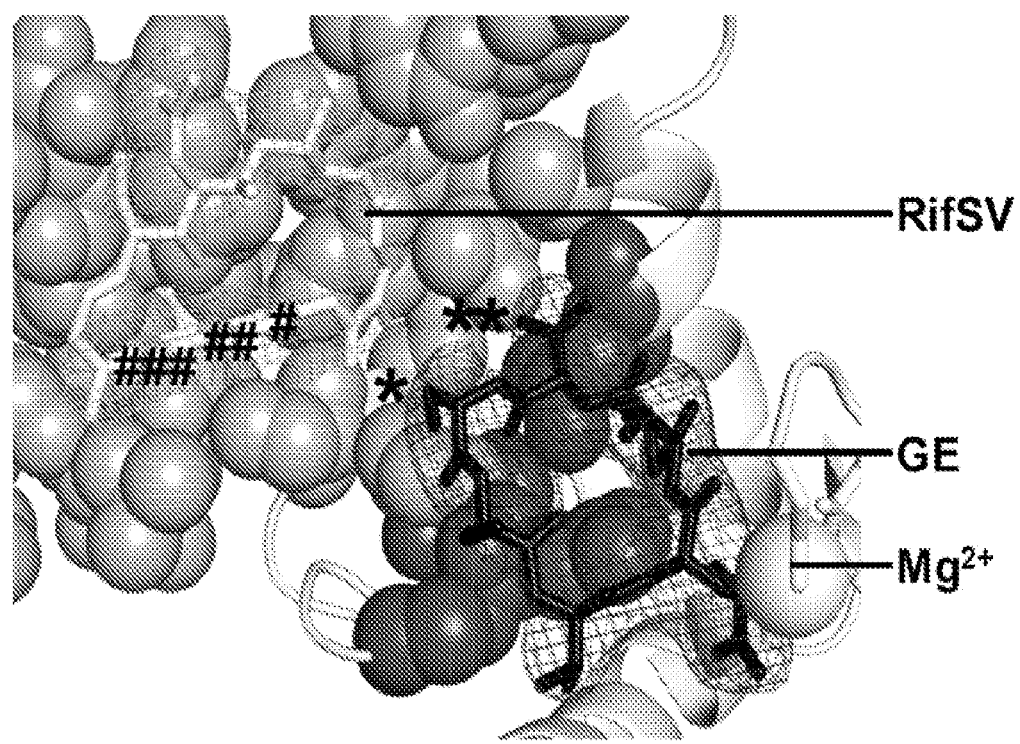
FIG. 9 shows a crystal structure of a complex containing RNAP, GE23077, and rifamycin SV (see Detailed Description of the Invention). The acyl-Apa and Ama residues of GE23077 are indicated as *, and **, respectively. GE23077 and rifamycin SV are in stick representations (black and white, respectively). Experimental electron densities for GE23077 and rifamycin SV are indicated as meshes ($F_o$-$F_c$ omit maps; dark gray and light gray, respectively). Sites of amino acid substitutions that confer GE23077-resistance and rifamycin-resistance are shown in van der Waals representations (dark gray and light gray, respectively). RNAP backbone atoms in and near the GE23077 and rifamycin binding sites are shown in a ribbon representation. The RNAP active-center $Mg^{2+}$ is shown as a sphere and is labelled. The C3, C4, and C11 of the rifamycin SV fused ring system are indicated as #, ##, and ###, respectively.

Rationale:

Applicant has identified the binding site on RNAP for GE23077 by the isolation and characterization of RNAP mutants resistant to GE23077 (FIGS. 3-5), by the determination of a crystal structure of a complex containing RNAP and GE23077 (FIG. 6), and by the determination of a crystal structure of a complex containing RNAP, GE23077, and a rifamycin (FIG. 9).

Figure 4:
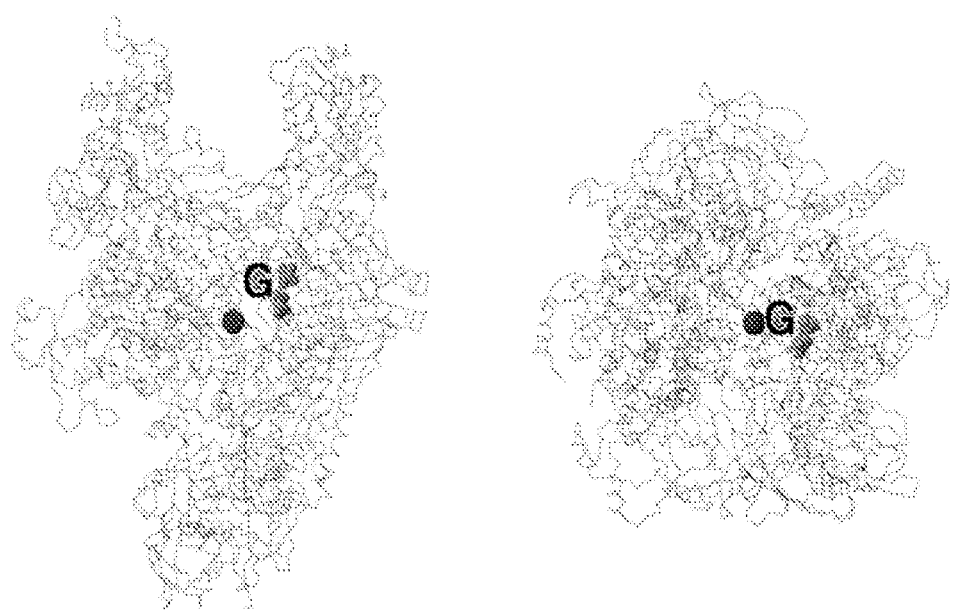
FIG. 4 shows the position of the GE23077 target within the three-dimensional structure of bacterial RNAP (two orthogonal views). Sites of amino acid substitutions that confer resistance to GE23077 are shown as a light gray solid surface (labelled "G"; see Detailed Description of the Invention). RNAP backbone atoms are shown in a Cα representation. The RNAP active-center $Mg^{2+}$ is shown as a sphere.
Figure 5:
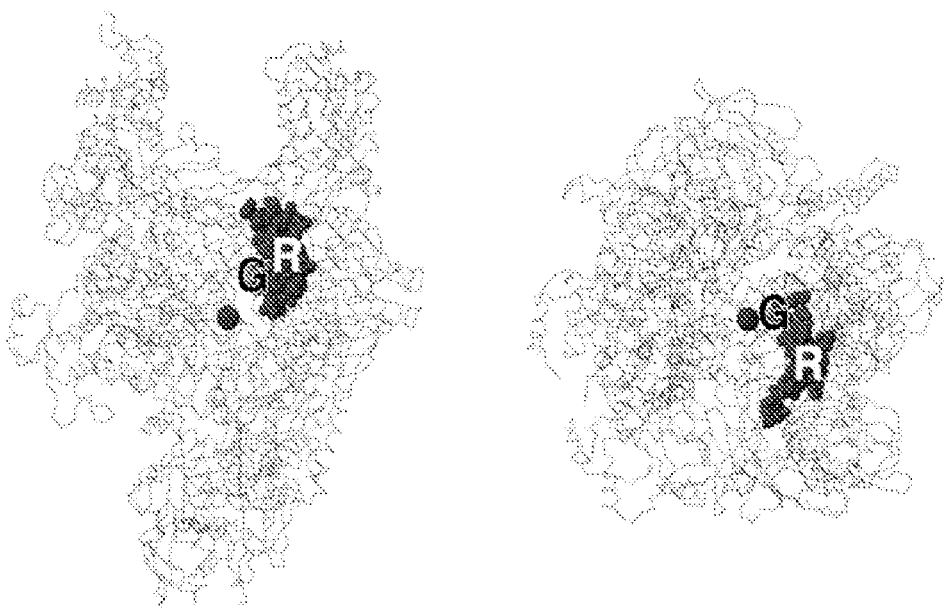
FIG. 5 shows the relationship between the Rif target and the GE23077 target within the three-dimensional structure of bacterial RNAP (two orthogonal views). Sites of amino acid substitutions that confer rifamycin-resistance are shown as a dark gray solid surface (labelled "R"; Ovchinnikov, Y., Monastyrskaya, G., Gubanov, V., Lipkin, V., Sverdlov, E., Kiver, I., Bass, I., Mindlin, S., Danilevskaya, 0., and Khesin, R. (1981) *Mol. Gen. Genet.* 184, 536-538; Ovchinnikov, Y., Monastyrskaya, G., Guriev, S., Kalinina, N., Sverdlov, E., Gragerov, A., Bass, I., Kiver, I., Moiseyeva, E., Igumnov, V., Mindlin, S., Nikiforov, V. and Khesin, R. (1983) *Mol. Gen. Genet.* 190, 344-348; Jin, D. J., and Gross, C. (1988) *J. Mol. Biol.* 202, 45-58; Severinov, K., Soushko, M., Goldfarb, A., and Nikiforov, V. (1993) *J. Biol. Chem.* 268, 14820-14825; Ho, M., Hudson, B., Das, K., Arnold, E. and Ebright, R. (2009) *Curr. Opin. Structl. Biol.* 19, 715-723). Sites of amino acid substitutions that confer resistance to GE23077 are shown as a light gray solid surface (labelled "G"; see Detailed Description of the Invention). RNAP backbone atoms are shown in a Cα representation. The RNAP active-center $Mg^{2+}$ is shown as a sphere.

Applicant has isolated and sequenced mutants of *Escherichia coli* RNAP resistant to GE23077 (FIGS. 3-5). Mutants were isolated by performing saturation mutagenesis of genes encoding RNAP subunits, introducing mutagenized genes into cells, plating cells on agar containing GE23077, and identifying clones able to grow in the presence of GE23077 (methods essentially as in Tuske, et al. (2005) *Cell* 122, 541-522; Temiaov, et al. (2005) *Mol. Cell* 19, 655-666; Mukhopadhyay, J., Das, K., Ismail, S., Koppstein, D., Jang, M., Hudson, B., Sarafianos, S., Tuske, S., Patel, J., Jansen, R., Irschik, H., Arnold, E., and Ebright, R. (2008) *Cell* 135, 295-307). Forty-nine independent mutants conferring moderate-to high-level GE23077-resistance (≥4-fold GE23077-resistance) were isolated and sequenced. Thirty-three were found to be single-substitution mutants. Six distinct single substitutions, affecting three sites in RNAP β subunit, were obtained: β Glu565→Asp, β Gly566→Cys, β Gly566→Arg, β Gly566→Ser, β Asn684→Lys, and β Asn684→Thr. In the three-dimensional structure of RNAP, the sites of the substitutions conferring GE23077-resistance, β residues 565, 566, and 684, are located adjacent to each other and form a compact determinant ("GE23077 target"; FIG. 4). The GE23077 target is located adjacent to the RNAP active center (FIG. 4). The GE23077 target also is located adjacent to, but does not substantially overlap, the RNAP Rif target (FIG. 5). Applicant concludes that the antibacterial activity of GE23077 requires a determinant on RNAP that comprises RNAP β subunit residues 565, 566, and 684 and that is located adjacent to the RNAP active center and the RNAP Rif target.

Applicant has prepared RNAP from GE23077-resistant mutants and has analyzed the inhibition of said RNAP by GE23077 in vitro and the binding to said RNAP by GE23077 in vitro (methods essentially as in Tuske, et al. (2005) *Cell* 122, 541-522; Temiaov, et al. (2005) *Mol. Cell* 19, 655-666; Mukhopadhyay, J., Das, K., Ismail, S., Koppstein, D., Jang, M., Hudson, B., Sarafianos, S., Tuske, S., Patel, J., Jansen, R., Irschik, H., Arnold, E., and Ebright, R. (2008) *Cell* 135, 295-307; Feklistov, A., Mekler, V., Jiang, Q., Westblade, L., Irschik, H., Jansen, R., Mustaev, A., Darst, S., and Ebright, R. (2008) *Proc. Natl. Acad. Sci. USA* 105, 14820-14825). RNAP prepared from GE23077-resistant mutants was found to be resistant to inhibition by GE23077 in vitro and to be defective in binding to GE23077 in vitro. Applicant concludes that the inhibition of RNAP by GE23077 requires the GE23077 target and that the binding of RNAP to GE23077 requires the GE23077 target. Applicant further concludes that the GE23077 target corresponds to the binding site on RNAP for GE23077.

This invention provides a GE23077 target that comprises RNAP β subunit residues 565, 566, and 684 (residues here and elsewhere in this section numbered as in *Escherichia coli* RNAP), that is required for the antibacterial activity of GE23077, that is required for the RNAP-inhibitory activity of GE23077, and that corresponds to the binding site on RNAP for GE23077.

Figure 6:
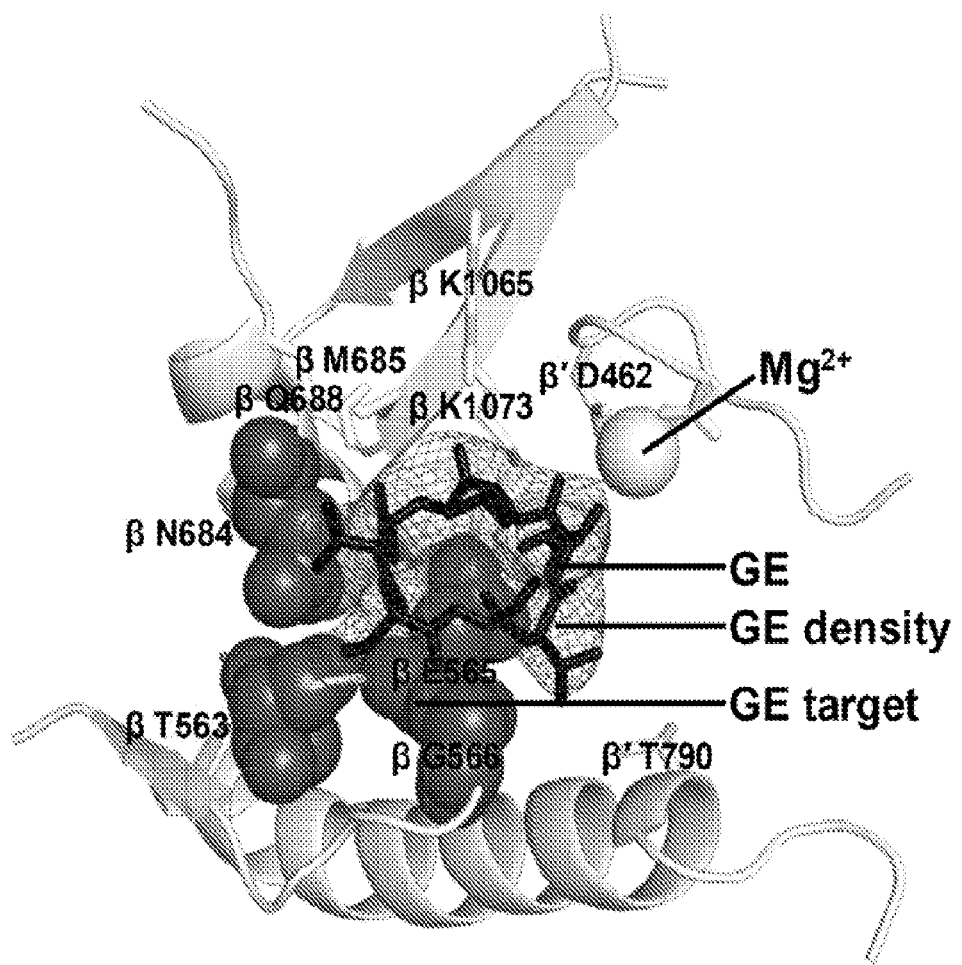
FIG. 6 shows a crystal structure of a complex containing RNAP and GE23077 (see Detailed Description of the Invention). GE23077 is shown in a stick representation (black). Experimental electron density for GE23077 is indicated as a mesh ($F_o$-$F_c$ omit map; dark gray). Sites of amino acid substitutions that confer GE23077-resistance are shown in a van der Waals representation (dark gray) and are labelled. Additional RNAP residues that contact GE23077 are shown in a stick representation and are labelled. RNAP backbone atoms in and near the GE23077 binding site are shown in a ribbon representation. The RNAP active-center $Mg^{2+}$ is shown as a sphere and is labelled. Residues are numbered as in *Escherichia coli* RNAP.

Applicant has determined a crystal structure of a complex containing RNAP and GE23077 (FIG. 6). Crystals were obtained by soaking GE23077 into pre-formed crystals of a complex of *Thermus thermophilus* RNAP $\sigma^4$ holoenzyme, a synthetic oligodeoxyribonucleotide duplex corresponding to single-stranded and downstream double-stranded DNA segments of an RNAP-promoter open complex, and a ribodinucleotide primer. X-ray diffraction data were collected at a synchrotron light source, the structure was solved by molecular replacement, using a previously determined structure of the same complex without GE23077 as the search model, and the structure was refined to a resolution of 3.3 Å and an $R_{free}$ of 0.195. The structure confirms that GE23077 target comprising RNAP β subunit residues 565, 566, and 684 corresponds to the binding site on RNAP for GE23077 (FIG. 6). GE23077 makes direct contacts with RNAP residues at which substitutions conferring moderate-to high-level GE2307-resistance are obtained: (RNAP β subunit residues 565, 566, and 684) (FIG. 6). GE23077 also makes direct contacts with adjacent RNAP residues (RNAP β subunit residues 563, 685, 688, 1065, and 1073; and RNAP β' subunit residues 462 and 790) and with the RNAP active-center $Mg^{2+}$ ion (FIG. 6).

The crystal structure shows that GE23077 makes direct contact with the RNAP active-center $Mg^{2+}$ ion (which is known to mediate phosphodiester-bond formation in transcription) and is close to, and may occlude, the RNAP active-center "i" and "i+1" sites (which are known to mediate binding of the first and second initiating ribonucleoside triphosphates in transcription initiation) (FIG. 6). Applicant concludes that GE23077 is positioned to interfere with one or more of the catalytic activity of the RNAP active-center $Mg^{2+}$ ion, the binding of the first initiating ribonucleoside triphosphate to the RNAP active-center "i" site, and the binding of the second initiating ribonucleoside triphosphate to the RNAP-active-center "i+1" site, and thereby to inhibit bacterial transcription, inhibit bacterial gene expression, and inhibit bacteria growth.

Figure 7:
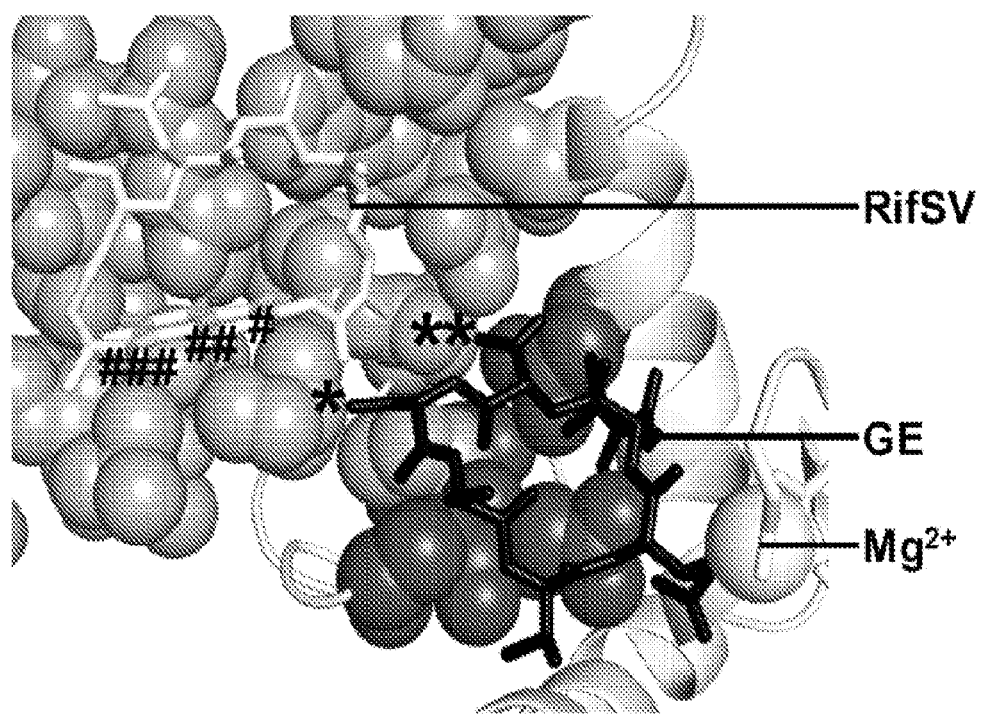
FIG. 7 shows a structural model of a complex containing RNAP, GE23077, and rifamycin SV, constructed based on crystal structures of a complex containing RNAP and GE23077 (FIG. 6; see Detailed Description of the Invention) and crystal structures of complexes containing RNAP and rifamycins (Campbell, et al. (2001) *Cell* 104, 901-912; Artsimovitch, et al. (2005) *Cell* 122, 351-363). GE23077 and rifamycin SV are in stick representations (black and white, respectively). Sites of amino acid substitutions that confer GE23077-resistance and rifamycin-resistance are shown in van der Waals representations (dark gray and light gray, respectively). RNAP backbone atoms in and near the GE23077 and rifamycin binding sites are shown in a ribbon representation. The RNAP active-center $Mg^{2+}$ is shown as a sphere and is labelled. The acyl-Apa and Ama residues of GE23077 are indicated as *, and **, respectively. The C3, C4, and C11 of the rifamycin SV fused ring system are indicated as #, ##, and ###, respectively.

The crystal structure shows that GE23077 binds to RNAP such that GE23077 is located immediately adjacent to, but does not substantially overlap, the RNAP Rif target (FIG. 7).

The crystal structure shows that the GE23077 binds to RNAP such that the acyl-Apa and Ama residues of GE23077 are the residues of GE23077 located closest to the RNAP Rif target (FIG. 7).

This invention provides a crystal structure of a complex containing RNAP and GE23077.

Applicant has constructed a structural model of a complex containing RNAP, GE23077, and rifamycin SV, starting from Applicant's crystal structures of a complex containing RNAP and GE23077 (FIG. 6) and published crystal structures of complexes containing RNAP and rifamycins (Campbell, et al. (2001) *Cell* 104, 901-912; Artsimovitch, et al. (2005) *Cell* 122, 351-363) (FIG. 7). The resulting structural model indicates that GE23077 and rifamycin SV are positioned to be able to interact with RNAP simultaneously, with no or minimal overlap and with no or minimal clash (FIG. 7). The structural model further indicates that, upon simultaneous binding of GE23077 and a rifamycin to RNAP, the acyl-Apa and Ama sidechains of GE23077 would be close to the C3, C4, and C11 atoms of the rifamycin (FIG. 7).

Figure 8:
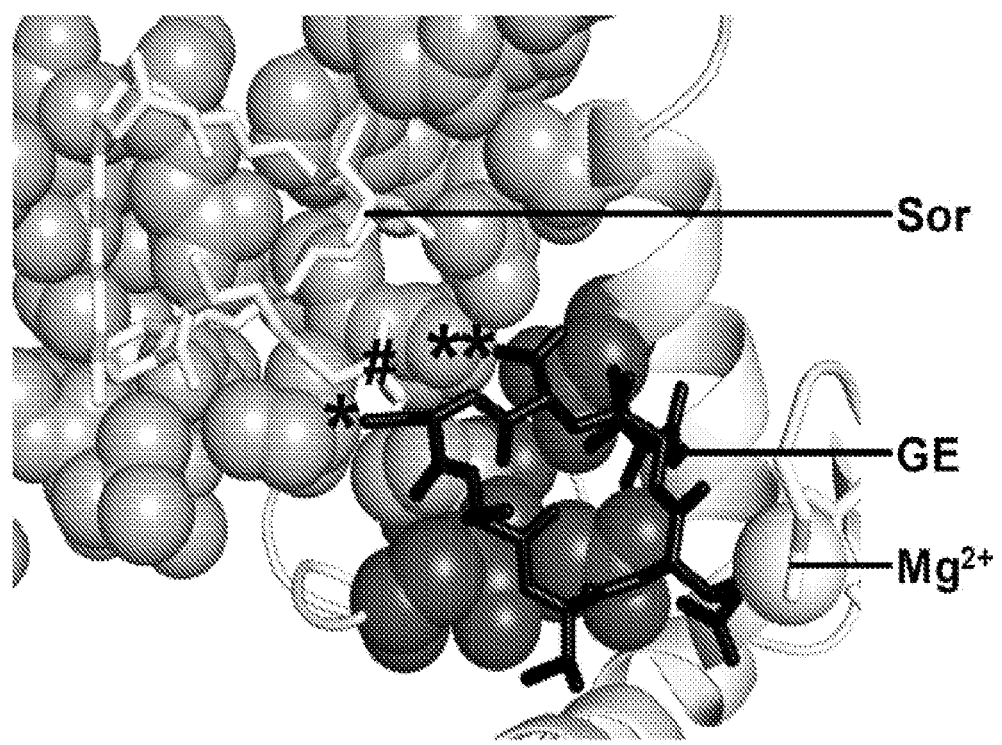
FIG. 8 shows a structural model of a complex containing RNAP, GE23077, and sorangicin A, constructed based on crystal structures of a complex containing RNAP and GE23077 (FIG. 6; see Detailed Description of the Invention) and a crystal structure of a complex containing RNAP and sorangicin A (Campbell, et al. (2005) *EMBO J* 24, 1-9). GE23077 and sorangicin A are in stick representations (black and white, respectively). Sites of amino acid substitutions that confer GE23077-resistance and rifamycin-resistance are shown in van der Waals representations (dark gray and light gray, respectively). RNAP backbone atoms in and near the GE23077 and rifamycin binding sites are shown in a ribbon representation. The RNAP active-center $Mg^{2+}$ is shown as a sphere and is labelled. The acyl-Apa and Ama residues of GE23077 are indicated as *, and **, respectively. The carboxyl carbon of the sorangicin A sidechain is indicated as #.

Applicant also has constructed a structural model of a complex containing P, GE23077, and sorangicin A, starting from Applicant's crystal structures of a complex containing RNAP and GE23077 (FIG. 6) and a published crystal structure of a complex containing RNAP and sorangicin A (Campbell, et al. (2005) *EMBO J.* 24, 1-9) (FIG. 8). The resulting structural model indicates that GE23077 and sorangicin A are positioned to be able to interact with RNAP simultaneously, with no or minimal overlap and with no or minimal clash (FIG. 8). The structural model further indicates that, upon simultaneous binding of GE23077 and a sorangicin to RNAP, the acyl-Apa and Ama sidechains of GE23077 would be close to the sidechain carboxyl carbon atom of the sorangicin (FIG. 8).

This invention provides a crystal-structure-derived structural model of a complex containing RNAP, GE23077, and a rifamycin, and a crystal-structure-derived structural model of a complex containing RNAP, GE23077, and a sorangicin.

Applicant subsequently determined a crystal structure of a complex containing RNAP, GE23077, and rifamycin SV (FIG. 9). Crystals were obtained by soaking GE23077 and rifamycin SV into pre-formed crystals of a complex of *Thermus thermophilus* RNAP $\sigma^4$ holoenzyme, a synthetic oligodeoxyribonucleotide duplex corresponding to single-stranded and downstream double-stranded DNA segments of an RNAP-promoter open complex, and a ribodinucleotide primer. X-ray diffraction data were collected at a synchrotron light source, the structure was solved by molecular replacement, using a previously determined structure of the same complex without GE23077 and rifamycin SV as the search model, and the structure was refined to a resolution of 3.4 Å and an $R_{free}$ of 0.227. The structure confirms that GE23077 and a rifamycin are able to bind to RNAP simultaneously (FIG. 9). The structure also confirms that, upon simultaneous binding of GE23077 and a rifamycin to RNAP, the acyl-Apa and Ama sidechains of GE23077 are close to the C3, C4, and C11 atoms of the rifamycin (FIG. 9).

This invention provides a crystal structure of a complex containing RNAP, GE23077, and rifamycin SV.

Figure 10:
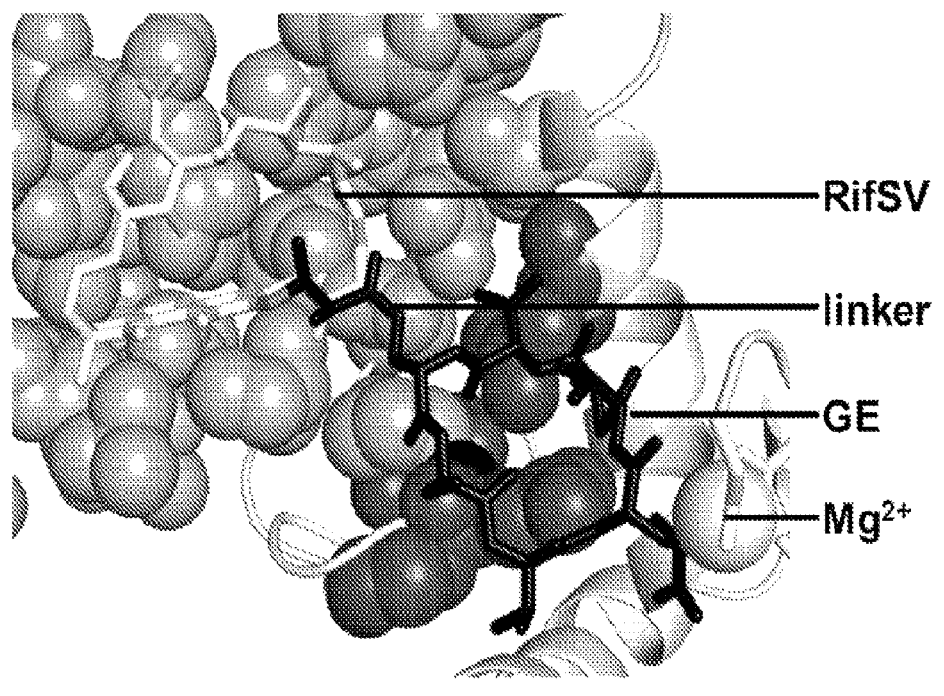

Applicant has constructed a structural model of a complex containing RNAP and a bipartite inhibitor of formula I in which the X moiety is rifamycin SV, the Y moiety is GE23077, and the α moiety is —NH— and connects C3 of the rifamycin SV fused ring system to Cζ1 of the GE23077 acyl-Apa sidechain (a "rifaGE"; FIG. 10). The structural model indicates that the bipartite inhibitor potentially can interact with RNAP through simultaneous interactions of the X moiety with the Rif target and the Y moiety with the GE23077 target. (FIG. 10).

Figure 11:
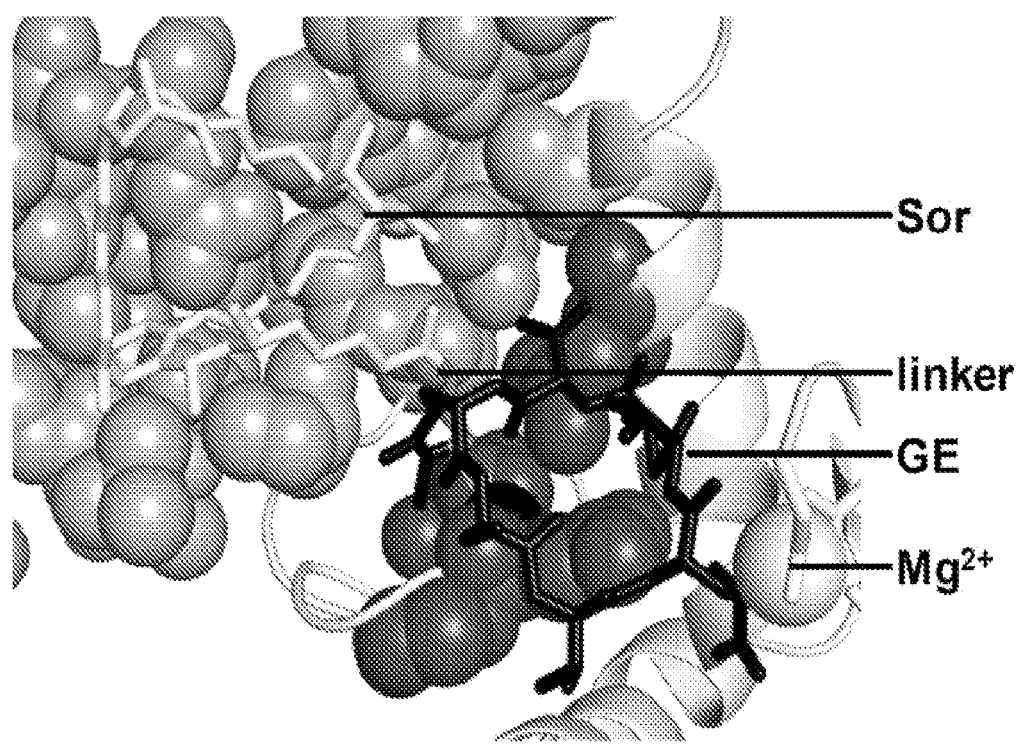
FIG. 11 shows a structural model of a complex containing RNAP and a representative bipartite inhibitor of this invention comprising sorangicin A linked to GE23077 ("soraGE"). In the bipartite inhibitor illustrated, the linker is —NHCH2CH2NH— and connects the carboxyl carbon of the sorangicin A sidechain to Cζ1 of the GE23077 acyl-Apa sidechain (compound 9). GE23077 and sorangicin A are in stick representations (black and white, respectively). Sites of amino acid substitutions that confer GE23077-resistance and rifamycin-resistance are shown in van der Waals representations (dark gray and light gray, respectively). RNAP backbone atoms in and near the GE23077 and rifamycin binding sites are shown in a ribbon representation. The RNAP active-center $Mg^{2+}$ is shown as a sphere and is labelled.

Applicant also has constructed a structural model of a complex containing RNAP and a bipartite inhibitor of formula I in which the X moiety is sorangicin A, the Y moiety is GE23077, and the α moiety is —NHCH2CH2NH— and connects the carboxyl carbon of the sorangicin A sidechain to Cζ1 of the GE23077 acyl-Apa sidechain (a "soraGE"; FIG. 11). The structural model indicates that the bipartite inhibitor potentially can interact with RNAP through simultaneous interactions of the X moiety with the Rif target and the Y moiety with the GE23077 target. (FIG. 11).

This invention provides a crystal-structure-derived structural model of a complex containing RNAP and a bipartite inhibitor comprising a rifamycin coupled to GE20377 (a rifaGE) and a crystal-structure-derived structural model of a complex containing RNAP and a bipartite inhibitor comprising a sorangicin coupled to GE23077 (a soraGE).

Based on the above-described findings, Applicant has hypothesized, and has confirmed by example, that the coupling of a first RNAP inhibitor that functions through the Rif target to a second RNAP inhibitor that functions through the GE23077 target can provide a bipartite inhibitor that interacts simultaneously with the Rif target and the GE23077 target and therefore that exhibits at least one of the following useful characteristics:
  (i) more potent inhibition of a bacterial RNAP than the individual first RNAP inhibitor and the individual second RNAP inhibitor;
  (ii) more potent antibacterial activity than the individual first RNAP inhibitor and the individual second RNAP inhibitor;
  (iii) potent inhibition of a bacterial RNAP resistant to one of the first RNAP inhibitor and the second RNAP inhibitor; and
  (iv) potent antibacterial activity against a bacterium resistant to one of the first RNAP inhibitor and the second RNAP inhibitor.

In particular, Applicant has hypothesized, and has confirmed by example, that the coupling of a one of a rifamycin, a streptovaricin, a tolypomycin, and a sorangicin to GE23077 or a GE23077 derivative can provide a bipartite inhibitor that interacts simultaneously with the Rif target and the GE23077 target and therefore that exhibits at least one of the following useful characteristics:
  (i) more potent inhibition of a bacterial RNAP than the individual first RNAP inhibitor and the individual second RNAP inhibitor;
  (ii) more potent antibacterial activity than the individual first RNAP inhibitor and the individual second RNAP inhibitor;
  (iii) potent inhibition of a bacterial RNAP resistant to one of the first RNAP inhibitor and the second RNAP inhibitor; and
  (iv) potent antibacterial activity against a bacterium resistant to one of the first RNAP inhibitor and the second RNAP inhibitor.

In particular, Applicant has hypothesized, and has confirmed by example, that the coupling of a one of a rifamycin, a streptovaricin, a tolypomycin, and a sorangicin to the residue corresponding to the acyl-Apa or Ama residue of GE23077 or a GE23077 derivative can provide a bipartite inhibitor that interacts simultaneously with the Rif target and the GE23077 target and therefore that exhibits at least one of the following useful characteristics:
  (i) more potent inhibition of a bacterial RNAP than the individual first RNAP inhibitor and the individual second RNAP inhibitor;
  (ii) more potent antibacterial activity than the individual first RNAP inhibitor and the individual second RNAP inhibitor;
  (iii) potent inhibition of a bacterial RNAP resistant to one of the first RNAP inhibitor and the second RNAP inhibitor; and
  (iv) potent antibacterial activity against a bacterium resistant to one of the first RNAP inhibitor and the second RNAP inhibitor.

In particular, Applicant has hypothesized, and has confirmed by example, that the coupling of a one of a rifamycin, a streptovaricin, a tolypomycin, and a sorangicin to the acyl-Apa residue of GE23077 or a GE23077 derivative can provide a bipartite inhibitor that interacts simultaneously with the Rif target and the GE23077 target and therefore that exhibits at least one of the following useful characteristics:
  (i) more potent inhibition of a bacterial RNAP than the individual first RNAP inhibitor and the individual second RNAP inhibitor;
  (ii) more potent antibacterial activity than the individual first RNAP inhibitor and the individual second RNAP inhibitor;

(iii) potent inhibition of a bacterial RNAP resistant to one of the first RNAP inhibitor and the second RNAP inhibitor; and
(iv) potent antibacterial activity against a bacterium resistant to one of the first RNAP inhibitor and the second RNAP inhibitor.

In particular, Applicant has hypothesized, and has confirmed by example, that the coupling of a one of a rifamycin, a streptovaricin, a tolypomycin, and a sorangicin to one of the residue corresponding to the acyl-Apa residue of GE23077 or a GE23077 derivative, through a linker comprising a chain of from 0 to about 15 consecutively bonded atoms, can provide a bipartite inhibitor that interacts simultaneously with the Rif target and the GE23077 target and therefore that exhibits at least one of the following useful characteristics:
(i) more potent inhibition of a bacterial RNAP than the individual first RNAP inhibitor and the individual second RNAP inhibitor;
(ii) more potent antibacterial activity than the individual first RNAP inhibitor and the individual second RNAP inhibitor;
(iii) potent inhibition of a bacterial RNAP resistant to one of the first RNAP inhibitor and the second RNAP inhibitor; and
(iv) potent antibacterial activity against a bacterium resistant to one of the first RNAP inhibitor and the second RNAP inhibitor.

In particular, Applicant has hypothesized, and has confirmed by example, that the coupling of a one of a rifamycin, a streptovaricin, a tolypomycin, and a sorangicin to one of the residue corresponding to the acyl-Apa residue of GE23077 or a GE23077 derivative, through a linker comprising a chain of from 0 to about 10 consecutively bonded atoms, can provide a bipartite inhibitor that interacts simultaneously with the Rif target and the GE23077 target and therefore that exhibits at least one of the following useful characteristics:
(i) more potent inhibition of a bacterial RNAP than the individual first RNAP inhibitor and the individual second RNAP inhibitor;
(ii) more potent antibacterial activity than the individual first RNAP inhibitor and the individual second RNAP inhibitor;
(iii) potent inhibition of a bacterial RNAP resistant to one of the first RNAP inhibitor and the second RNAP inhibitor; and
(iv) potent antibacterial activity against a bacterium resistant to one of the first RNAP inhibitor and the second RNAP inhibitor.

In particular, Applicant has hypothesized, and has confirmed by example, that the coupling of a one of a rifamycin, a streptovaricin, a tolypomycin, and a sorangicin to one of the residue corresponding to the acyl-Apa residue of GE23077 or a GE23077 derivative, through a linker comprising a chain of from 0 to about 10 consecutively bonded atoms, wherein said linker is designed based on a crystal-structure-derived structural model of a complex containing RNAP, a rifamycin, and GE23077 or of a complex containing RNAP, a sorangicin, and GE23077, can provide a bipartite inhibitor that interacts simultaneously with the Rif target and the GE23077 target and therefore that exhibits at least one of the following useful characteristics:
(i) more potent inhibition of a bacterial RNAP than the individual first RNAP inhibitor and the individual second RNAP inhibitor;
(ii) more potent antibacterial activity than the individual first RNAP inhibitor and the individual second RNAP inhibitor;
(iii) potent inhibition of a bacterial RNAP resistant to one of the first RNAP inhibitor and the second RNAP inhibitor; and
(iv) potent antibacterial activity against a bacterium resistant to one of the first RNAP inhibitor and the second RNAP inhibitor.

This invention provides a compound comprising a first RNAP inhibitor that functions through the Rif target coupled to a second RNAP inhibitor that functions through the GE23077 target.

This invention further provides a compound comprising one of a rifamycin, a streptovaricin, a tolypomycin, or a sorangicin coupled to GE23077 or a GE23077 derivative.

This invention further provides a compound comprising one of a rifamycin, a streptovaricin, a tolypomycin, or a sorangicin coupled to the acyl-Apa or Ama residue of GE23077 or a GE23077 derivative.

This invention further provides a compound comprising one of a rifamycin, a streptovaricin, a tolypomycin, or a sorangicin coupled to the acyl-Apa of GE23077 or a GE23077 derivative.

This invention further provides a compound comprising one of a rifamycin, a streptovaricin, a tolypomycin, or a sorangicin coupled to the acyl-Apa of GE23077 or a GE23077 derivative through a linker comprising a chain of from 0 to about 15 consecutively bonded atoms.

This invention further provides a compound comprising one of a rifamycin, a streptovaricin, a tolypomycin, or a sorangicin coupled to the acyl-Apa of GE23077 or a GE23077 derivative through a linker comprising a chain of from 0 to about 10 consecutively bonded atoms.

This invention further provides a compound comprising one of a rifamycin, a streptovaricin, a tolypomycin, or a sorangicin coupled to the acyl-Apa of GE23077 or a GE23077 derivative through a linker comprising a chain of from 0 to about 10 consecutively bonded atoms, wherein said linker is designed based on a crystal-structure-derived structural model of a complex containing RNAP, a rifamycin, and GE23077 or of a complex containing RNAP, a sorangicin, and GE23077.

Specific Embodiments Of The Invention

The present invention provides a compound that is a specific inhibitor of bacterial RNAP, the enzyme responsible for transcription. The compound has the structural formula:

$$X\text{-}\alpha\text{-}Y \qquad (I)$$

wherein X comprises a moiety that binds to the Rif target of a bacterial RNA polymerase, Y comprises a moiety that binds to GE23077 target of a bacterial RNA polymerase, and α is a linker. The invention has applications in control of bacterial gene expression, control of bacterial growth, antibacterial chemistry, and antibacterial therapy.

Figure 2:
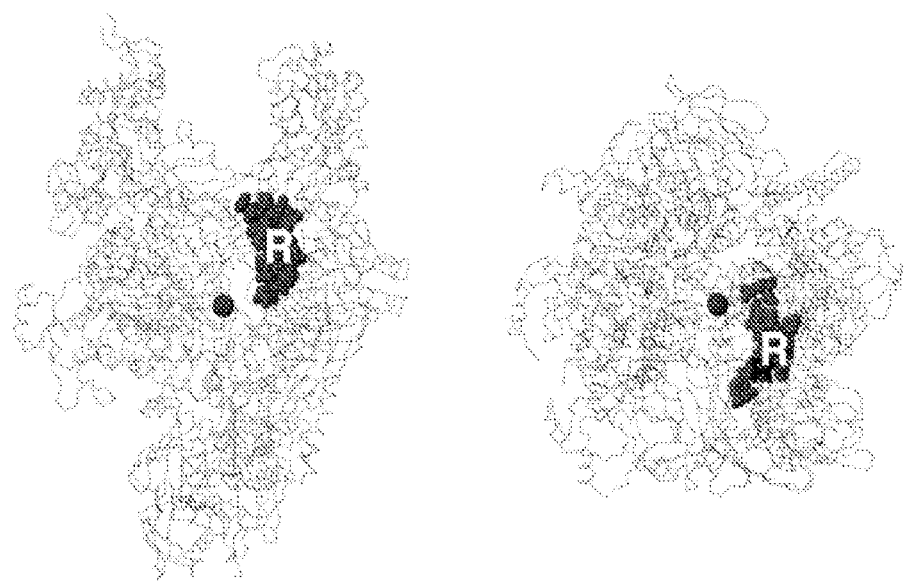
FIG. 2 shows the position of the Rif target within the three-dimensional structure of bacterial RNAP (two orthogonal views). Sites of amino acid substitutions that confer rifamycin-resistance are shown as a dark gray solid surface (labelled R; Ovchinnikov, Y., Monastyrskaya, G., Gubanov, V., Lipkin, V., Sverdlov, E., Kiver, I., Bass, I., Mindlin, S., Danilevskaya, O., and Khesin, R. (1981) *Mol. Gen. Genet.* 184, 536-538; Ovchinnikov, Y., Monastyrskaya, G., Guriev, S., Kalinina, N., Sverdlov, E., Gragerov, A., Bass, I., Kiver, I., Moiseyeva, E., Igumnov, V., Mindlin, S., Nikiforov, V. and Khesin, R. (1983) *Mol. Gen. Genet.* 190, 344-348; Jin, D. J., and Gross, C. (1988) *J. Mol. Biol.* 202, 45-58; Severinov, K., Soushko, M., Goldfarb, A., and Nikiforov, V. (1993) *J. Biol. Chem.* 268, 14820-14825; Ho, M., Hudson, B., Das, K., Arnold, E. and Ebright, R. (2009) *Curr. Opin. Structl. Biol.* 19, 715-723). RNAP backbone atoms are shown in a Cα representation. The RNAP active-center $Mg^{2+}$ is shown as a sphere.

X Moiety that Binds to the Rif Target of RNAP:

A region located within the RNAP active-center cleft—a region that comprises amino acids 146, 148, 507-509, 511-513, 516, 518, 522-523, 525-526, 529, 531-534, 568, 572, 574, and 687 of the RNAP β subunit in RNAP from *Escherichia coli*— is a useful target for compounds that inhibit transcription, including, by way of example, rifamycins, streptovaricins, tolypomycins, and sorangicins (Sensi, P., Maggi, N., Furesz, S, and Maffii, G. (1966) *Antimicrobial Agents Chemother* 6, 699-714; Rinehart (1972) *Accts. Chem. Res.* 5, 57-64; Wehrli (1977) *Topics Curr. Chem.* 72, 21-49; Campbell, et al. (2001) *Cell* 104, 901-912; Artsimovitch, et al. (2005) *Cell* 122, 351-363; Floss, et al. (2005) *Chem. Rev.* 105, 621-632; Aristoff, P., Garcia, G. A., Kirchoff, P. and Showalter, H. D. H. (2010) *Tuberculosis* 90, 94-118; Nitta, et al. (1968) *J. Antibiotics* 21, 521-522; Morrow, et al. (1979) *J. Bacteriol.* 137, 374-383; Kondo, et al. (1972) *J. Antibiotics* 25, 16-24; Rommelle, et al. (1990) *J. Antibiotics* 43, 88-91; O'Neill, et al. (2000) *Antimicrobial Agents Chemother.* 44, 3163-3166; Campbell, et al. (2005) *EMBO J.* 24, 1-9; Ho, M., Hudson, B., Das, K., Arnold, E. and Ebright, R. (2009) *Curr. Opin. Structl. Biol.* 19, 715-723; FIGS. 1,2). This region is referred to herein as the "Rif target," reflecting the fact that it serves as the binding site for rifamycins, among other compounds. The Rif target includes residues that are invariant or nearly invariant in RNAP from bacterial species, but that are radically different in RNAP from eukaryotic species (FIG. 1). The Rif target forms a shallow pocket within the wall of the RNAP active-center cleft (FIG. 2). A compound that binds to the Rif target of a bacterial RNAP can block bacterial RNA synthesis (e.g., by sterically blocking extension of RNA chains beyond a length of 2-3 nt), can inhibit bacterial gene expression, and can inhibit bacterial growth.

The Rif target referred to above in RNAP from *Escherichia coli* is similar in amino acid sequence in RNAP from most or all species of bacteria (FIG. 1). For example, amino acid residues 146, 148, 507-509, 511-513, 516, 518, 522-523, 525-526, 529, 531-534, 568, 572, 574, and 687 of the β subunit of RNAP from *Escherichia coli* exhibit high similarity to amino acid residues 135-137, 463-465, 467-469, 472, 474, 478-479, 481-482, 485, 487-490, 524, 526, and 645 of the β subunit of RNAP from *Bacillus subtilis* (FIG. 1). Thus, the discovery of a molecule that binds to the Rif target of, and inhibits RNA synthesis by, RNAP from *Escherichia coli* also is likely to bind to the Rif target of, and inhibit RNA synthesis by, RNAP from other species of bacteria. Therefore, molecules found to have antibacterial activity against *Escherichia coli* through binding to the Rif target and inhibiting RNA synthesis are likely to be found to have antibacterial activity against other species of bacteria.

In contrast, the Rif target differs radically in amino acid sequence between bacterial RNAP and eukaryotic RNAP, including human RNAP I, human RNAP II, and human RNAP III (FIG. 1). This allows for the identification of molecules that bind, in a Rif-target-dependent fashion, to a bacterial RNAP, but that do not bind, or that bind substantially less well, to a eukaryotic RNAP. This also allows for the identification of molecules that inhibit, in a Rif-target-dependent fashion, an activity of a bacterial RNAP, but that do not inhibit, or that inhibit substantially less well, an activity of a eukaryotic RNAP. This differentiation is important, because it permits the identification of bacterial-RNAP-selective binding molecules and bacteria-selective inhibitors.

Ligands that bind to the Rif target of, and inhibit RNA synthesis by, a bacterial RNAP are known in the art. Such ligands include, for example, rifamycins (a class of compounds that includes, for example, rifamycin SV, rifamycin S, rifamycin B, rifampin, rifapentine, and rifabutin), streptovaricins, tolypomycins, and sorangicins (Sensi, P., Maggi, N., Furesz, S, and Maffii, G. (1966) *Antimicrobial Agents Chemother.* 6, 699-714; Rinehart (1972) *Accts. Chem. Res.* 5, 57-64; Wehrli (1977) *Topics Curr. Chem.* 72, 21-49; Campbell, et al. (2001) *Cell* 104, 901-912; Artsimovitch, et al. (2005) *Cell* 122, 351-363; Floss, et al. (2005) *Chem. Rev.* 105, 621-632; Aristoff, P., Garcia, G. A., Kirchoff, P. and Showalter, H. D. H. (2010) *Tuberculosis* 90, 94-118; Nitta, et al. (1968) *J Antibiotics* 21, 521-522; Morrow, et al. (1979) *J. Bacteriol.* 137, 374-383; Kondo, et al. (1972) *J. Antibiotics* 25, 16-24; SOR: Rommelle, et al. (1990) *J. Antibiotics* 43, 88-91; O'Neill, et al. (2000) *Antimicrobial Agents Chemother.* 44, 3163-3166; Campbell, et al. (2005) *EMBO J.* 24, 1-9; Ho, M., Hudson, B., Das, K., Arnold, E. and Ebright, R. (2009) *Curr. Opin. Structl. Biol.* 19, 715-723). The references cited above are incorporated herein in their entirety.

The X moiety comprises an entity that binds to the Rif target of a bacterial RNAP.

The X moiety can be any ligand that binds to the Rif target of a bacterial RNAP.

In a preferred embodiment, the X moiety is selected from the group consisting of a rifamycin derivative, a streptovaricin derivative, a tolypomycin derivative, or a sorangicin derivative.

In a preferred embodiment, X is a rifamycin derivative.

When X is a rifamycin derivative, it is preferred that X is bonded to the α linker through the rifamycin fused ring system, most preferably, through at least one of the C3 atom, an atom pendant from the C3 atom, the C4 atom, an atom pendant from the C4 atom, the C11 atom, and an atom pendant from the C11 atom [representing atoms that, in the three-dimensional structures of RNAP-rifamycin complexes (see Campbell, et al. (2001) *Cell* 104, 901-912; Artsimovitch, et al. (2005) *Cell* 122, 351-363), are not involved in RNAP-rifamycin interactions and thus that can be functionalized without loss of RNAP-rifamycin interactions].

By way of example, when X is a rifamycin derivative, X can be bonded to the α linker though one of an amino linkage, a thioether linkage, and an iminomethylenyl linkage involving the rifamycin C3 atom. By way of further example, when X is a rifamycin derivative, X can be bonded to the α linker through a cyclo linkage involving the C3 and C4 atoms. By way of further example, when X is a rifamycin derivative, X can be bonded to the α linker through one of an ester linkage or an ether linkage involving O12, the oxygen atom pendent from the C4 atom of the rifamycin fused ring system. Methods of functionalization of the rifamycin C3, C4, and C11 atoms, and atoms pendant therefrom, are established and known in the art.

In another preferred embodiment, X is a streptovaricin derivative (wherein streptovaricins are a class of RNAP inhibitors structurally related to rifamycins).

When X is a streptovaricin derivative, it is preferred that X is bonded to the α linker through the streptovaricin fused ring system, most preferably, through at least one of the C3 atom, an atom pendant from the C3 atom, the C4 atom, and an atom pendant from the C4 atom [representing atoms that, by analogy to the three-dimensional structures of RNAP-rifamycin complexes (see Campbell, et al. (2001) *Cell* 104, 901-912; Artsimovitch, et al. (2005) *Cell* 122, 351-363), are expected not to be involved in RNAP-streptovaricin interactions and thus to be able to be functionalized without loss of RNAP-streptovaricin interactions].

In another preferred embodiment, X is a tolypomycin derivative (wherein tolypomycins are another class of RNAP inhibitors structurally related to rifamycins.

When X is a tolypomycin derivative, it is preferred that X is bonded to the α linker through the tolypomycin fused ring system, most preferably, through at least one of the C3 atom, an atom pendant from the C3 atom, the C4 atom, an atom pendant from the C4 atom, the C11 atom, and an atom pendant from the C11 atom [representing atoms that, by analogy to the three-dimensional structures of RNAP-rifamycin complexes (see Campbell, et al. (2001) *Cell* 104, 901-912; Artsimovitch, et al. (2005) *Cell* 122, 351-363) are expected not to be involved in RNAP-tolypomycin interactions and thus to be able to be functionalized without loss of RNAP-tolypomycin interactions].

In another preferred embodiment, X is a sorangicin derivative.

When X is a sorangicin derivative, it is preferred that X is bonded to the α linker through the sorangicin pendant sidechain group [corresponding to atoms C37-C45 and O10-O11 in sorangicin A, and representing a group that, in the three-dimensional structure of the RNAP-sorangicin-A complex (see Campbell, et al. (2005) *EMBO J.* 24, 1-9), is not involved in RNAP-sorangicin interactions and thus can be functionalized without loss of RNAP-sorangicin interactions].

Y Moiety that Binds to the GE23077 Target of RNAP:

Applicant has discovered that a second region located within the RNAP active-center cleft—a region that comprises amino acids 565, 566, and 684 of the RNAP β subunit in RNAP from *Escherichia coli*— is a useful target for compounds that inhibit transcription, including, by way of example, GE23077 and derivatives thereof (FIGS. 3-6). This region is referred to herein as the "GE23077 target," reflecting the fact that it serves as the binding site for GE23077, among other compounds. This region comprises residues that are invariant or nearly invariant in RNAP from bacterial species, and includes one residue that is different in RNAP from bacteria and RNAP from eukaryotic species (FIG. 3). This region is located adjacent to the RNAP active-center $Mg^{2+}$ ion (which mediates phosphodiester-bond formation in transcription) and the RNAP active-center "i" and "i+1" sites (which mediate binding of the first and second initiating ribonucleoside triphosphates in transcription initiation) (FIGS. 4-6). A compound that binds to this region of a bacterial RNAP can interfere with one or more of the catalytic activity of the RNAP active-center $Mg^{2+}$ ion, the binding of the first initiating ribonucleoside triphosphate to the RNAP active-center "i" site, and the binding of the second initiating ribonucleoside triphosphate to the RNAP-active-center "i+1" site, and thereby can inhibit bacterial transcription, can inhibit bacterial gene expression, and can inhibit bacterial growth.

The GE23077 target referred to above in RNAP from *Escherichia coli* is similar in amino acid sequence in RNAP from most or all other species of bacteria (FIG. 3). For example, amino acid residues 565, 566, and 684 of the β subunit of RNAP from *Escherichia coli* exhibit high similarity to amino acid residues 521, 522, and 642 of the β subunit of RNAP from *Bacillus subtilis* (FIG. 3). Thus, the discovery of a molecule that binds to the GE23077 target of, and inhibits RNA synthesis by, RNAP from *Escherichia coli* also is likely to bind to the GE23077 target of, and inhibit RNA synthesis by, RNAP from other species of bacteria. Therefore, molecules found to have antibacterial activity against *Escherichia coli* through binding to the GE23077 target and inhibiting RNA synthesis are likely to be found to have antibacterial activity against other species of bacteria.

In contrast, the GE23077 target referred to above includes one amino acid residue that is different in bacterial RNAP and eukaryotic RNAP, including human RNAP I, human RNAP II, and human RNAP III (FIG. 3). This allows for the identification of molecules that bind, in a GE23077-target-dependent fashion, to a bacterial RNAP, but that do not bind, or that bind substantially less well, to a eukaryotic RNAP. This also allows for the identification of molecules that inhibit, in a GE23077-target-dependent fashion, an activity of a bacterial RNAP, but that do not inhibit, or that inhibit substantially less well, an activity of a eukaryotic RNAP. This differentiation is important, because it permits the identification of bacterial-RNAP-selective binding molecules and bacteria-selective inhibitors.

The GE23077 target is different from the Rif target (FIGS. 1-5), and the proposed mechanism of inhibition of RNA synthesis by a compound that binds to the GE23077 target (interference with one or more of the catalytic activity of the RNAP active-center $Mg^{2+}$ ion, the binding of the first initiating ribonucleoside triphosphate to the RNAP active-center "i" site, and the binding of the second initiating ribonucleoside triphosphate to the RNAP-active-center "i+1" sit; see above) is different from the proposed mechanism of inhibition of RNA synthesis by a compound that bind to the rifamycin target (steric interference with extension of RNA products beyond a length of 2-3 nt; see Campbell, et al. (2001) *Cell* 104, 901-912; Feklistov, A., Mekler, V., Jiang, Q., Westblade, L., Irschik, H., Jansen, R., Mustaev, A., Darst, S., and Ebright, R. (2008) *Proc. Natl. Acad. Sci. USA* 105, 14820-14825).

In the three-dimensional structure of a bacterial RNAP, the GE23077 target is located immediately adjacent to, but does not substantially overlap, the Rif target (FIGS. 5-9).

This invention provides, by way of example only, a GE23077 target corresponding to, and alignable with, residues amino acids 565, 566, and 684 of the β subunit of RNAP from *Escherichia coli*, as well as with corresponding residues of the β subunit of RNAP from *Bacillus subtilis, Haemophilus influenzae, Vibrio cholerae, Pseudomonas aeruginosa, Treponema pallidum, Borrelia burgdorferi, Xylella fastidiosa, Campylobacter jejuni, Neisseria meningitidis, Rickettsia prowazekii, Thermotoga maritima, Chlamydia trachomatis, Mycoplasma pneumoniae, Staphylococcus aureus, Mycobacterium tuberculosis, Synechocystis* sp., *Aquifex aeolicus, Deinococcus radiodurans, Thermus thermophilus,* and *Thermus aquaticus* (FIG. 3).

The Y moiety comprises an entity that binds to the GE23077 target of a bacterial RNAP.

Therefore, the Y moiety comprises an entity that binds to at least one residue corresponding to, and alignable with, residues 565, 566, and 684 of the β subunit of RNAP from *Escherichia coli*, as well as with corresponding residues of the β subunits of RNA from *Bacillus subtilis, Haemophilus influenzae, Vibrio cholerae, Pseudomonas aeruginosa, Treponema pallidum, Borrelia burgdorferi, Xylella fastidiosa, Campylobacter jejuni, Neisseria meningitidis, Rickettsia prowazekii, Thermotoga maritima, Chlamydia trachomatis, Mycoplasma pneumoniae, Staphylococcus aureus, Mycobacterium tuberculosis, Synechocystis* sp., *Aquifex aeolicus, Deinococcus radiodurans, Thermus thermophilus,* and *Thermus aquaticus*.

In a preferred embodiment, the Y moiety comprises an entity that binds to the GE23077 target of a bacterial RNAP and interferes with at least one of the catalytic activity of the RNAP active-center $Mg^{2+}$ ion, the binding of the first initiating ribonucleoside triphosphate to the RNAP active-center "i" site, and the binding of the second initiating ribonucleoside triphosphate to the RNAP-active-center "i+1" site.

The Y moiety can be any ligand that binds to the GE23077 target of a bacterial RNAP.

Ligands that bind to the GE23077 target of a bacterial RNAP include, but are not limited to, GE23077 and GE23077 derivatives.

GE23077 is known in the art (see, for example, Ciciliato, I., Corti, E., Sarubbi, E., Stefanelli, S., Gastaldo, L., Montanini, N., Kurz, M., Losi, D., Marinelli, F., and Selva, E. (2004). *J. Antibiot.* 57, 210-217; Sarubbi, E., Monti, F., Corti, E., Miele, A., and Selva, E. (2004). *Eur. J. Biochem.* 271, 3146-3154; Marazzi, A., Kurz, M., Stefanelli, S., and Colombo, L. (2005). *J. Antibiot.* 58, 260-267; Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752; U.S. Pat. No. 6,586,393).

GE23077 is a natural-product complex isolated from the *Actinomadura* sp. The GE23077 natural-product complex comprises the individual components GE23077 A, GE23077 A1, GE23077 A2, GE23077 B, GE23077 B1, and GE23077 B2; these individual components differ in the structure of the acyl group of the acyl-Apa residue and/or in the stereochemistry of the Ama residue (see Ciciliato, I., Corti, E., Sarubbi, E., Stefanelli, S., Gastaldo, L., Montanini, N., Kurz, M., Losi, D., Marinelli, F., and Selva, E. (2004). *J. Antibiot.* 57, 210-217; Sarubbi, E., Monti, F., Corti, E., Miele, A., and Selva, E. (2004). *Eur. J. Biochem.* 271, 3146-3154; Marazzi, A., Kurz, M., Stefanelli, S., and Colombo, L. (2005). *J. Antibiot.* 58, 260-267; Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752; U.S. Pat. No. 6,586,39). Unless specified otherwise, the term "GE23077" when used herein is intended to encompass the GE23077 natural-product complex, GE23077 A, GE23077 A1, GE23077 A2, GE23077 B, GE23077 B1, and GE23077 B2.

GE23077 derivatives are known in the art (see, for example, Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752). GE23077 derivatives include, but are not limited to, GE23077 analogs having modifications to the acyl-ApA sidechain, GE23077 analogs having modifications to the Ama sidechain, and GE23077 analogs having modifications to the Dhg sidechain (Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752).

In a preferred embodiment, Y is GE23077.

In another preferred embodiment, Y is a GE23077 derivative that binds to the GE23077 target. Such derivatives include, but are not limited to, analogs of GE23077 having modifications to the acyl-Apa sidechain, analogs having modifications to the Ama sidechain, and analogs having modifications to the Dhg sidechain (see Marazzi, A., Vannini, A., Patel, D., White, R. and Ciabatti, R. (2005) *Bioorg. Med. Chem.* 15, 3748-3752).

In some preferred embodiments, Y is a GE23077 derivative in which the acyl group of the GE23077 acyl-Apa sidechain is shortened (see Marazzi, A., Vannini, A., Patel, D., White, R. and Ciabatti, R. (2005) *Bioorg. Med. Chem.* 15, 3748-3752).

In some preferred embodiments, Y is a GE23077 derivative in which the acyl group of the GE23077 acyl-Apa sidechain is removed.

In some preferred embodiments, Y is a GE23077 A derivative in which the olefin in the acyl group of the GE23077 A acyl-Apa sidechain is reduced.

In some preferred embodiments, Y is a GE23077 derivative in which the Ama sidechain is decarboxylated ("descarboxy-GE23077"; see Marazzi, A., Vannini, A., Patel, D., White, R. and Ciabatti, R. (2005) *Bioorg. Med. Chem.* 15, 3748-3752).

In some preferred embodiments, Y is a GE23077 derivative in which the Ama sidechain is esterified (see Marazzi, A., Vannini, A., Patel, D., White, R. and Ciabatti, R. (2005) *Bioorg. Med. Chem.* 15, 3748-3752).

In some preferred embodiments, Y is a GE23077 derivative in which the Ama sidechain is replaced by a Glu sidechain (see Marazzi, A., Vannini, A., Patel, D., White, R. and Ciabatti, R. (2005) *Bioorg. Med. Chem.* 15, 3748-3752).

α Linker:

α is a linker that links the X moiety that binds to the Rif target of a bacterial RNAP and the Y moiety that binds to GE23077 target of a bacterial RNAP. The linker preferably has a length of from about 0 Å to about 15 Å (representing a length suitable to connect a moiety bound to the Rif target of a bacterial RNAP and a moiety bound to the GE23077 target of a bacterial RNAP; FIGS. 5 and 7-11).

The linker may contain exclusively covalent bonds. Alternatively, the linker may contain a coordinate-covalent bond.

Preferably, the linker does not substantially interfere with the individual interactions between the X moiety and the Rif target of a bacterial RNAP and between the Y moiety and the GE23077 target of a bacterial RNAP.

Preferably, the linker does not substantially interfere with simultaneous interactions between the X moiety and the Rif target of a bacterial RNAP and between the Y moiety and the GE23077 target of a bacterial RNAP.

Optionally, the linker makes a favorable interaction with at least one residue of RNAP located between the Rif target and the GE23077 target.

Bipartite Inhibitors of RNAP:

The invention provides, solely by way of example, bipartite inhibitors comprising a rifamycin moiety, a GE23077 moiety, and a covalent linker. Such a bipartite inhibitor is referred to herein as "rifaGE" (rifamycin-GE23077; FIG. 10).

The invention also provides, solely by way of example, bipartite inhibitors comprising a sorangicin moiety, a GE23077 moiety, and a covalent linker. Such a bipartite inhibitor is referred to herein as "soraGE" (sorangicin-GE23077; FIG. 11).

Applicant has found that the rifaGE having the formula {rifamycin SV}—NH-{descarboxy-GE23077}, wherein the —NH— linker connects the C3 of the rifamycin SV fused ring system to Cζ1 of the descarboxy-GE23077 acyl-Apa sidechain (compound 3), inhibits a rifamycin-resistant derivative of *Escherichia coli* RNAP—[Asn516]β RNAP— with a potency 80 times higher than the potency of rifamycin SV (IC$_{50}$=0.15 μM vs. IC$_{50}$=12 μM; Table 1).

Applicant further has found that the above-referenced rifaGE inhibits a GE23077-resistant derivative of *Escherichia coli* RNAP—[Asp565]β RNAP—with a potency >5,000 times higher than the potency of GE23077 (IC$_{50}$=0.02 μM vs. IC$_{50}$=>100 μM; Table 2).

Applicant further has found that the above-referenced rifaGE exhibits potent antibacterial activity against *Staphylococcus aureus, Enterococcus faecalis, Acinetobacter baumannii*, and *Escherichia coli* D21f2tolC (MICs=0.05, 6, 10, and 2 μg/ml, respectively; Table 3).

Method of Preparing Bipartite Inhibitors of RNAP:

The invention also provides a method of preparing a compound having a structural formula (I):

X-α-Y    (I)

wherein X comprises a moiety that binds to the Rif target of a bacterial RNA polymerase, Y comprises a moiety that binds to the GE23077 target of a bacterial RNA polymerase, and α is a linker.

The method includes providing precursors X-α' and 'α-Y, and reacting moieties α' and 'α to form α.

The precursors may include any suitable precursors that will bind to form a linker moiety and permit the X moiety to bind to the Rif target of the RNAP and permit the Y moiety to bind to the GE23077 target of the RNAP.

For example, in a preferred embodiment, one precursor contains an activated ester, an imidazolide, or an anhydride and the other precursor contains an amine. In another preferred embodiment, one precursor contains a halogen and the other precursor contains an amine. In another preferred embodiment, one precursor contains a halogen and the other precursor contains a sulfhydryl. In another preferred embodiment, one precursor contains a ketone or aldehyde and the other precursor contains an amine. In another preferred embodiment, one precursor contains an azide and the other precursor contains an alkyne. In another preferred embodiment, one precursor contains an azide and the other precursor contains a phosphine. In another preferred embodiment, one precursor contains a boronic acid and the other precursor contains a substituted phenol. In another preferred embodiment, one precursor contains phenylboronic acid and the other precursor contains salicylhydroxamic acid.

Each of the above-referenced chemistries are established and are known to those skilled in the art (see Rostovetsev, et al. (2002) *Angew. Chem. Int. Ed.* 41, 2596-2599 Wang, et al. (2003) *J. Amer. Chem. Soc.* 125, 3192-3193; Breibauer, et al. (2003) *ChemBioChem.* 4, 1147-1149; Saxon, et al. (2000) *Science* 287, 2007-2010; Kiick, et al. (2002), *Proc. Natl. Acad. Sci. USA* 99, 19-24; Kohn, et al. (2004) *Angew. Chem. Int. Ed.* 43, 3106-3116; Stolowitz, et al. (2001) *Bioconj. Chem.* 12, 229-239; Wiley, et al. (2001), 12, 240-250).

In one embodiment, moieties α' and 'α of precursors X-α' and 'α-Y are reacted in the absence of a bacterial RNA polymerase.

In another embodiment, moieties α' and 'α of precursors X-α' and 'α-Y are reacted in the presence of a bacterial RNA polymerase. In this embodiment, the bacterial RNA polymerase potentially can serve as a template for reaction of X-α' and 'α-Y.

By way of example, the rifaGEs having the formulas {rifamycin S}—NH-{descarboxy-GE23077} and {rifamycin SV}—NH-{descarboxy-GE23077}, wherein the —NH— linker connects the C3 atom of the rifamycin fused ring system to the Cζ1 atom of the descarboxy-GE23077 acyl-Apa sidechain, can be prepared by reacting 3-bromo-rifamycin S (prepared as in U.S. Pat. No. 4,179,438) with H2N-{descarboxy-GE23077}, wherein the HN2-is bonded to the Cζ1 atom of the descarboxy-GE23077 acyl-Apa sidechain (prepared as in Scheme 1a, R═H) (Scheme 2a, R═H; Example 1, compounds 2 and 3).

By way of further example, the rifaGEs having the formulas {rifamycin S}—NH-{GE23077} and {rifamycin SV}—NH-{GE23077}, wherein the —NH— linker connects the C3 atom of the rifamycin fused ring system to the Cζ1 atom of the GE23077 acyl-Apa sidechain, can be prepared by reacting 3-bromo-rifamycin S (prepared as in U.S. Pat. No. 4,179,438) with H2N-{GE23077}, wherein the HN2-is bonded to the Cζ1 atom of the GE23077 acyl-Apa sidechain (prepared as in Scheme 1a, R=COOH) (Scheme 2a, R=COOH).

By way of further example, the rifaGEs having the formulas {rifamycin S}—NH-{GE23077} and {rifamycin SV}—NH-{GE23077}, wherein the —NH— linker connects the C3 atom of the rifamycin fused ring system to the Cε atom of the GE23077 acyl-Apa sidechain, can be prepared by reacting 3-bromo-rifamycin S (prepared as in U.S. Pat. No. 4,179,438) with H2N-{GE23077}, wherein the HN2-is bonded to the Cε atom of the GE23077 acyl-Apa sidechain (prepared as in Scheme 1b; Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752) (Scheme 2b).

By way of further example, the rifaGEs having the formulas {rifamycin S}—NHCH2CH2NH-{GE23077} and {rifamycin SV}—NHCH2CH2NH-{GE23077}, wherein the —NHCH2CH2NH— linker connects the C3 atom of the rifamycin fused ring system to the Cε atom of the GE23077 acyl-Apa sidechain, can be prepared by reacting 3-bromo-rifamycin S (prepared as in U.S. Pat. No. 4,179,438) with H2NCH2CH2NH-{GE23077}, wherein the H2NCH2CH2NH— is bonded to the Cε atom of the GE23077 acyl-Apa sidechain (prepared as in Scheme 1c) (Scheme 2c).

By way of further example, the rifaGE having the formula {rifamycin SV}—{CH2C(O)NH}-{descarboxy-GE23077}, wherein the —{CH2C(O)NH}— linker connects the oxygen atom pendant from the C4 atom of the rifamycin fused ring system to the Cζ1 atom of the descarboxy-GE23077 acyl-Apa sidechain, can be prepared by reacting an activated ester of rifamycin B (prepared as in Sensi, P., Maggi, N., Ballotta, R., Fueresz, S., Pallanza, R. and Arioli, V. (1964) *J. Med. Chem.* 53, 596-602) with H2N-{descarboxy-GE23077}, wherein the HN2-is bonded to the Cζ1 atom of the descarboxy-GE23077 acyl-Apa sidechain (prepared as in Scheme 1a, R=H) (Scheme 3a, R=H; Example 2, compound 4).

By way of further example, the rifaGE having the formula {rifamycin SV}-{CH2C(O)NH}-{GE23077}, wherein the —{CH2C(O)NH}— linker connects the oxygen atom pendant from the C4 atom of the rifamycin fused ring system to the Cζ1 atom of the GE23077 acyl-Apa sidechain, can be prepared by reacting an activated ester of rifamycin B (prepared as in Sensi, P., Maggi, N., Ballotta, R., Fueresz, S., Pallanza, R. and Arioli, V. (1964) *J. Med. Chem.* 53, 596-602) with H2N-{GE23077}, wherein the HN2-is bonded to the Cζ1 atom of the GE23077 acyl-Apa sidechain (prepared as in Scheme 1a, R=COOH) (Scheme 3a, R=COOH).

By way of further example, the rifaGE having the formula {rifamycin SV}—{CH2C(O)NH}-{GE23077}, wherein the —{CH2C(O)NH}— linker connects the oxygen atom pendant from the C4 atom of the rifamycin fused ring system to the Cε atom of the GE23077 acyl-Apa sidechain, can be prepared by reacting an activated ester of rifamycin B (prepared as in Sensi, P., Maggi, N., Ballotta, R., Fueresz, S., Pallanza, R. and Arioli, V. (1964) *J. Med. Chem.* 53, 596-602) with H2N-{GE23077}, wherein the HN2-is bonded to the Cε atom of the GE23077 acyl-Apa sidechain (prepared as in Scheme 1b; Mariani, R., Granata, G., Maffioli, S., Selina, S., Brunati, C., Sosio, M., Marazzi, A., Vannini, A., Patel, D., White, R. and Ciabatti, R. (2005) *Bioorg. Med. Chem.* 15, 3748-3752) (Scheme 3b).

By way of further example, the rifaGE having the formula {rifamycin SV}—{CH2C(O)NHCH2CH2NH}-{GE23077}, wherein the —{CH2C(O)NHCH2CH2NH}— linker connects the oxygen atom pendant from the C4 atom of the rifamycin fused ring system to Cε of the GE23077 acyl-Apa sidechain, can be prepared by reacting an activated ester of rifamycin B (prepared as in Sensi, P., Maggi, N., Ballotta, R., Fueresz, S., Pallanza, R. and Arioli, V. (1964) *J. Med. Chem.* 53, 596-602) with H2NCH2CH2NH-{GE23077}, wherein the HN2CH2CH2NH— is bonded to the Cε atom of the GE23077 acyl-Apa sidechain (prepared as in Scheme 1c) (Scheme 3c; Example 3, compound 7).

By way of further example, the soraGE having the formula {sorangicin A}-NH-{descarboxy-GE23077}, wherein the —NH— linker connects the carbon atom of the carboxyl group of the sorangicin sidechain to the Cζ1 atom of the descarboxy-GE23077 acyl-Apa sidechain, can be prepared by reacting an imidazolide of sorangicin A (prepared as in Jansen, R., Schummer, D., Irschik, H. and Hofle, G. (1990) *Liebigs Ann. Chem.* 10, 975-988) with H2N-{descarboxy-GE23077}, wherein the H2N— is bonded to the Cζ1 atom of the descarboxy-GE23077 acyl-Apa sidechain (prepared as in Scheme 1a) (Scheme 4a, R=H).

By way of further example, the soraGE having the formula {sorangicin A}-NH-{GE23077}, wherein the —NH— linker connects the carbon atom of the carboxyl group of the sorangicin sidechain to the Cζ1 atom of the GE23077 acyl-Apa sidechain, can be prepared by reacting an imidazolide of sorangicin A (prepared as in Jansen, R., Schummer, D., Irschik, H. and Hofle, G. (1990) *Liebigs Ann. Chem.* 10, 975-988) with H2N-{GE23077}, wherein the H2N— is bonded to the Cζ1 atom of the GE23077 acyl-Apa sidechain (prepared as in Scheme 1a) (Scheme 4a, R=COOH).

By way of further example, the soraGE having the formula {sorangicin A}-NH-{GE23077}, wherein the —NH— linker connects the carbon atom of the carboxyl group of the sorangicin sidechain to the Cε atom of the GE23077 acyl-Apa sidechain, can be prepared by reacting an imidazolide of sorangicin A (prepared as in Jansen, R., Schummer, D., Irschik, H. and Hofle, G. (1990) *Liebigs Ann. Chem.* 10, 975-988) with H2N-{GE23077}, wherein the H2N— is bonded to the Cε atom of the GE23077 acyl-Apa sidechain (prepared as in Scheme 1b; Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752) (Scheme 4b).

By way of further example, the soraGE having the formula {sorangicin A}-NHCH2CH2NH-{GE23077}, wherein the —NHCH2CH2NH— linker connects the carbon atom of the carboxyl group of the sorangicin sidechain to the Cε atom of the GE23077 acyl-Apa sidechain, can be prepared by reacting H2NCH2CH2NH-{sorangicin A}, wherein the HN2CH2CH2NH— is bonded to the carbon atom of the sorangicin sidechain (prepared by procedures in Jansen, R., Schummer, D., Irschik, H. and Hofle, G. (1990) Liebigs Ann. Chem. 10, 975-988), with O={GE23077}, wherein the O= is bonded to the Cε atom of the GE23077 acyl-Apa sidechain (prepared as in Scheme 1b; Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752), followed by treating with sodium cyanoborohydride (Scheme 4c; Example 4, compound 9).

Scheme 1 below illustrates examples of synthetic routes to introduce an amine into the GE23077 acyl-Apa sidechain. Panel (A) illustrates an example of a synthesis of H2N-{descarboxy-GE23077} and H2N-{GE23077}, wherein the HN2-is bonded to the atom of the descarboxy-GE23077 or GE23077 acyl-Apa sidechain, involving the aza-Michael addition of NH2-to GE23077 A. Panel (B) illustrates an example of a synthesis of H2N-{GE23077}, wherein the HN2-is bonded to the Cε atom of the GE23077 acyl-Apa sidechain, involving the ozonolysis of GE23077 A, Schiffs base formation with benzyl amine and, debenzylation (procedures as in Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752). Panel (C) illustrates an example of a synthesis of H2NCH2CH2NH-{GE23077}, wherein the HN2CH2CH2NH— is bonded to the Cε atom of the GE23077 acyl-Apa sidechain, involving the ozonolysis of GE23077 A, Schiffs base formation with trityl-NHCH2CH2NH2, and detritylation (procedures analogous to procedures in Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752).
Scheme 1:
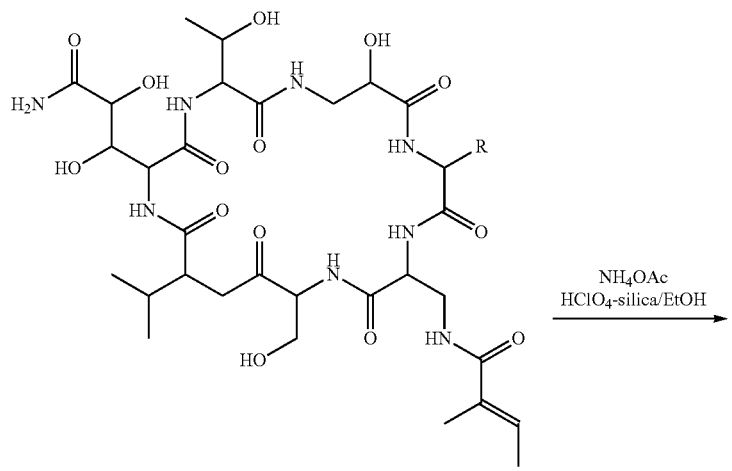
A
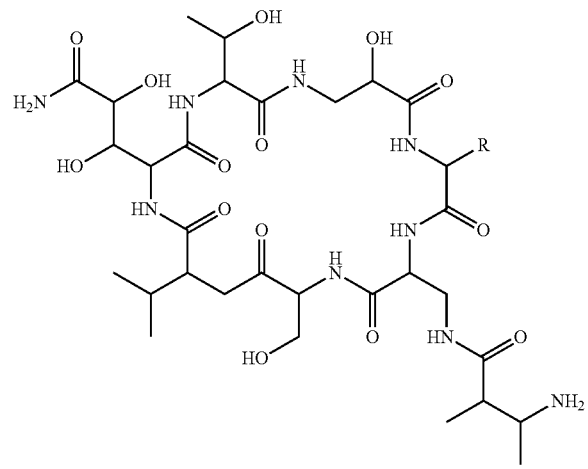
B
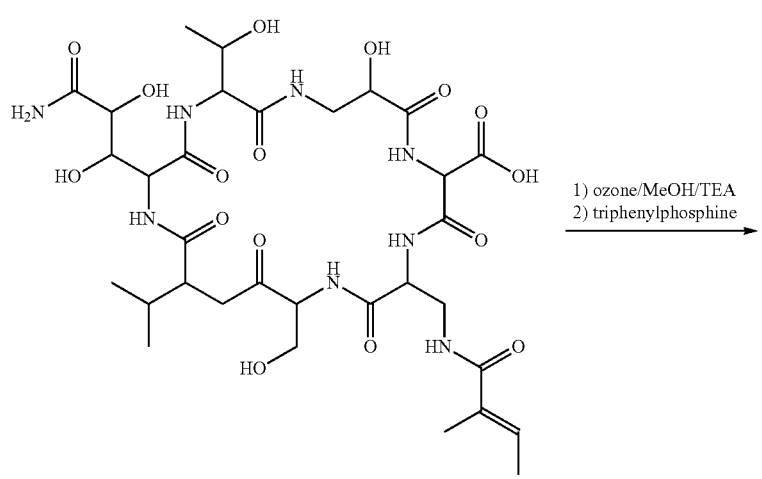

-continued
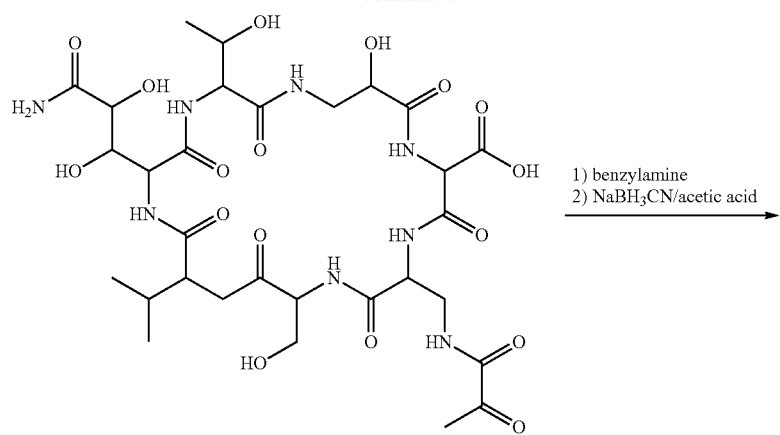
1) benzylamine
2) NaBH$_3$CN/acetic acid
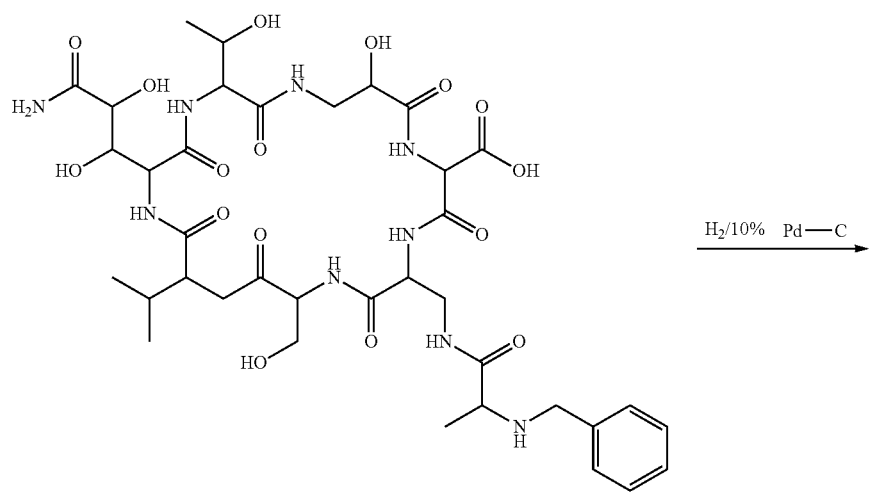
H$_2$/10% Pd—C
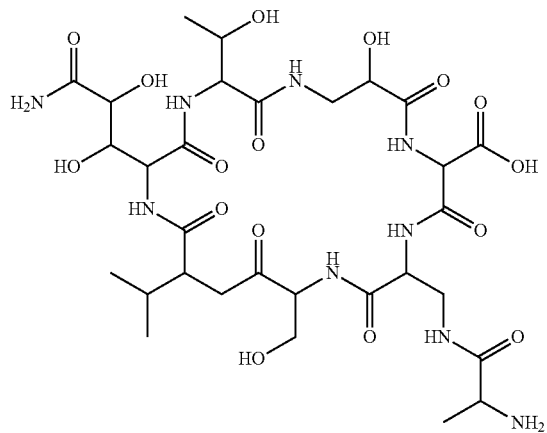

-continued

C

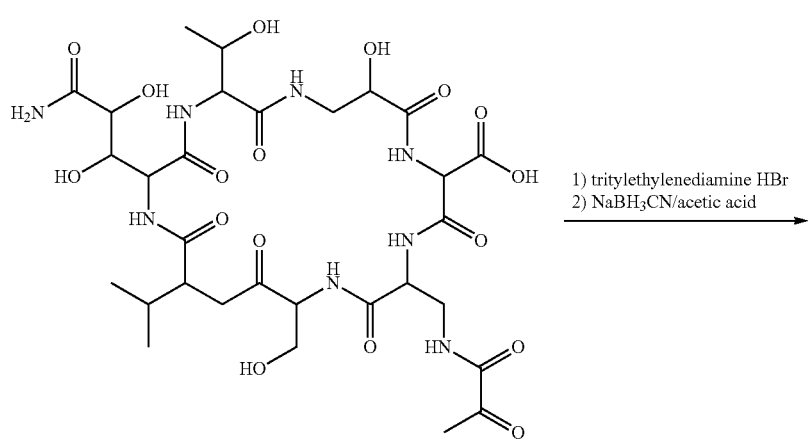

1) tritylethylenediamine HBr
2) NaBH₃CN/acetic acid

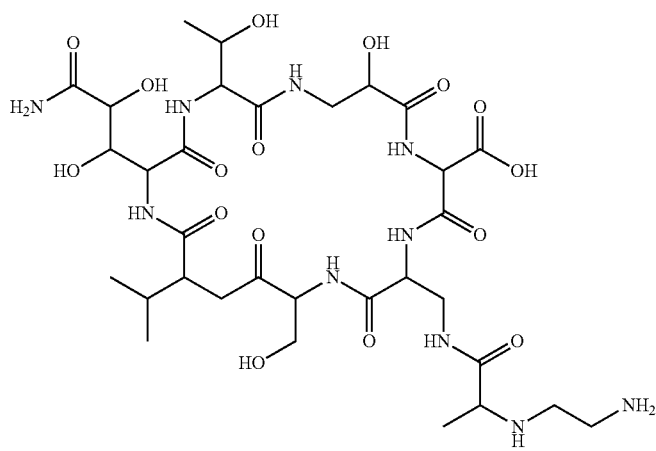

R = H or COOH

Scheme 2 below illustrates examples of synthetic routes to prepare rifaGEs in which the linker connects the C3 atom of the rifamycin fused ring system to the Cζ1 atom or the Cε atom of the GE23077 acyl-Apa sidechain. Panel (A) illustrates examples of syntheses of {rifamycin S}—NH-{descarboxy-GE23077}, {rifamycin SV}—NH-{descarboxy-GE23077}, {rifamycin S}—NH-{GE23077}, and {rifamycin SV}—NH-{GE23077}, wherein the —NH— linker connects the C3 atom of the rifamycin fused system to the Cζ1 atom of the descarboxy-GE23077 or GE23077 acyl-Apa sidechain. Panel (B) illustrates examples of syntheses of {rifamycin S}—NH-{GE23077} and {rifamycin SV}—NH-{GE23077}, wherein the —NH— linker connects the C3 atom of the rifamycin fused ring system to the Cε atom of the GE23077 acyl-Apa sidechain. Panel (C) illustrates examples of syntheses of {rifamycin S}—NHCH2CH2NH-{GE23077} and {rifamycin SV}—NHCH2CH2NH-{GE23077}, wherein the —NHCH2CH2NH— linker connects the C3 atom of the rifamycin fused ring system to the Cε atom of the GE23077 acyl-Apa sidechain.

Scheme 2:
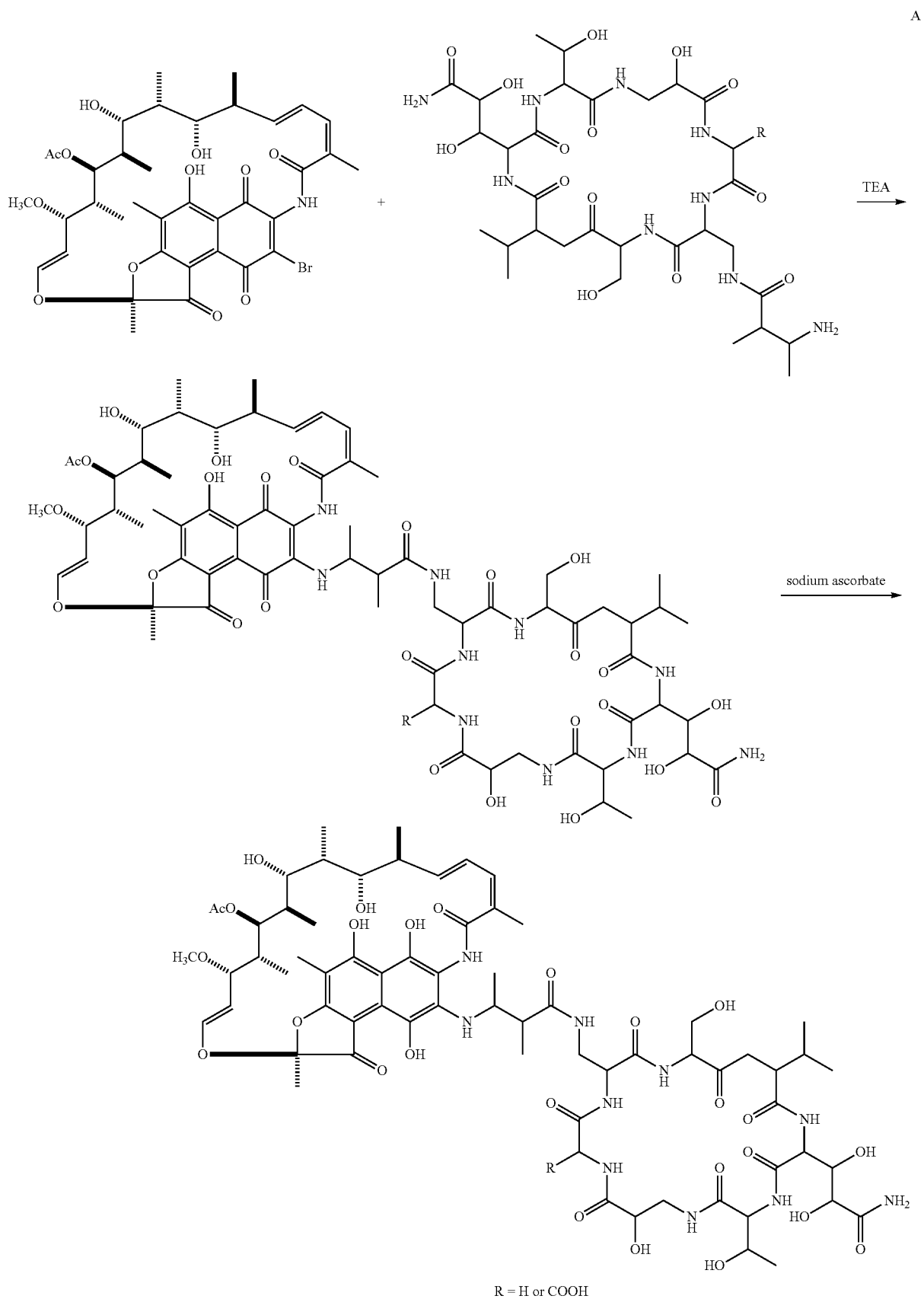
R = H or COOH

-continued
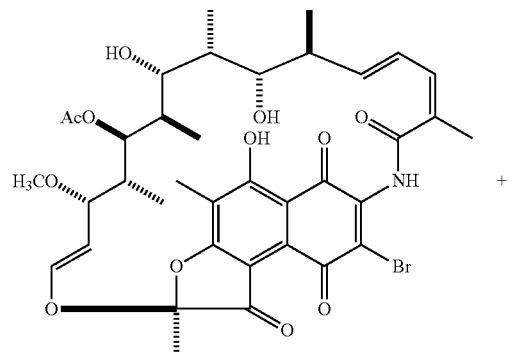
+
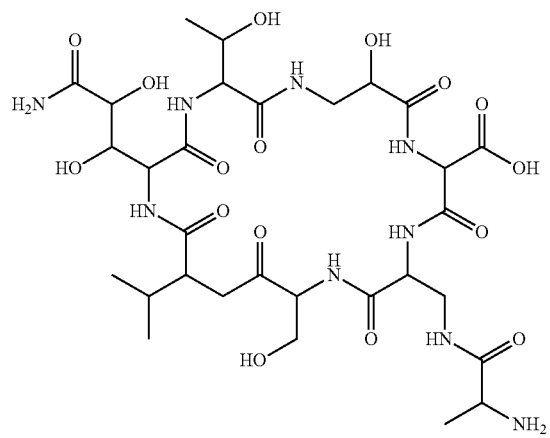
→ TEA
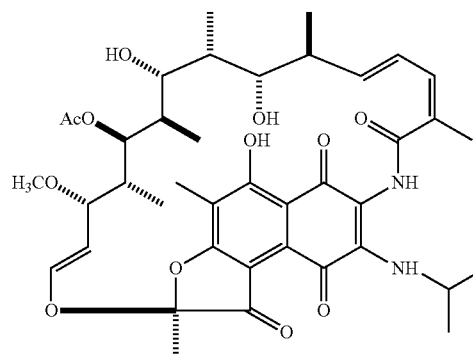
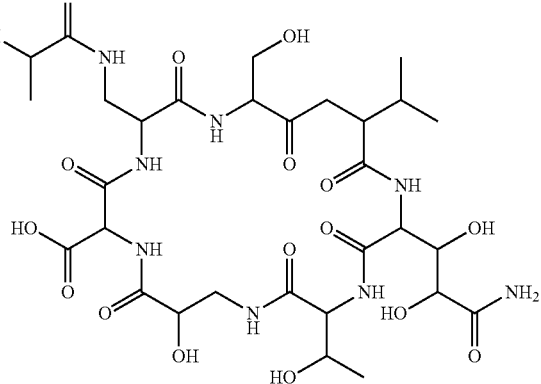
→ sodium ascorbate
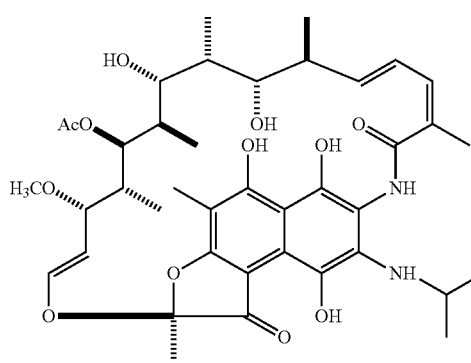
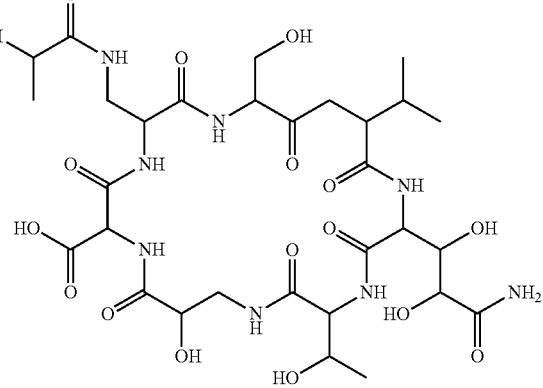
R = H or COOH -continued
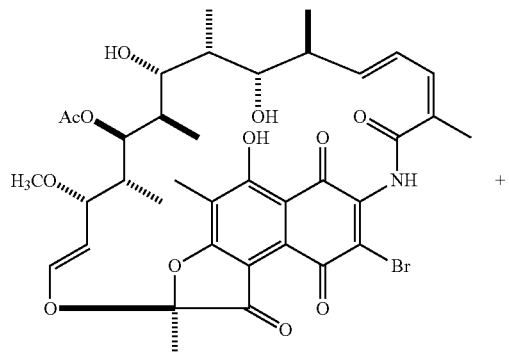
+
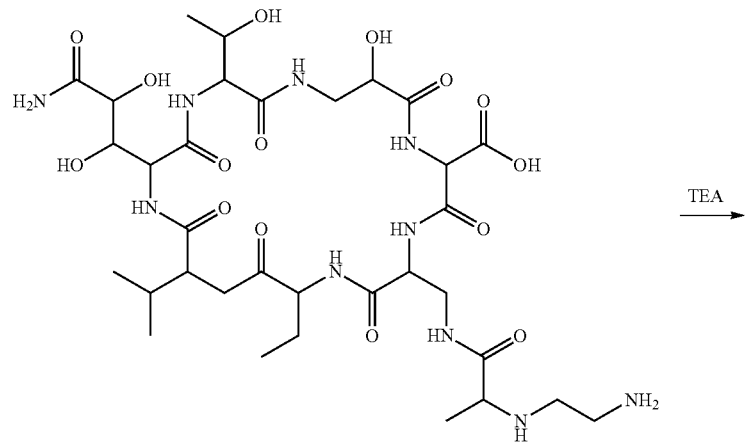
TEA →
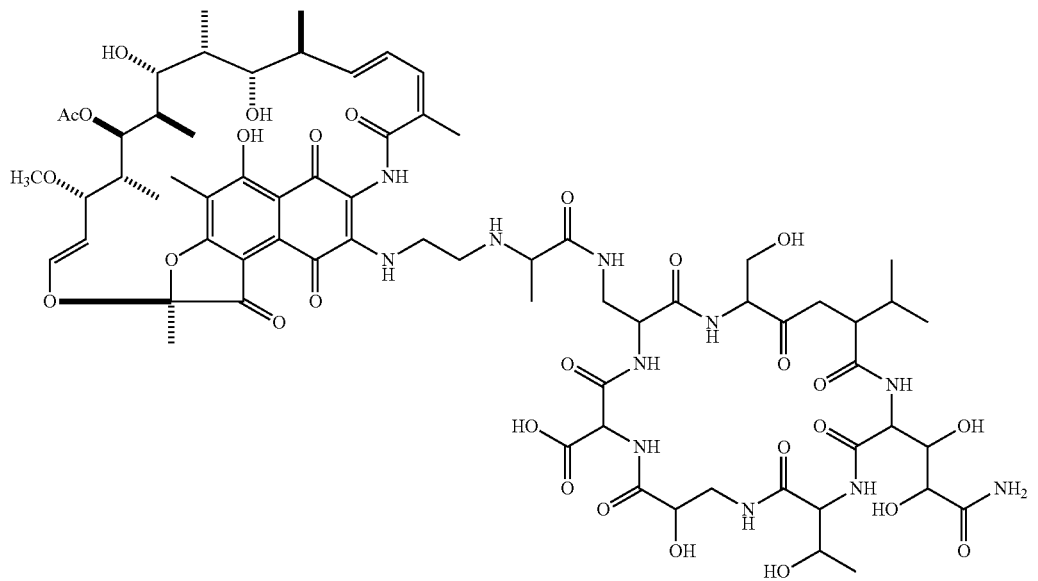
sodium ascorbate →

-continued

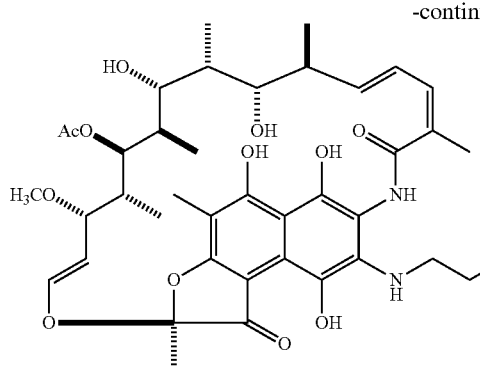
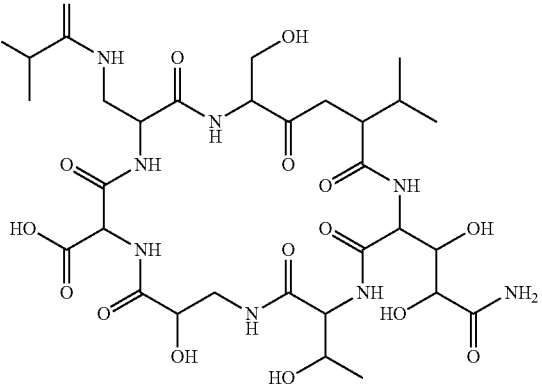

Scheme 3 below illustrates examples of synthetic routes to prepare rifaGEs in which the linker connects the oxygen atom pendant from the C4 atom of the rifamycin fused ring system to the Cζ1 atom or the Cε atom of the GE23077 acyl-Apa sidechain. Panel (A) illustrates an example of a synthesis of {rifamycin SV}—{CH2C(O)NH}-{descarboxy-GE23077}, and {rifamycin SV}—{CH2C(O)NH}-{GE23077}, wherein the —{CH2C(O)NH}— linker connects the oxygen atom pendant from the C4 atom of the rifamycin fused ring system to the Cζ1 atom of the descarboxy-GE23077 or GE23077 acyl-Apa sidechain. Panel (B) illustrates an example of a synthesis of {rifamycin SV}—{CH2C(O)NH}-{GE23077}, wherein the —{CH2C(O)NH}— linker connects the oxygen atom pendant from the C4 atom of the rifamycin fused ring system to the Cε atom of the GE23077 acyl-Apa sidechain. Panel (C) illustrates an example of a synthesis of {rifamycin SV}—{CH2C(O)NHCH2CH2NH}-{GE23077}, wherein the —{CH2C(O)NHCH2CH2NH}— linker connects the oxygen atom pendant from the C4 atom of the rifamycin fused ring system to the Cε atom of the GE23077 acyl-Apa sidechain.

Scheme 3:

A

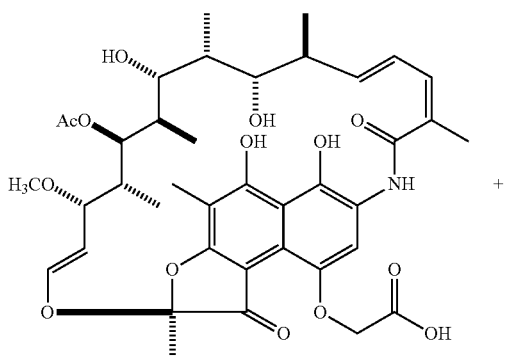

+

-continued
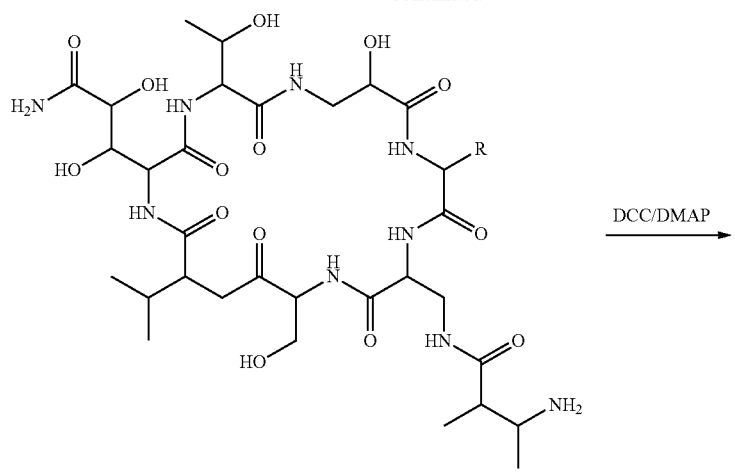
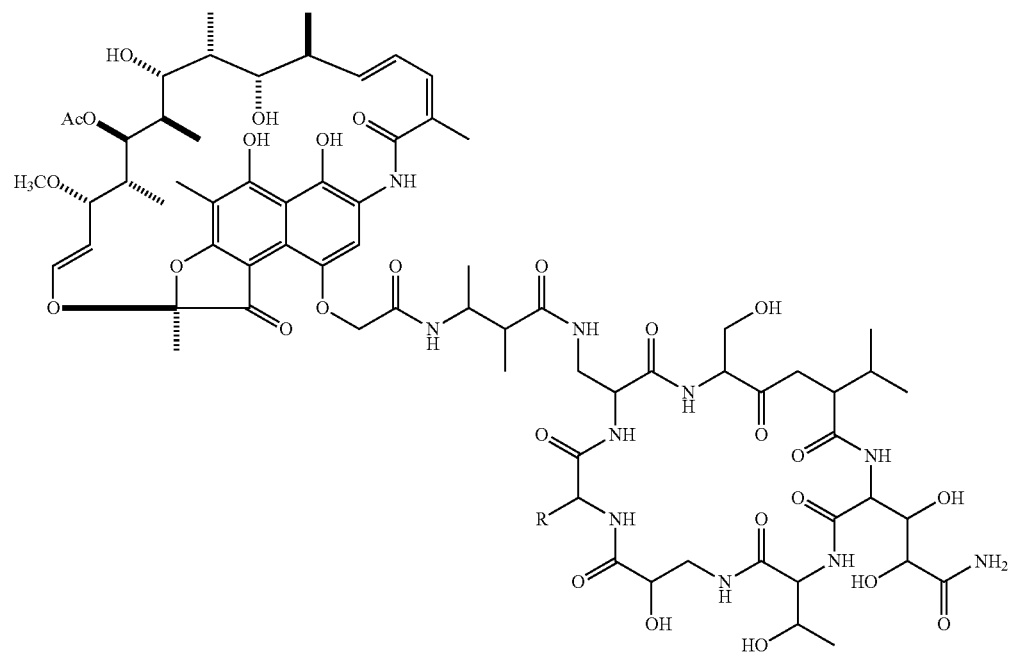
B
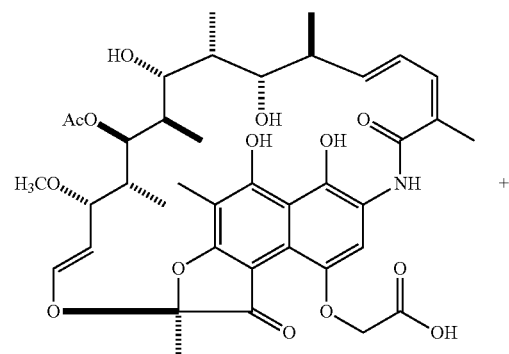
+

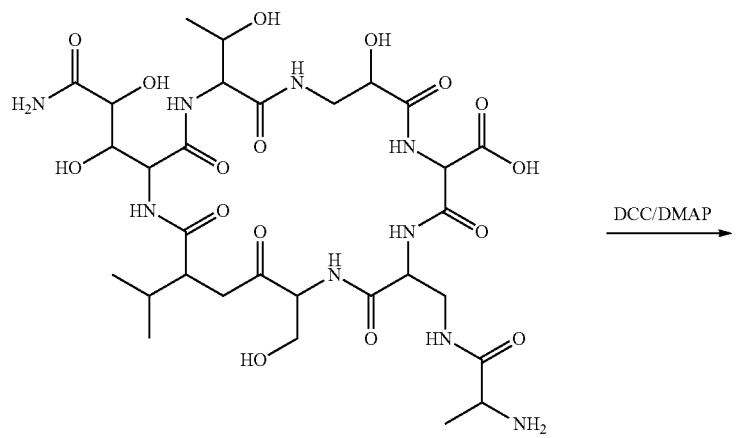
$\xrightarrow{\text{DCC/DMAP}}$
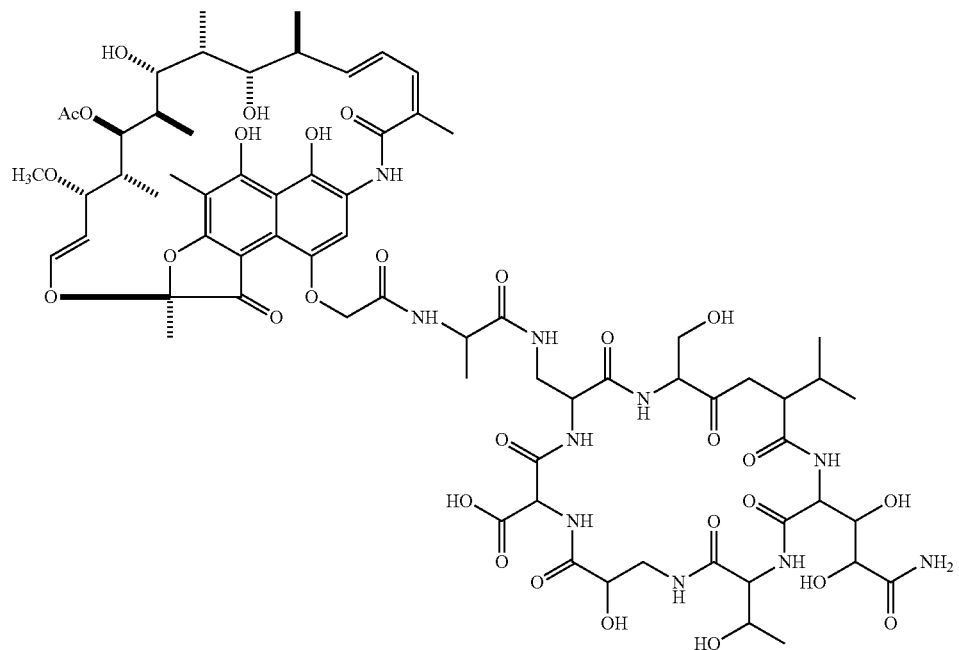
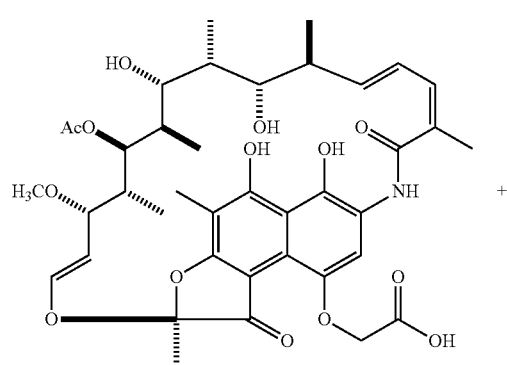
+
C

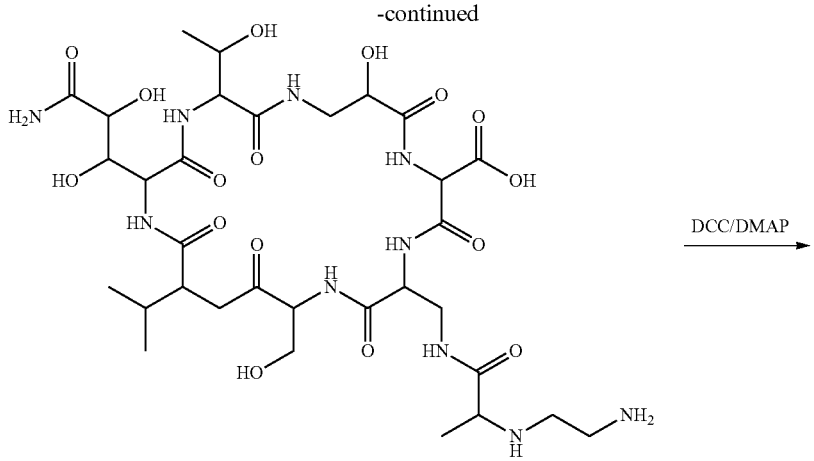

-continued

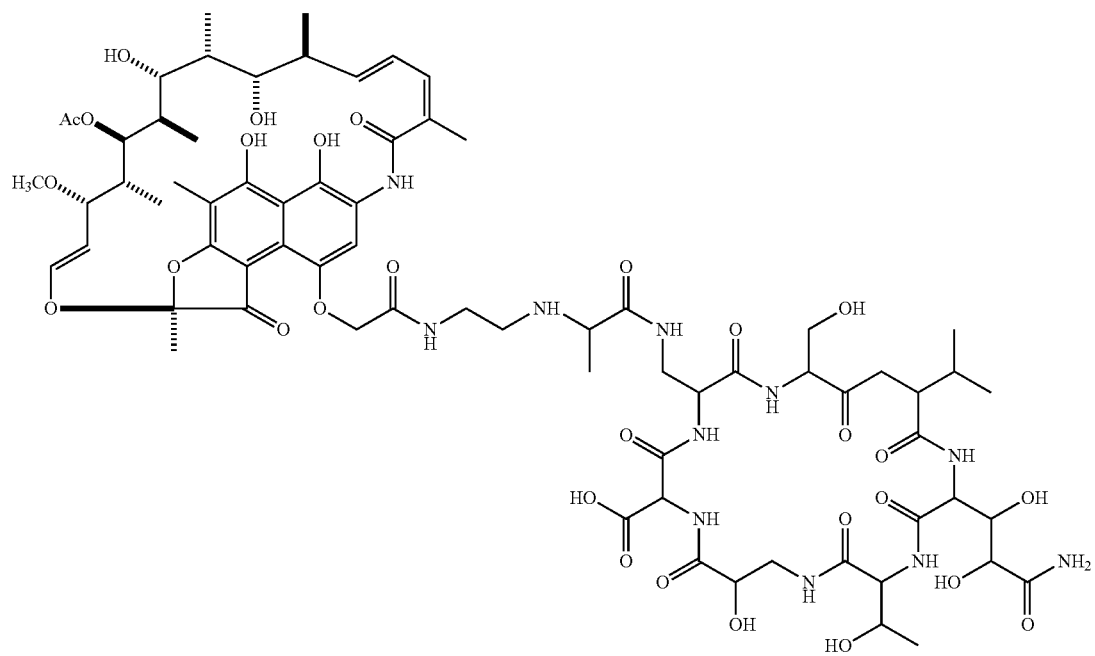 [SMILES: CO[C@H]1/C=C/O[C@@]2(C)Oc3c(C)c(O)c4c(O)c(cc(OCC(=O)NCCNC(C)C(=O)NCC5NC(=O)C(C(=O)O)NC(=O)C(O)CNC(=O)C(C(C)O)NC(=O)C(C(O)C(O)C(N)=O)NC(=O)C(C(C)C)CC(=O)C(CO)NC5=O)c4c3C2=O)NC(=O)/C(C)=C\C=C\[C@H](C)[C@H](O)[C@@H](C)[C@@H](O)[C@@H](C)[C@H](OC(C)=O)[C@@H]1C]

R = H or COOH

Scheme 4 below illustrates examples of synthetic routes to prepare soraGEs in which the linker connects the carbon atom of the carboxyl group of the sorangicin sidechain to the Cζ1 atom or the Cϵ atom of the GE23077 acyl-Apa sidechain. Panel (A) illustrates an example of the synthesis of {sorangicin A}-NH-{descarboxy-GE23077} and {sorangicin A}-NH-{GE23077}, wherein the —NH— linker connects the carbon atom of the carboxyl group of the sorangicin sidechain to the Cζ1 atom of the descarboxy-GE23077 or GE23077 acyl-Apa sidechain. Panel (B) illustrates an example of the synthesis of {sorangicin A}-NH-{GE23077}, wherein the —NH-linker connects the carbon atom of the carboxyl group of the sorangicin sidechain to the Cϵ atom of the GE23077 acyl-Apa sidechain. Panel (C) illustrates an example of the synthesis of {sorangicin A}-NHCH2CH2NH-{GE23077}, wherein the —NHCH2CH2NH— linker connects the carbon atom of the carboxyl group of the sorangicin sidechain to the Cϵ atom of the GE23077 acyl-Apa sidechain.

Scheme 4:
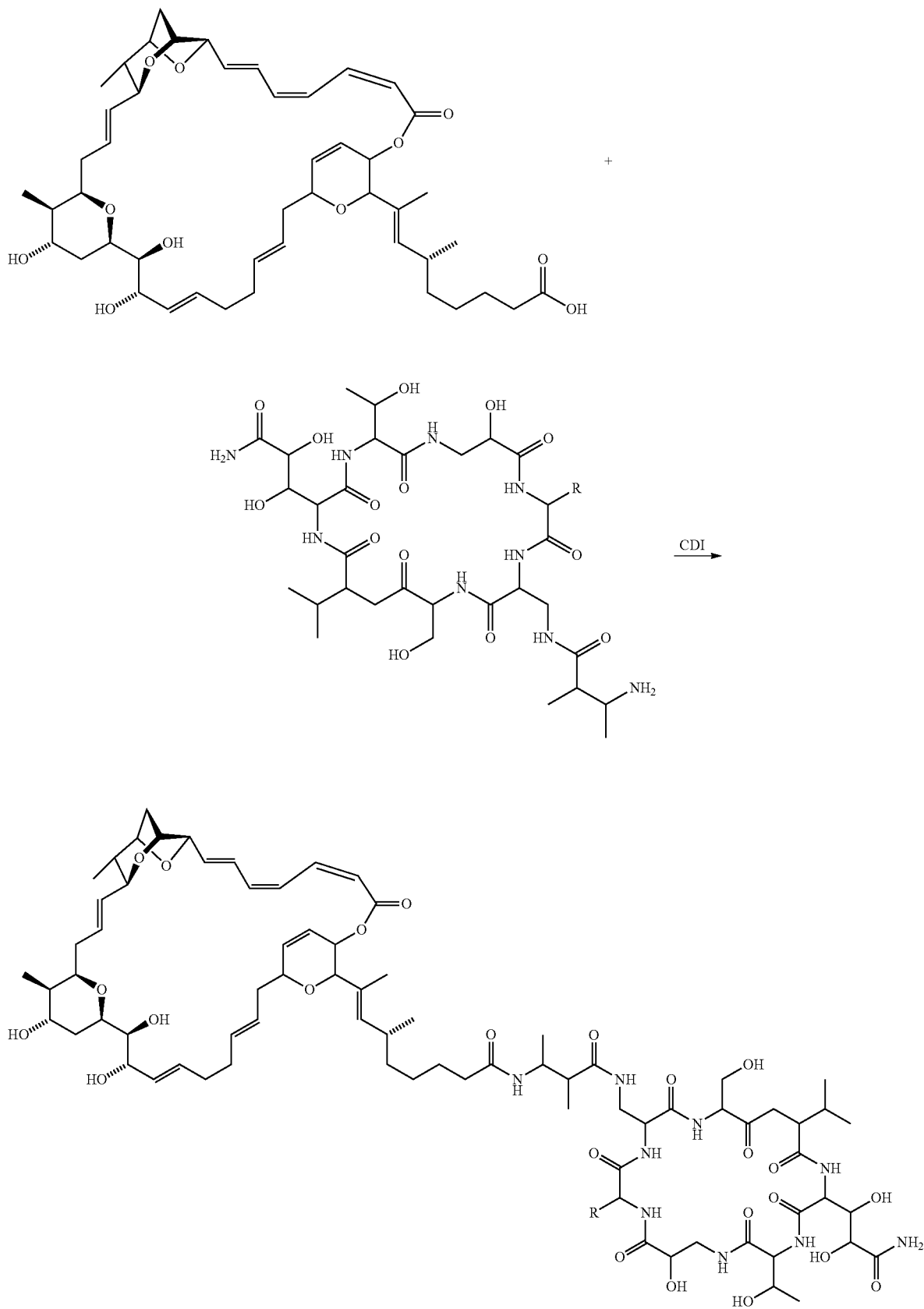

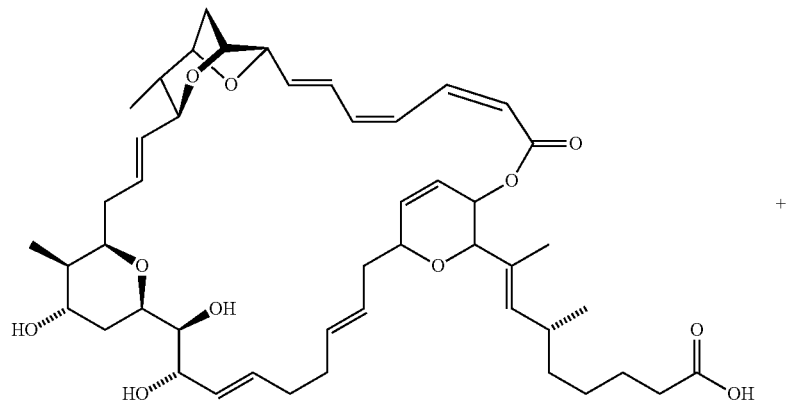
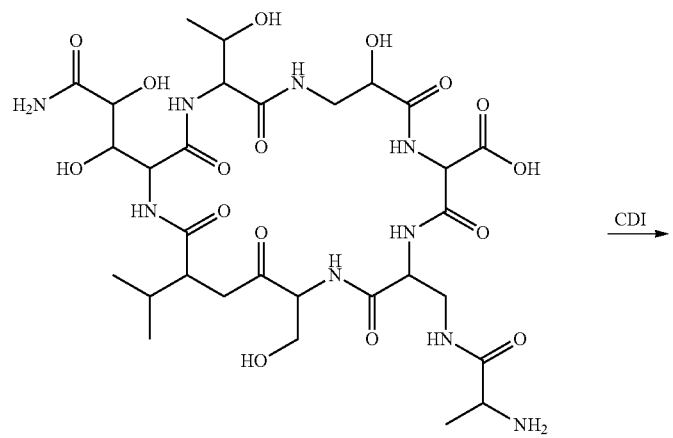
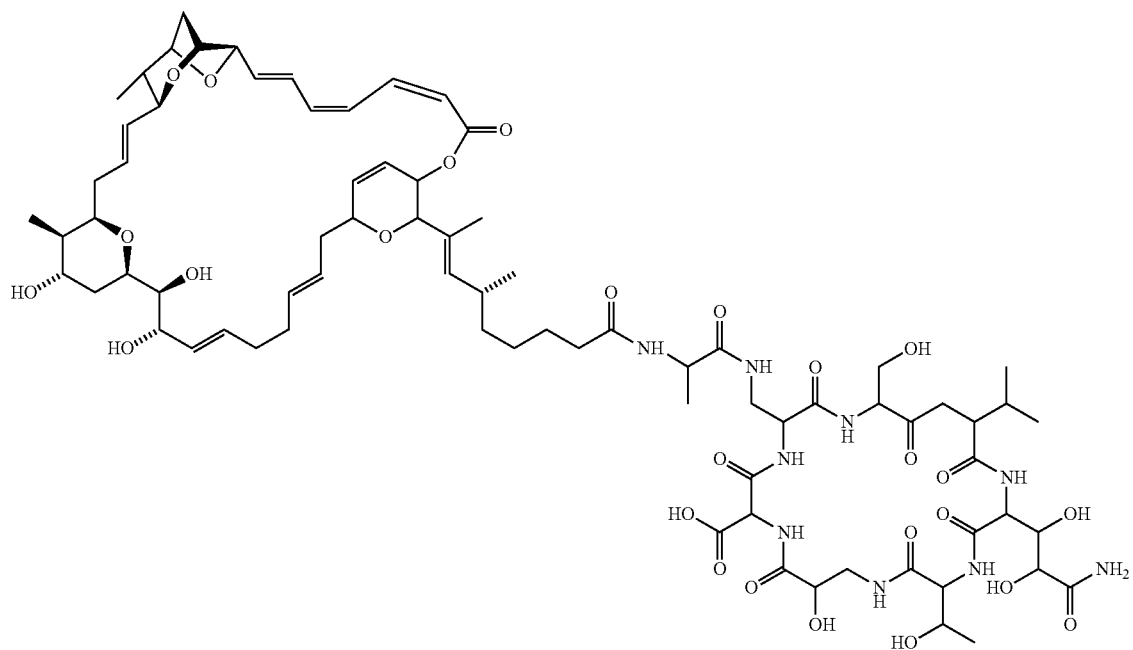

-continued
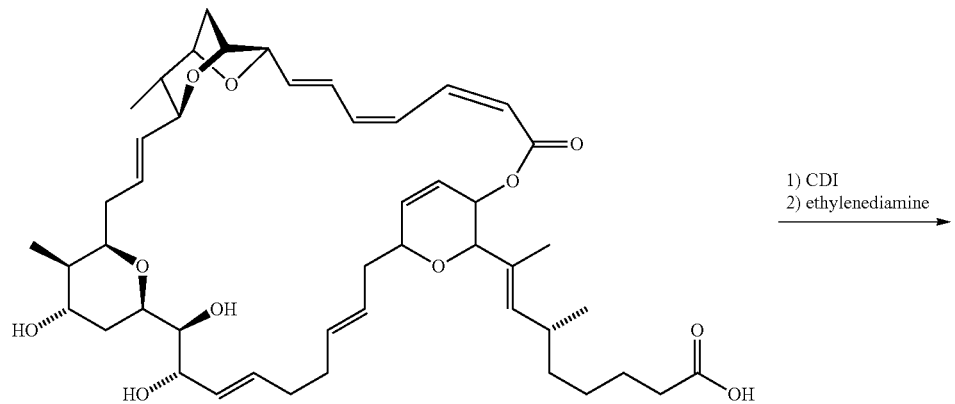
1) CDI
2) ethylenediamine →
C
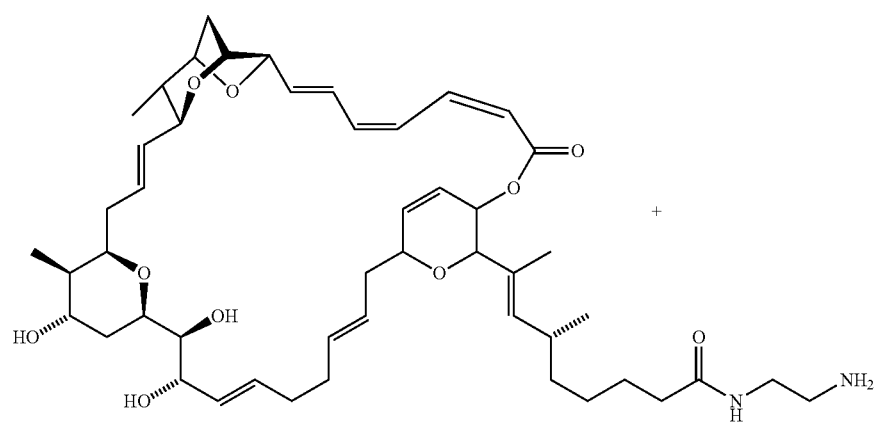
+
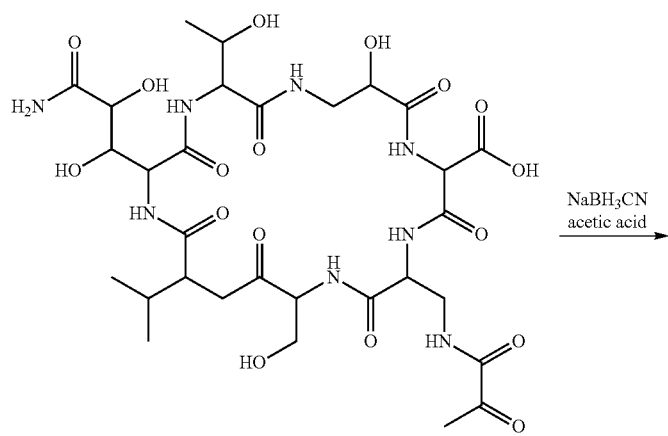
NaBH₃CN
acetic acid →

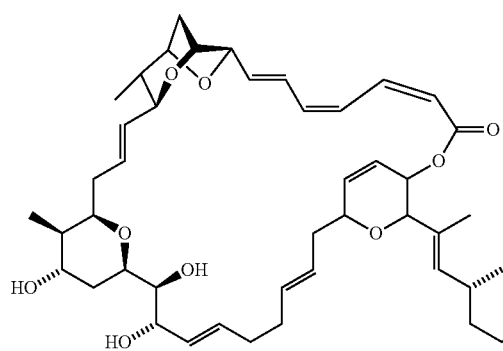

R = H or COOH

Pharmaceutical Preparations and Methods of Administration

In cases where compounds are sufficiently basic or acidic, a salt of a compound of the invention can be useful as an intermediate for isolating or purifying a compound of the invention. Additionally, administration of a compound of the invention as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compound of the invention can be formulated as pharmaceutical compositions and administered to a mammalian host, such as a human patient in a variety of forms adapted to the chosen route of administration, i.e., orally or parenterally, by intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compound of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 10 to about 100 mg/kg of body weight per day, such as 3 to about 75 mg per kilogram body weight of the recipient per day, preferably in the range of 6 to 120 mg/kg/day, most preferably in the range of 15 to 90 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

INDUSTRIAL APPLICABILITY

Compounds identified according to the target and method of this invention would have applications not only in antibacterial therapy, but also in: (a) identification of bacterial RNAP (diagnostics, environmental-monitoring, and sensors applications), (b) labeling of bacterial RNAP (diagnostics, environmental-monitoring, imaging, and sensors applications), (c) immobilization of bacterial RNAP (diagnostics, environmental-monitoring, and sensors applications), (d) purification of bacterial RNA polymerase (biotechnology applications), (e) regulation of bacterial gene expression (biotechnology applications), and (f) antisepsis (antiseptics, disinfectants, and advanced-materials applications).

EXAMPLES

With reference to the examples below, Applicant has identified compounds that inhibit bacterial RNAP.

Example 1

Synthesis of {Rifamycin S}—NH-{Descarboxy-GE23077}, and {Rifamycin SV}—NH-{Descarboxy-GE23077}, Wherein the —NH— Linker Connects the C3 Atom of the rifamycin Fused Ring System to the Cζ1 Atom of the Descarboxy-GE23077 acyl-Apa sidechain (Schemes 1a and 2a; Compounds 2 and 3)

Example 1a

Synthesis of Compound 1

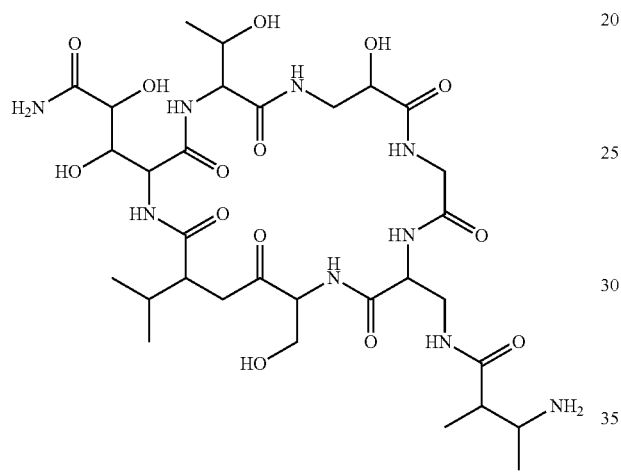

(1)

GE23077 (20 mg 25 μmol; prepared as in Ciciliato, I., Corti, E., Sarubbi, E., Stefanelli, S., Gastaldo, L., Montanini, N., Kurz, M., Losi, D., Marinelli, F., and Selva, E. (2004) *J. Antibiot.* 57, 210-217), ammonium acetate (60 mg; 780 μmol; Aldrich), and perchloric-acid-impregnated silica (5 mg, prepared as in Singh, S., Kumar, T., Chandrasekharam, M., Giribabu, L., and Reddy, P. (2009) *Synth Commun.* 22, 3982-3989), were mixed in 4 ml absolute ethanol in a screw-cap vial. The mixture was microwaved for 4×30 s (1000 W) with intervals of 1 min for re-mixing contents of the vial. The mixture was allowed to incubate at room temperature for another 16 h, evaporated to dryness, and resuspended in 2 ml 1% triethylamine-water. The mixture was centrifuged, and the supernatant was purified via HPLC (Phenomenex C18, semi-prep; 5' 0% B, 20' 5% B, 25' 10% B, 30' 30% B, 40' 80% B; A=water, B=acetonitrile, 2 ml/min).

The HPLC elution profile and mass spectrum of the product indicate that the product has undergone decarboxylation of the Ama sidechain (see Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752). It is known that acid and heat induce decarboxylation of the GE23077 Ama sidechain, and that decarboxylated GE23077 retains RNAP-inhibitory activity and antibacterial activity (Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752).

Yield: 3.5 mg; 36%.

MS (MALDI): calculated: m/z 777.80 (MH$^+$). found: 778.20, 800.59 (M+Na$^+$).

Example 1b

Synthesis of Compound 2

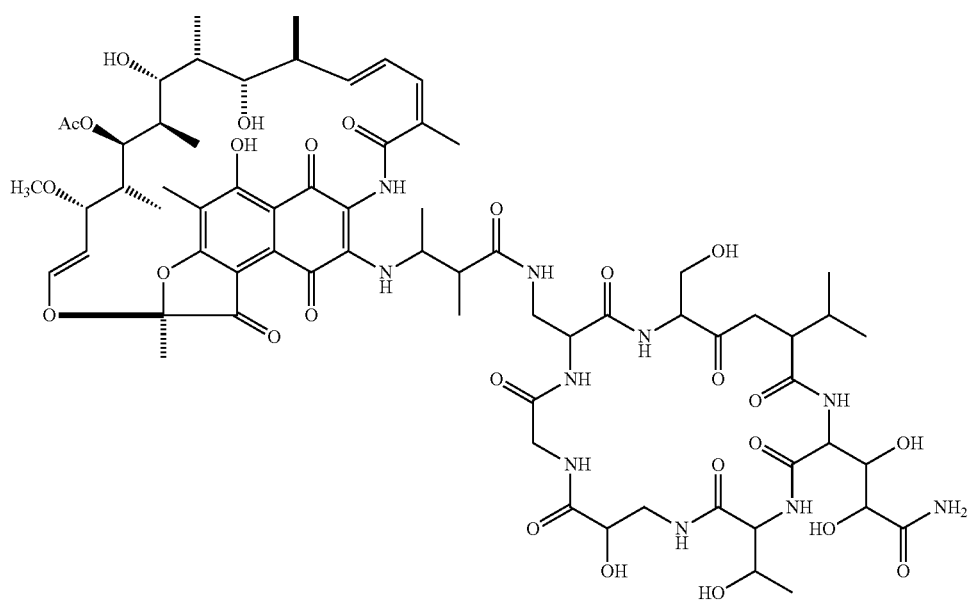

(2)

3-bromo-rifamycin S (2.7 mg; 3.47 µmol; prepared as in U.S. Pat. No. 4,179,438), compound 1 (2.7 mg; 3.47 µmol; Example 1a) and triethylamine (0.5 µl; 3.47 µmol; Aldrich) were mixed together in 200 µl DMF and allowed to react for 18 h at 25° C. The reaction mixture was quenched with 100 µl water, centrifuged, and the supernatant was purified via HPLC (Phenomenex C18, semi-prep; 0' 10% B, 35' 100% B; A=water, B=acetonitrile, 2 ml/min).

Yield: 1.51 mg; 30%.

MS (MALDI): calculated: m/z 1493.52 (M+Na$^+$). found: 1494.22.

Example 1c

Synthesis of Compound 3

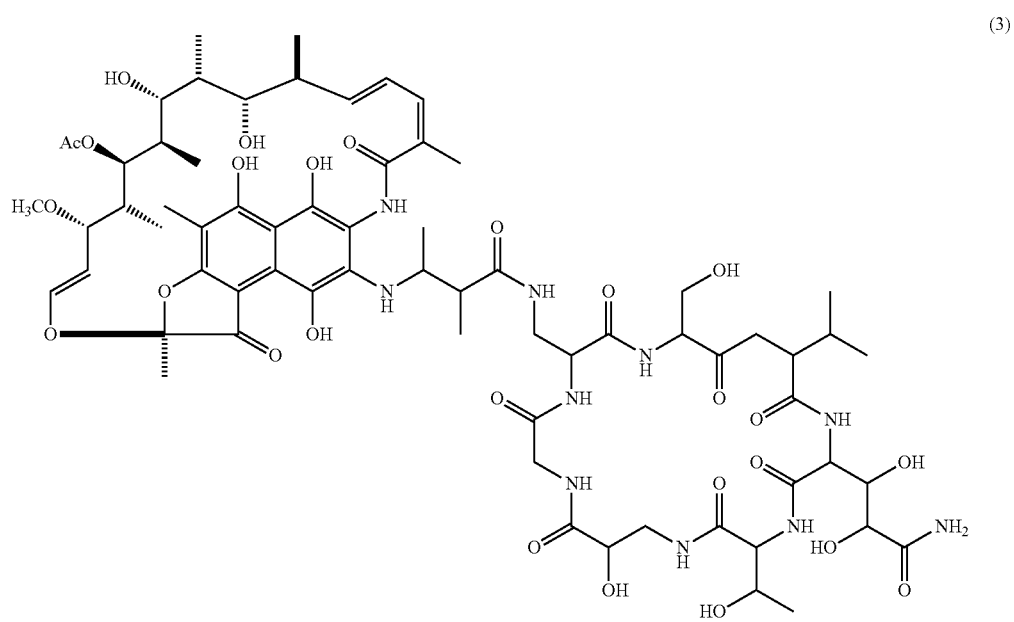

(3)

Sodium ascorbate (2.38 mg; 12 µmol; Aldrich) in 25 µl water was added to compound 2 (0.600 mg; 0.4 µmol; Example 1b) in 100 µl water, mixed, and allowed to react for 10 min at 25° C. The product was isolated via HPLC (Phenomenex C18, analytical; 0' 10% B, 35' 100% B; A=water, B=acetonitrile, 1 ml/min).

Yield: 0.1 mg; 17%.

MS (MALDI): calculated: m/z 1495.52 (M+Na$^+$). found: 1495.71.

Example 2

Synthesis of {Rifamycin SV}—CH2C(O)NH}-{GE23077}, Wherein the —{CH2C(O)NH}— Linker Connects the Oxygen Atom Pendant from the C4 Atom of the rifamycin Fused Ring System to the Cζ1 Atom of the GE23077 acyl-Apa Sidechain (Schemes 1a and 3a; Compound 4)

Example 2a

Synthesis of Compound 4

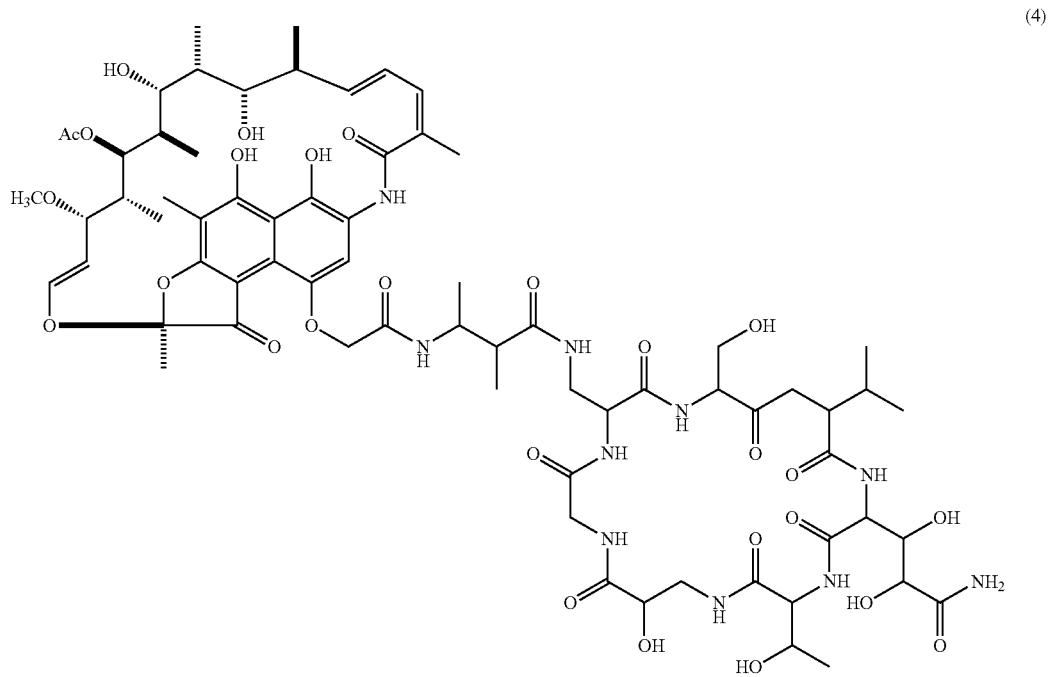

(4)

Rifamycin B (3.3 mg; 4.4 μmol; Pharmeks) and dicyclohexyldiimide (2 mg; 9.7 μmol; Aldrich) were stirred together in 0.5 ml anhydrous DMF for 1 h at 25° C. The mixture was added to Example 1a (1.5 mg; 2 μmol in 0.1 ml DMF containing a few grains of 4-dimethylaminopyridine) and was stirred for 1 h at 25° C. Water (0.1 ml) was added to quench the reaction, and the reaction products were evaporated to dryness, re-dissolved in methanol, and purified via HPLC (Phenomenex C18, semi-prep; 5' 0% B, 20' 5% B, 25' 10% B, 30' 30% B, 40' 80% B; A=water, B=acetonitrile, 2 ml/min)

Yield: 10 μg; 3.3%.

MS (MALDI): calculated: m/z 1515.67 (M+H$^+$). found: 1515.71.

Example 3

Synthesis of {Rifamycin SV}—CH2C(O)NHCH2CH2NH}-{GE23077}, Wherein the —{CH2C(O)NHCH2CH2NH}— Linker Connects the Oxygen Atom Pendant from the C4 atom of the Rifamycin Fused Ring System to the Cϵ Atom of the GE23077 acyl-Apa sidechain (Schemes 1c and 3c; Compound 7)

Example 3a

Synthesis of Compound 5

(5)

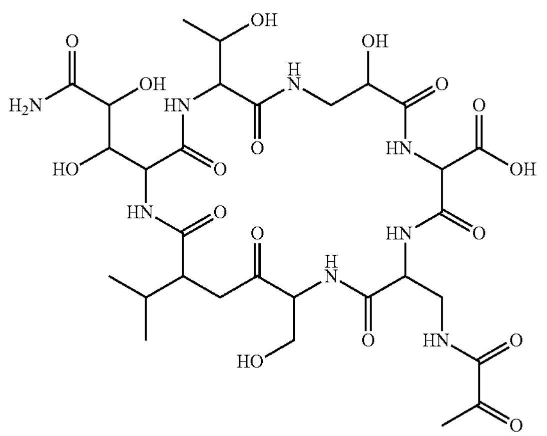

Compound 5 was prepared essentially as in Mariani, R., Granata, G., Maffioli, S., Serina, S., Brunati, C., Sosio, M., Marazzi, A., Vannini, A., Patel, D., White, R. and Ciabatti, R. (2005) *Bioorg. Med. Chem.* 15, 3748-3752. GE23077 (60 mg; 75 mmol; prepared as in Ciciliato, I., Corti, E., Sarubbi, E., Stefanelli, S., Gastaldo, L., Montanini, N., Kurz, M., Losi, D., Marinelli, F., and Selva, E. (2004) *J. Antibiot.* 57, 210-217) was dissolved in 16 ml methanol and brought to −72° C. Ozone was bubbled through the solution for 1 hour (LAB2B ozone generator; Ozonia North America). The solution was allowed to come to room temperature, and argon was bubbled through the solution for 15 min. Triphenylphosphine (74 mg, 225 μmol; Aldrich) was added to the reaction mixture, and reaction was allowed to proceed for 16 h at 25° C. The reaction mixture was evaporated to dryness, and the solid was triturated with ethyl acetate. The resulting white solid was re-dissolved in 1% TEA and purified via HPLC.

Yield: 4 mg, 13%.

MS (MALDI): calculated: m/z 770.71 ($M+Na^+-CO2$), 792.72 ($M+H^+$). found: 771.17, 792.32.

Example 3b

Synthesis of Compound 6

(6)

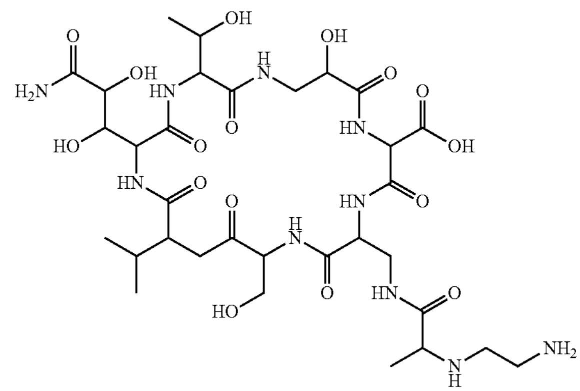

Compound 5 (4 mg; 5.2 μmol; Example 3a) in 100 μl DMF was mixed with tritylethylenediamine hydrobromide (20 mg; 52 μmol; Aldrich) and diisopropylethylamine (9 μl; 4 mg; 52 μmol; Aldrich) in 100 μl DMF, and the reaction mixture was stirred for 3 h at 25° C. Acetic acid (3.06 μl, 52 μmol; Aldrich) was added, and stirring was continued for 30 min. Sodium cyanoborohydride (1 mg, 15.6 μmol; Aldrich) was added, and stirring was continued for 1 h. The reaction was quenched by the addition of 1 ml water and 1 ml methanol, and the resulting trityl-protected-product was purified via HPLC. Fractions containing the trityl-protected-product were pooled, dried, treated with 200 μl 80% acetic acid for 20 min at 25° C. followed by 500 μl water for 1 min at 25° C. in order to remove the trityl protecting group, and the product was purified via HPLC (Phenomenex C8, semi-prep; 0' 20% B, 30' 100% B; A=water, B=acetonitrile, 2 ml/min)

Yield: 4 mg, 92%.

MS (MALDI): calculated: m/z 858.81 ($M+Na^+$). found: 860.04, 861.04.

Example 3c

Synthesis of Compound 7

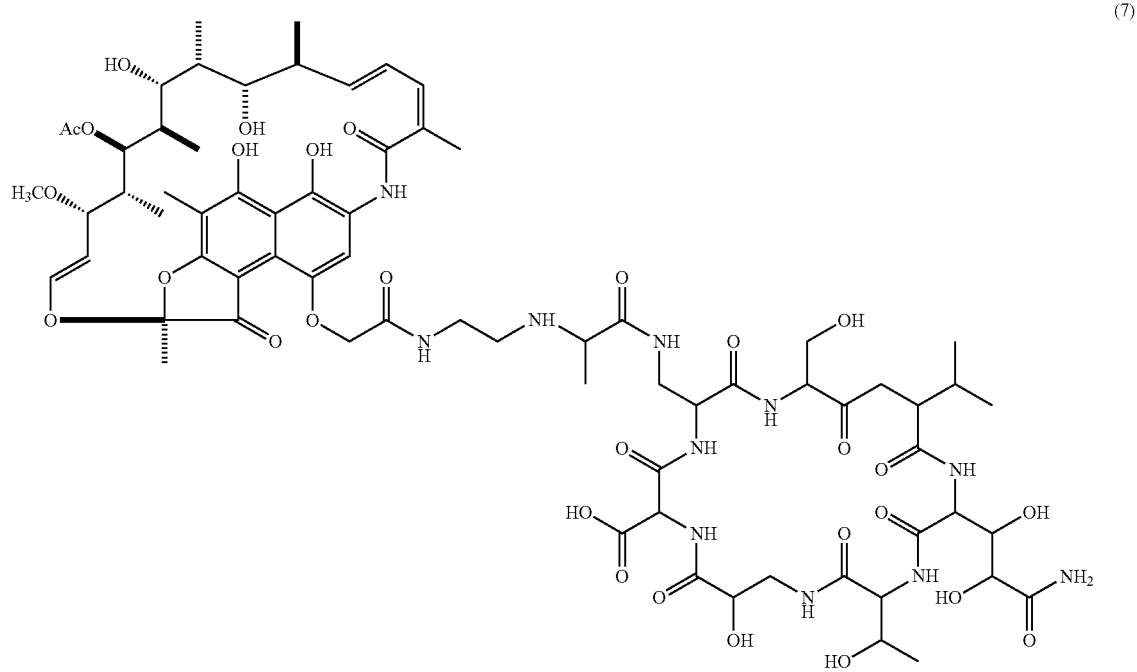

(7)

Rifamycin B (10 mg; 29 mmol; Pharmeks) and dicyclohexyldiimide (6 mg; 29 μmol; Aldrich) were stirred in 0.5 ml anhydrous THF for 1 h at 25° C., during which time a solid precipitated. The supernatant was added to compound 6 of Example 3b (4 mg; 4.8 mmol in 0.5 ml DMF containing a few grains of 4-dimethylaminopyridine) and stirred for 16 h at 25° C. Water (0.1 ml) was added to quench the reaction, and the reaction product was evaporated to dryness, re-dissolved in methanol, and purified via HPLC (Phenomenex C8, semi-prep; 0' 20% B, 30' 100% B; A=water, B=acetonitrile, 2 ml/min).

MS (MALDI): calculated: m/z 1596.61 (M+Na$^+$). found: 1597.84, 1596.84, 1573.81 (parent ion).

Example 4

Synthesis of {Sorangicin A}-NHCH2CH2NH-{GE23077}, Wherein the —NHCH2CH2NH— Linker Connects the Carbon Atom of the Carboxyl Group of the Sorangicin sidechain to the Cε Atom of the GE23077 acyl-Apa sidechain (Scheme 4; Compound 9)

Example 4a

Synthesis of Compound 8

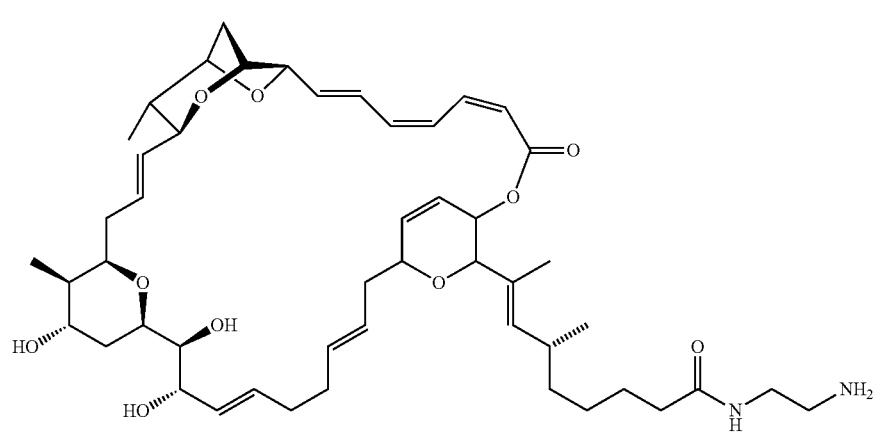

(8)

Sorangicin A (7.5 mg; 9.3 μmol; prepared as in Rommelle, et al. (1990) *J Antibiotics* 43, 88-91) was mixed with carbodiimidazole (2.5 mg, 15.4 μmol; Aldrich) in 500 μl THF and stirred under argon for 48 h at 25° C. The reaction was cooled on ice and, to it, was added ethylenediamine dihydrochloride (6.2 mg; 46.5 μmol; Aldrich) in 50 μl water and 12.8 μl triethylamine (93 μmol; Aldrich). The reaction was allowed to continue for 20 min on ice, and then was quenched by addition of 1 ml ice water, extracted with 3×1 ml ethyl acetate, and evaporated to a white solid. The product was isolated by flash silica chromatography (1% acetic acid in 1:9 methanol-chloroform).

Yield: 1 mg, 12.5%.

MS (MALDI): calculated: m/z 871.51 (M+Na$^+$). found: 871.60.

Example 4b

Synthesis of Compound 9

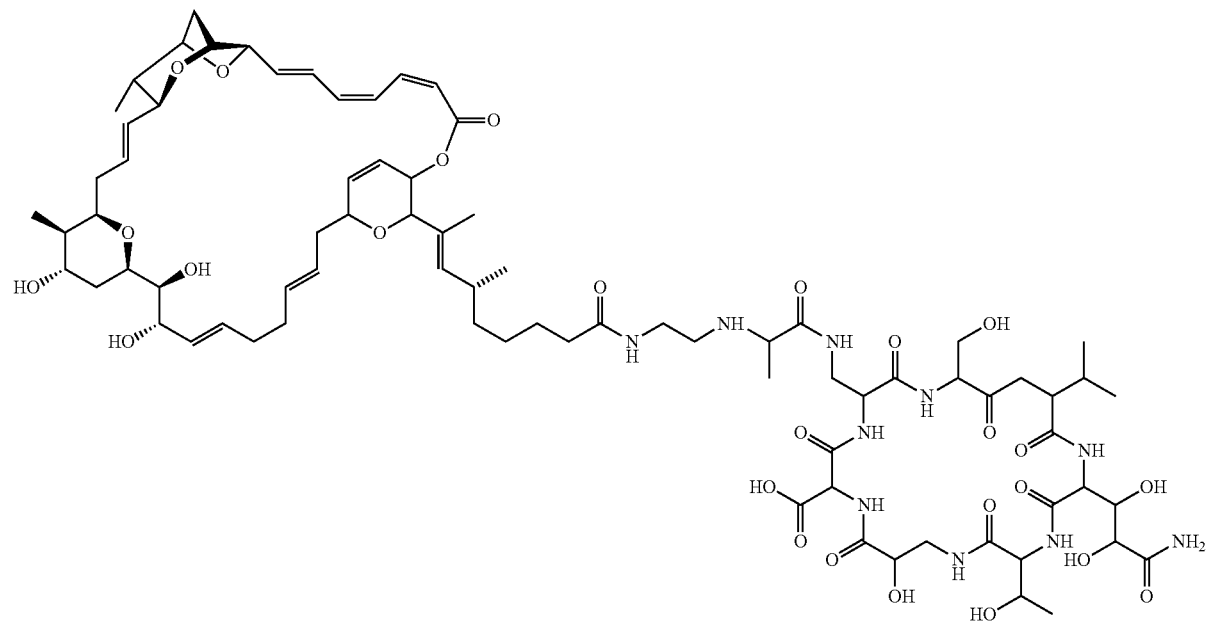

Compound 8 (1 mg; 1.66 μmol; Example 4a) is added to compound 5 (Example 3a) in 50 μl DMF. After stirring for 3 h at 25° C., acetic acid (1 μl, 17 μmol; Aldrich) is added, and, after further stirring for 30 min at 25° C., sodium cyanoborohydride (0.3 mg, 5 μmol; Aldrich) is added, and the reaction mixture is further stirred for 1 h at 25° C. The reaction is quenched by the addition of 0.5 ml water and 0.5 ml methanol, and the product is purified via HPLC.

Example 5

Assay of RNAP-Inhibitory Activity

Fluorescence-detected RNA polymerase assays with *E. coli* RNA polymerase were performed by a modification of the procedure of Kuhlman et al., 2004 [Kuhlman, P., Duff, H. and Galant, A. (2004) A fluorescence-based assay for multi-subunit DNA-dependent RNA polymerases. Anal. Biochem. 324, 183-190]. Reaction mixtures contained (20 μl): 0-100 nM test compound, 75 nM *Escherichia coli* RNA polymerase σ$^{70}$ holoenzyme or *Escherichia coli* RNA polymerase σ$^{70}$ holoenzyme derivative (prepared as in Feklistov, A., Mekler, V., Jiang, Q., Westblade, L., Irschik, H., Jansen, R., Mustaev, A., Darst, S., and Ebright, R. (2008) *Proc. Natl. Acad. Sci. USA* 105, 14820-14825), 20 nM 384 bp DNA fragment containing the bacteriophage T4 N25 promoter, 100 μM ATP, 100 μM GTP, 100 μM UTP, 100 μM CTP, 50 mM Tris-HCl, pH 8.0, 100 mM KCl, 10 mM MgCl$_2$, 1 mM DTT, 10 μg/ml bovine serum albumin, and 5.5% glycerol. Reaction components other than DNA and NTPs were pre-incubated for 10 min at 37° C. Reactions were carried out by addition of DNA and incubation for 5 min at 37° C., followed by addition of NTPs and incubation for 60 min at 37° C. DNA was removed by addition of 1 μl 5 mM CaCl$_2$ and 2 U DNaseI (Ambion, Inc.), followed by incubation for 90 min at 37° C. RNA was quantified by addition of 100 μl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QM1 spectrofluorimeter (PTI, Inc.)]. IC50 is defined as the concentration of inhibitor resulting in 50% inhibition of RNA polymerase activity.

Example 6

Assay of Antibacterial Activity

Minimum inhibitory concentrations (MICs) for *Staphylococcus aureus* ATCC 12600, *Enterococcus faecalis* ATCC 19433, *Acinetobacter baumannii* ATCC 19606, and *Escherichia coli* D21f2tolc (Fralick, J. and Burns-Keliher, L. (1994) *J. Bacteria* 176, 6404-6406) were quantified using broth microdilution assays as described [Clinical and Laboratory Standards Institute (CLSI/NCCLS) (2009) *Methods for Dilution Antimicrobial Susceptibility Tests for Bacteria That Grow Aerobically; Approved Standard, Eighth Edition. CLIS Document M07-A8* (CLIS, Wayne Pa.)].

Screening data for a compound of this invention, the rifaGE having the formula {rifamycin SV}—NH—{descarboxy- GE23077}, wherein the —NH— linker connects the C3 of the rifamycin SV fused ring system to Cζ1 of the descarboxy-GE23077 acyl-Apa sidechain (compound 3; Example 1), and for the parent compounds, rifamycin B and GE23077, are presented in the following Tables:

TABLE 1

Inhibition of a rifamycin-resistant *Escherichia coli* RNAP derivative ([Asn516]β-RNAP).

| name | IC50 rifamycin-resistant RNAP ([Asn516]β-RNAP) (nM) |
|---|---|
| RifaGE (compound 3) | 0.15 |
| rifamycin SV | 12 |

TABLE 2

Inhibition of a rifamycin-resistant *Escherichia coli* RNAP derivative ([Asn516]β-RNAP).

| name | IC50 GE23077-resistant RNAP ([Asp565]β-RNAP) (nM) |
|---|---|
| RifaGE (compound 3) | 0.02 |
| GE23077 | >100 |

TABLE 3

Inhibition of bacterial growth.

| name | MIC *S. aureus* ATCC12600 (µg/ml) | MIC *E. faecalis* ATCC 19433 (µg/ml) | MIC *A. baumannii* ATCC 19606 (µg/ml) | MIC *E. coli* D21f2toIC (µg/ml) |
|---|---|---|---|---|
| RifaGE (compound 3) | 0.05 | 6 | 10 | 2 |

The data in Table 1 show that a compound of this invention inhibits a rifamycin-resistant derivative of *Escherichia coli* RNAP—[Asn516]β RNAP—with a potency 80 times higher than the potency of rifamycin SV (IC$_{50}$=0.15 µM vs. IC$_{50}$=12 µM).

The data in Table 2 show that a compound of this invention inhibits a GE23077-resistant derivative of *Escherichia coli* RNAP—[Asp565]β RNAP—with a potency >5,000 times higher than the potency of GE23077 (IC$_{50}$=0.02 µM vs. IC$_{50}$=>100 µM).

The data in Table 1 show that a compound of this invention exhibits potent antibacterial activity against *Staphylococcus aureus, Enterococcus faecalis, Acinetobacter baumannii*, and *Escherichia coli* D21f2 tolC (MICs=0.05, 6, 10, and 2 µg/ml, respectively).

What is claimed is:

1. A compound of formula (I):

$$X\text{-}\alpha\text{-}Y \qquad (I)$$

wherein:
X is a rifamycin or a rifamycin derivative that binds to the Rif target of a bacterial RNA polymerase;
Y is a moiety that binds to the GE23077 target of a bacterial RNA polymerase; and
α is a linker, wherein X is bonded to α through one of C3 of the rifamycin fused ring system, a moiety pendant from C3 of the rifamycin fused ring system, C4 of the rifamycin fused ring system, a moiety pendant from C4 of the rifamycin fused ring system, C11 of the rifamycin fused ring system, or a moiety pendant from C11 of the rifamycin fused ring system.

2. A compound of formula (I):

$$X\text{-}\alpha\text{-}Y \qquad (I)$$

wherein:
X is a sorangicin or a sorangicin derivative that binds to the Rif target of a bacterial RNA polymerase;
Y is a moiety that binds to the GE23077 target of a bacterial RNA polymerase; and
α is a linker.

3. A compound of formula (I):

$$X\text{-}\alpha\text{-}Y \qquad (I)$$

wherein:
X is a moiety that binds to the Rif target of a bacterial RNA polymerase;
Y is GE23077 or a GE23077 derivative that binds to the GE23077 target of a bacterial RNA polymerase; and
α is a linker.

4. A compound of formula (I):

$$X\text{-}\alpha\text{-}Y \qquad (I)$$

wherein:
X is a moiety that binds to the Rif target of a bacterial RNA polymerase;
Y is GE23077 or a GE23077 derivative that binds to the GE23077 target of a bacterial RNA polymerase; and
α is a linker; wherein Y is bonded to α through a residue corresponding in position to the acyl-Apa residue of GE23077 or the Ama residue of GE23077.

5. A compound of formula (I):

$$X\text{-}\alpha\text{-}Y \qquad (I)$$

wherein:
X is a moiety that binds to the Rif target of a bacterial RNA polymerase;
Y is GE23077 or a GE23077 derivative that binds to the GE23077 target of a bacterial RNA polymerase; and
α is a linker; wherein Y is bonded to α through a residue corresponding in position to the acyl-Apa residue of GE23077.

6. A compound of formula (I):

$$X\text{-}\alpha\text{-}Y \qquad (I)$$

wherein:
X is a moiety that binds to the Rif target of a bacterial RNA polymerase and is selected from the group consisting of rifamycin S, rifamycin SV, and sorangicin A;
Y is GE23077; and
α is a linker.

7. A compound of formula (I):

$$X\text{-}\alpha\text{-}Y \quad\quad (I)$$

wherein:

X is a moiety that binds to the Rif target of a bacterial RNA polymerase and that includes a rifamycin fused ring system or a carboxyl of a sorangicin sidechain;

Y is GE23077 or a GE23077 derivative that binds to the GE23077 target of a bacterial RNA polymerase; and α is —NH— or —S— and connects C3 of the rifamycin fused ring system or the carboxyl of a sorangicin sidechain to a residue corresponding in position to the acyl-Apa residue of GE23077.

* * * * *

UNITED STATES PATENT AND TRADEMARK OFFICE
CERTIFICATE OF CORRECTION

PATENT NO. : 9,415,112 B2
APPLICATION NO. : 14/128391
DATED : August 16, 2016
INVENTOR(S) : David Degen et al.

Page 1 of 1

It is certified that error appears in the above-identified patent and that said Letters Patent is hereby corrected as shown below:

In the claims:

Column 82, Line 10, Claim 1, please delete "wherein X is bonded to α through one of C3" and insert -- wherein X is bonded to α through C3 -- therefore.

Signed and Sealed this
Sixth Day of December, 2016

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 9,415,112 B2 | Page 1 of 1 |
| APPLICATION NO. | : 14/128391 | |
| DATED | : August 16, 2016 | |
| INVENTOR(S) | : Richard H. Ebright et al. | |

It is certified that error appears in the above-identified patent and that said Letters Patent is hereby corrected as shown below:

In the Specification

Column 1, Lines 13-17, please delete "The invention described herein was made with United States Government support under Grant Numbers AI072766 and GM41376 awarded by the National Institutes of Health. The United States Government has certain rights in the invention." and insert -- This invention was made with government support under grant numbers AI072766 and GM041376 awarded by the National Institutes of Health. The government has certain rights in the invention. -- therefor.

Signed and Sealed this
Twenty-fourth Day of January, 2023

Katherine Kelly Vidal
*Director of the United States Patent and Trademark Office*